United States Patent [19]
Treco et al.

[11] Patent Number: 5,641,670
[45] Date of Patent: Jun. 24, 1997

[54] PROTEIN PRODUCTION AND PROTEIN DELIVERY

[75] Inventors: Douglas A. Treco, Arlington; Michael W. Heartlein, Boxborough; Richard F. Selden, Wellesley, all of Mass.

[73] Assignee: Transkaryotic Therapies, Inc., Cambridge, Mass.

[21] Appl. No.: 243,391

[22] Filed: May 13, 1994

Related U.S. Application Data

[63] Continuation-in-part of Ser. No. 985,586, Dec. 3, 1992, abandoned, which is a continuation-in-part of Ser. No. 789,188, Nov. 5, 1991, abandoned, Ser. No. 911,533, Jul. 10, 1992, abandoned, and Ser. No. 787,840, Nov. 5, 1991, abandoned.

[51] Int. Cl.$^6$ .............................. C12N 5/06; C12N 5/08; C12N 15/85
[52] U.S. Cl. ................................. 435/240.2; 435/240.4; 435/320.1; 435/254.11
[58] Field of Search ........................... 435/252.3, 240.2, 435/240.4, 255, 172.3, 69.1, 172.1, 320.1, 254.11; 536/23.5

[56] References Cited

U.S. PATENT DOCUMENTS

| | | | |
|---|---|---|---|
| 4,656,134 | 4/1987 | Ringold et al. | 435/91.1 |
| 4,822,736 | 4/1989 | Kellems et al. | 435/172.3 |
| 5,272,071 | 12/1993 | Chappel | 435/172.3 |

FOREIGN PATENT DOCUMENTS

| | | |
|---|---|---|
| 0117059 | 8/1984 | European Pat. Off. . |
| 0255231 | 3/1988 | European Pat. Off. . |
| 0452894 | 10/1991 | European Pat. Off. . |
| 2159172 | 11/1985 | United Kingdom . |
| 87/00201 | 1/1987 | WIPO . |
| 0236059 | 9/1987 | WIPO . |
| 88/00239 | 1/1988 | WIPO . |
| 88/08306 | 3/1988 | WIPO . |
| 89/01517 | 2/1989 | WIPO . |
| 90/11354 | 4/1990 | WIPO . |
| 90/12025 | 10/1990 | WIPO . |
| 91/13151 | 5/1991 | WIPO . |
| 91/06667 | 5/1991 | WIPO . |
| 91/06666 | 5/1991 | WIPO . |
| 91/00361 | 10/1991 | WIPO . |
| 91/09955 | 11/1991 | WIPO . |
| 91/19796 | 12/1991 | WIPO . |
| 92/03917 | 3/1992 | WIPO . |
| 92/08796 | 5/1992 | WIPO . |
| 92/10561 | 6/1992 | WIPO . |
| 92/20808 | 11/1992 | WIPO . |
| 92/19255 | 11/1992 | WIPO . |
| 93/04169 | 3/1993 | WIPO . |

OTHER PUBLICATIONS

Hung et al., *PNAS*, vol. 83, 1986, pp. 261–264.
Barinaga, *Science*, vol. 266, 1994, p. 1326.
Mulligan, *Science*, vol. 260, 1993, pp. 926–932.
Crystal, *Science*, vol. 270, 1995, pp. 404–410.
Marshall, *Science*, vol. 269, 1995, pp. 1050–1055.

Rosenfeld, Melissa A. et al., "In Vivo Transfer of the Human Cystic Fibrosis Transmembrane Conductance Regulator Gene to the Airway Epithelium," *Cell* 68:143–155 (1992).
Selden, Richard F. et al., "Implantation of Genetically Engineered Fibroblasts into Mice: Implications for Gene Therapy," *Science* 236: 714–718 (1987).
Palmer, Theo D. et al., "Genetically modified skin fibroblasts persist long after transplantation but gradually inactive introduced genes," *Proc. Natl. Acad. Sci. USA* 88:1330–1334 (1991).
Wolff, Jon A. et al., "Direct Gene Transfer into Mouse Muscle In Vivo," *Science* 247:1465–1468 (1990).
Ponticelli, Claudio and Casati, Stefano, "Correction of Anaemia with Recombinant Human Erythropoietin," *Nephron* 52:201–208 (1989).
Browne, J.K., et al., "Erythropoietin: Gene Cloning, Protein Structure, and Biological Properties," Cold Spring Harbor Symposia on Quantitative Biology, vol. LI., Cold Spring Harbor Laboratory, 693–702 (1986).
Faulds, Diana and Sorkin, Eugene M., "Epoetin (Recombinant Human Erythropoietin) A Review of its Pharmacodynamic and Pharmacokinetic Properties and Therapeutic Potential in Anaemia and the Stimulation of Erythropoiesis," *Drugs* 38(6):863–899 (1989).
Capecchi, Mario R., "Altering the Genome by Homologous Recombination," *Science* 244:1288–1292 (1989).
Zheng, Hui et al., "Fidelity of Targeted Recombination in Human Fibroblasts and Murine Embryonic Stem Cells," *Proc. Natl. Acad. Sci. USA* 88:8067–8071 (1991).
Camerini–Otero, R. Daniel and Kucherlapati, Raju, "Right on Target," *The New Biologist* 2:337–341 (1990).
Capecchi, Mario R., "The New Mouse Gentics: Altering the Genome by Gene Targeting," *TIG* 5:70–76 (1989).
Friedmann, Theodore, "Progress Toward Human Gene Therapy," *Science* 244:1275–1281 (1989).
Sedivy, John M. and Sharp, Phillip A., "Positive Genetic Selection for Gene Disruption in Mammalian Cells by Homologous Recombination," *Proc. Natl. Acad. Sci. USA* 86: 227–231 (1989).

(List continued on next page.)

*Primary Examiner*—James S. Ketter
*Attorney, Agent, or Firm*—Hamilton, Brook, Smith & Reynolds, P.C.

[57] ABSTRACT

The invention relates to constructs comprising: a) a targeting sequence; b) a regulatory sequence; c) an exon; and d) an unpaired splice-donor site. The invention further relates to a method of producing protein in vitro or in vivo comprising the homologous recombination of a construct as described above within a cell. The homologously recombinant cell is then maintained under conditions which will permit transcription and translation, resulting in protein expression. The present invention further relates to homologously recombinant cells, including primary, secondary, or immortalized vertebrate cells, methods of making the cells, methods of homologous recombination to produce fusion genes, methods of altering gene expression in the cells, and methods of making a protein in a cell employing the constructs of the invention.

30 Claims, 15 Drawing Sheets

OTHER PUBLICATIONS

Morgan, Jeffrey R. et al., "Expression of an Exogenous Growth Hormone Gene by Trasplantable Human Epidermal Cells," *Science* 237:1476–1479 (1987).

Itzhaki, Jane E. and Porter, Andrew C.G., "Targeted Disruption of a Human Interferon–inducible Gene Detected by Secretion of Human Growth Hormone," *Nucleic Acids Research* 19(14):3835–3842 (1991).

Palmiter, Richard D. et al., "Metallothionein–Human GH Fusion Genes Stimulate Growth of Mice," *Science* 222:809–814 (1983).

Accili, Domenico and Taylor, Simeon L., "Targeted Inactivation of the Insulin Recceptor Gene in Mouse 3T3–L1 Fibroblasts Via Homologous Recombination," *Proc. Natl. Acad. Sci. USA* 88:4708–4712 (1991).

Jasin, Maria et al., "Gene Targeting at the Human CD4 Locus by Epitope Addition," *Genes & Development* 4(2):157–166 (1990).

Schimke, Robert T. et al., "[7] Amplification of Genes in Somatic Mammalian Cells," *Methods in Enzymology* 151:85–104 (1987).

van Deursen, Jan et al., "Modulation of Gene Activity by Consecutive Gene Targeting of One Creatine Kinase M Allele in Mouse Embryonic Stem Cells," *Nucleic Acids Research* 19(10):2637–2643 (1991).

Hammer, R.E., et al., "Partial Correction of Murine Hereditary Growth Disorder by Germ–Line Incorporation of a New Gene," *Nature* 311:65–67 (1984).

Mansour, S.L. et al., "Disruption of the Proto–Oncogene int–2 in Mouse Embryo–Derived Stem Cells: A General Strategy for Targeting Mutations to Non–Selectable Genes," *Nature* 336: 348–352 (1988).

Kramerova, I.A. et al., "Expression of the Cloned Human Erythropoietin Gene in Cho Cells," *Biopolim. Kletka* 5(2):47–51 (1989).

Smith, B.R., "Regulation of Hematopoiesis," *Yale J. Biol. Med.*, 63(5):371–380 (1990).

Morgenstern, J.P. and Land, H., "Advanced Mammalian Gene Transfer: High Titre Retroviral Vectors with Multiple Drug Selection Markers and a Complementary Helper–Free Packaging Cell Line," *Nucleic Acids Research* 18(12):3587–3596 (1990).

Sittler, A.M. and Reudelhuber, T.L., "Tissue–Specific Expression of the Rat Growth Hormone Gene is Due to the Interaction of Multiple Promoter, Not Enhancer, Elements," *DNA and Cell Biology* 9(7):511–518 (1990).

Imagawa, S., et al., "Regulatory Elements of the Erythropoietin Gene," *Blood* 77(2):278–285 (1991).

Fishel, R. et sl., "Biochemical Studies of Homologous and Nonhomologous Recombination in Human Cells," *Biochimie* 73:257–267 (1991).

Shesely, E.G. et al., "Correction of a Human $\beta^S$–globin Gene by Gene Targeting," *Proc. Natl. Acad. Sci. USA* 88:4294–4298 (1991).

Lupton, S.D. et al., "Dominant Positive and Negative Selection Using a Hygromycin Phosphotransferase–Thymidine Kinase Fusion Gene," *Molecular and Cellular Biology* 11(6):3374–3378 (1991).

Scharfmann, R. et al., "Long–Term *In Vivo* Expression of Retrovirus–Mediated Gene Transfer in Mouse Fibroblast Implants," *Proc. Natl. Acad. Sci. USA* 88:4626–4630 (1991).

Wu, G.Y., "Receptor–Mediated Gene Delivery *In Vivo*," *The Journal of Biological Chemistry* 266(22):14338–14342 (1991).

Dhawan, J. et al., "Systemic Delivery of Human Growth Hormone by Injection of Genetically Engineered Myoblasts," *Science* 254:1509–1512 (1991).

Barr, E. and Leiden, J.M., "Systemic Delivery of Recombinant Proteins by Genetically Modified Myoblasts," *Science* 254:1507–1509 (1991).

Chang, D.C. et al., "High Efficiency Gene Transfection by Electroporation Using a Radio–Frequency Electric Field," *Biochimica et Biophysica Acta*, 153–160 (1992).

Keating, A. and Toneguzzo, F., "Gene Transfer by Electroporation: A Model for Gene Therapy," *Bone Marrow Purging and Processing*, 491–498 (1990).

Corey, C.A. et al., "Erythropoiesis in Murine Long–Term Marrow Cultures Following Transfer of the Erythropoietin cDNA into Marrow Stroal Cells," *Exp. Hematol* 18(3):201–204 (1990).

Drucker, D.J. et al., "Cell–Specific Post–Translational Processing of Preproglucagon Expressed from a Metallothionein–Glucagon Fusion Gene," *J. Biol. Chem.* 261(21):9637–9643 (1986).

Lee, Y.C. et al., "Glucagon Gene 3'–Flanking Sequences Direct Formation of Proglucagon Messenger RNA 3'–Ends in Islet and Nonislet Cells Lines," *Mol. Endocrinol* 4(6):800–806(1990).

Kaufman, Randal J., "Selection and Coamplification of Heterologous Genes in Mammalian Cells," *Methods in Enzymology* 185:537–567 (1990).

Kaufman, Randal J., "Strategies for Obtaining High Level Expression in Mammalian Cells,": *Technique* 2(5):221–236 (1990).

Wright, Jim A. et al., "DNA amplification is rare in normal human cells," *PNAS* 87:1791–1795 (1990).

Weidle, Ulrich H. et al., "Amplified expression constructs for human tissue–type plasminogen activator in Chinese hamster ovary cells: instability in the absence of selective pressure," *Gene* 66:193–203 (1988).

Palmiter, Richard D. et al., "Heterologous introns can enhance expression of transgenes in mice," *PNAS* 88:478–482 (1991).

Doetschman, Thomas et al., "Targetted correction of a mutant HPRT gene in mouse embryonic stem cells," *Nature* 330:576–578 (1987).

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGCTTCTGGG CTTCCAGAC                                                                 19

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGGGTCCCTC AGCGAC                                                                     16

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGGGCTTCCA GACCCAG                                                                17

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCAGCTACTT TGCGGAACTC                                                            20

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TTTTGTCGAC GGTACCTTGG TTTTTAAAAC C          31

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCTAGCGGCA ATGGCTACAG GTGAGTACTC GCGGGCTGGG CG          42

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGCCCAGCCC GCGAGTACTC ACCTGTAGCC ATTGCCGCTA GG          42

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TTTTCTCGAG CTAGAACAGA TAGCCAGGCT G          31

( 2 ) INFORMATION FOR SEQ ID NO:9:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GACAGCTCAC CTAGCGGCAA TGGCTACAGG TGAGTACTCA AGCTTCTGGG CTTCCAGACC          60

CAG          63

( 2 ) INFORMATION FOR SEQ ID NO:10:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CTGGGTCTGG AAGCCCAGAA GCTTGAGTAC TCACCTGTAG CCATTGCCGC TAGGTGAGCT          60

GTC          63

( 2 ) INFORMATION FOR SEQ ID NO:11:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TTTTCTCGAG CTCCGCGCCT GGCCGGGGTC CCTC                                34

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AAAAGATCT GGTACCTTGG TTTTAAAAC CAGCCTGGAG                            40

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TTTTAGATCT GAGTACTCAC CTGTAGCCAT TGCCGCTAGG                            40

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CACCTAAAAT GATCTCTCTG G                                                        21

( 2 ) INFORMATION FOR SEQ ID NO:15:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CGCGCCGGGT GACCACACCG GGGGCCCTAG ATCTGGTGAA GCTGGAGCTA CGGAGTAA        58

( 2 ) INFORMATION FOR SEQ ID NO:16:

( i ) SEQUENCE CHARACTERISTICS:

(A) LENGTH: 58 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:16:

TTACTCCGTA GCTCCAGCTT CACCAGATCT AGGGCCCCCG GTGTGGTCAC CCGGCGCG    58

(2) INFORMATION FOR SEQ ID NO:17:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:17:

GTCTCACCGT GATATTCTCG G    21

(2) INFORMATION FOR SEQ ID NO:18:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

TTTTCTCGAG TCGACGACAT TGATTATTGA CTAGT    35

(2) INFORMATION FOR SEQ ID NO:19:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

TTTTAAGCTT GAGTACTCAC CTGTAGCCAT GGTGGATCCC GT    42

PROTEIN PRODUCTION AND PROTEIN DELIVERY

RELATED APPLICATIONS

This application is a Continuation-In-Part of U.S. patent application Ser. No. 07/985,586, now abandoned, filed Dec. 3, 1992, which is a Continuation-In Part of U.S. patent application Ser. No. 07/789,188, now abandoned, filed Nov. 5, 1991 and is also a Continuation-In-Part of U.S. patent application Ser. No. 07/911,533, now abandoned, filed Jul. 10, 1992 and is also a Continuation-In-Part of U.S. patent application Ser. No. 07/787,840, now abandoned, filed Nov. 5, 1991, all of which are incorporated herein by reference. This application also claims priority and is related to PCT/US93/11704, filed Dec. 2, 1993, and is related to PCT/US92/09627, filed Nov. 5, 1992. The teachings of PCT/US92/09267 and PCT/US93/11704 are incorporated herein by reference.

BACKGROUND OF THE INVENTION

Current approaches to treating disease by administering therapeutic proteins include in vitro production of therapeutic proteins for conventional pharmaceutical delivery (e.g. intravenous, subcutaneous, or intramuscular injection) and, more recently, gene therapy.

Proteins of therapeutic interest are generally produced by introducing exogenous DNA encoding the protein of therapeutic interest into appropriate cells. For example, exogenous DNA encoding a desired therapeutic protein is introduced into cells, such as immortalized cells in a vector, such as a plasmid, from which the encoded protein is expressed. Further, it has been suggested that endogenous cellular genes and their expression may be modified by gene targeting. See for example, U.S. Pat. No. 5,272,071, WO 91/06666, WO 91/06667 and WO 90/11354.

Presently-available approaches to gene therapy make use of infectious vectors, such as retroviral vectors, which include the genetic material to be expressed. Such approaches have limitations, such as the potential of generating replication-competent virus during vector production; recombination between the therapeutic virus and endogenous retroviral genomes, potentially generating infectious agents with novel cell specificities, host ranges, or increased virulence and cytotoxicity; independent integration into large numbers of cells, increasing the risk of a tumorigenic insertional event; limited cloning capacity in the retrovirus (which restricts therapeutic applicability) and short-lived in vivo expression of the product of interest. A better approach to providing gene products, particularly one which avoids the limitations and risks associated with presently available methods, would be valuable.

SUMMARY OF THE INVENTION

The present invention relates to improved methods for both the in vitro production of therapeutic proteins and for the production and delivery of therapeutic proteins by gene therapy. In the present method, expression of a desired targeted gene in a cell (i.e., a desired endogenous cellular gene) is altered by the introduction, by homologous recombination into the cellular genome at a preselected site, of DNA which includes at least a regulatory sequence, an exon and a splice donor site. These components are introduced into the chromosomal (genomic) DNA in such a manner that this, in effect, results in production of a new transcription unit (in which the regulatory sequence, the exon and the splice donor site present in the DNA construct are operatively linked to the endogenous gene). As a result of introduction of these components into the chromosomal DNA, the expression of the desired endogenous gene is altered.

Altered gene expression, as used herein, encompasses activating (or causing to be expressed) a gene which is normally silent (unexpressed) in the cell as obtained, increasing expression of a gene which is not expressed at physiologically significant levels in the cell as obtained, changing the pattern of regulation or induction such that it is different than occurs in the cell as obtained, and reducing (including eliminating) expression of a gene which is expressed in the cell as obtained.

The present invention further relates to DNA constructs useful in the method of altering expression of a target gene. The DNA constructs comprise: (a) a targeting sequence; (b) a regulatory sequence; (c) an exon; and (d) an unpaired splice-donor site. The targeting sequence in the DNA construct directs the integration of elements (a)–(d) into a target gene in a cell such that the elements (b)–(d) are operatively linked to sequences of the endogenous target gene. In another embodiment, the DNA constructs comprise: (a) a targeting sequence, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

The following serves to illustrate two embodiments of the present invention, in which the sequences upstream of the human erythropoietin h(EPO) gene are altered to allow expression of hEPO in primary, secondary, or immortalized cells which do not express EPO in detectable quantities in their untransfected state as obtained. In embodiment 1, the targeting construct contains two targeting sequences. The first targeting sequence is homologous to sequences 5' of the second targeting sequence, and both sequences are upstream of the hEPO coding region. The targeting construct also contains a regulatory region (the mMT-1 promoter) an exon (human growth hormone (hGH)) exon 1) and an unpaired splice-donor site. The product of homologous recombination with this targeting construct is shown in FIG. 1.

In embodiment 2, the targeting construct also contains two targeting sequences. The first targeting sequence is homologous to sequences within the endogenous hEPO regulatory region, and the second targeting sequence is homologous to hEPO intron 1. The targeting construct also contains a regulatory region (the mMT-1 promotor), an exon (hGH exon 1) and an unpaired splice-donor site. The product of homologous recombination with this targeting construct is shown in FIG. 2.

In these two embodiments, the products of the targeting events are chimeric transcription units which generate a mature mRNA in which the first exon of the hGH gene is positioned upstream of hEPO exons 2–5. The product of transcription, splicing, and translation is a protein in which amino acids 1–4 of the hEPO signal peptide are replaced with amino acid residues 1–3 of hGH. The two embodiments differ with respect to both the relative positions of the regulatory sequences of the targeting construct that are inserted and the specific pattern of splicing that needs to occur to produce the final, processed transcript.

The invention further relates to a method of producing protein in vitro or in vivo through introduction of a construct as described above into host cell chromosomal DNA by homologous recombination to produce a homologously recombinant cell. The homologously recombinant cell is then maintained under conditions which will permit transcription, translation and secretion, resulting in production of the protein of interest.

The present invention relates to transfected cells, such as transfected primary or secondary cells (i.e., non-immortalized cells) and transfected immortalized cells, useful for producing proteins, particularly therapeutic proteins, methods of making such cells, methods of using the cells for in vitro protein production, and methods of gene therapy. Cells of the present invention are of vertebrate origin, particularly of mammalian origin, and even more particularly of human origin. Cells produced by the method of the present invention contain DNA which encodes a therapeutic product, DNA which is itself a therapeutic product and/or DNA which causes the transfected cells to express a gene at a higher level or with a pattern of regulation or induction that is different than occurs in the corresponding nontransfected cell.

The present invention also relates to methods by which cells, such as primary, secondary, and immortalized cells, are transfected to include exogenous genetic material, methods of producing clonal cell strains or heterogenous cell strains, and methods of immunizing animals or producing antibodies in immunized animals, using the transfected primary, secondary, or immortalized cells.

The present invention relates particularly to a method of gene targeting or homologous recombination in eukaryotic cells, such as cells of fungal, plant or animal, e.g., vertebrate, particularly mammalian, and even more particularly, human origin. That is, it relates to a method of introducing DNA into primary, secondary, or immortalized cells of vertebrate origin through homologous recombination, such that the DNA is introduced into genomic DNA of the primary, secondary, or immortalized cells at a preselected site. The targeting sequences used are selected with reference to the site into which the DNA in the targeting DNA construct is to be inserted. The present invention further relates to homologously recombinant primary, secondary, or immortalized cells, referred to as homologously recombinant (HR) primary, secondary or immortalized cells, produced by the present method and to uses of the HR primary, secondary, or immortalized cells.

In one embodiment of the present invention in which expression of a gene is altered, the gene is activated. That is, a gene present in primary, secondary, or immortalized cells of vertebrate origin, which is normally not expressed in the cells as obtained, is activated and, as a result, the encoded protein is expressed. In this embodiment, homologous recombination is used to replace, disable, or disrupt the regulatory region normally associated with the gene in cells as obtained through the insertion of a regulatory sequence which causes the gene to be expressed at levels higher than evident in the corresponding nontransfected cell.

In one embodiment, the activated gene can be further amplified by the inclusion of an amplifiable selectable marker gene which has the property that cells containing amplified copies of the selectable marker gene can be selected for by culturing the cells in the presence of the appropriate selectable agent. The activated endogenous gene is amplified in tandem with the amplifiable selectable marker gene. Cells containing many copies of the activated endogenous gene are useful for in vitro protein production and gene therapy.

Gene targeting and amplification as disclosed in the present invention are particularly useful for activating the expression of genes which form transcription units which are sufficiently large that they are difficult to isolate and express, or for activating genes for which the entire protein coding region is unavailable or has not been cloned.

In a further embodiment, expression of a gene which is expressed in a cell as obtained is enhanced or caused to display a pattern of regulation or induction that is different than evident in the corresponding nontransfected cell. In another embodiment, expression of a gene which is expressed in a cell as obtained is reduced (i.e., lessened or eliminated). The present invention also describes a method by which homologous recombination is used to convert a gene into a cDNA copy, devoid of introns, for transfer into yeast or bacteria for in vitro protein production.

Transfected cells of the present invention are useful in a number of applications in humans and animals. In one embodiment, the cells can be implanted into a human or an animal for protein delivery in the human or animal. For example, hGH, hEPO, human insulinotropin, and other proteins can be delivered systemically or locally in humans for therapeutic benefits. In addition, transfected non-human cells producing growth hormone, erythropoietin, insulinotropin and other proteins of non-human origin may be produced.

Barrier devices, which contain transfected cells which express a therapeutic product and through which the therapeutic product is freely permeable, can be used to retain cells in a fixed position in vivo or to protect and isolate the cells from the host's immune system. Barrier devices are particularly useful and allow transfected immortalized cells, transfected xenogeneic cells, or transfected allogeneic cells to be implanted for treatment of human or animal conditions or for agricultural uses (e.g., bovine growth hormone for dairy production). Barrier devices also allow convenient short-term (i.e., transient) therapy by providing ready access to the cells for removal when the treatment regimen is to be halted for any reason. In addition, transfected xenogeneic and allogeneic cells may be used in the absence of barrier devices for short-term gene therapy, such that the gene product produced by the cells will be delivered in vivo until the cells are rejected by the host's immune system.

Transfected cells of the present invention are also useful for eliciting antibody production or for immunizing humans and animals against pathogenic agents. Implanted transfected cells can be used to deliver immunizing antigens that result in stimulation of the host's cellular and humoral immune responses. These immune responses can be designed for protection of the host from future infectious agents (i.e., for vaccination), to stimulate and augment the disease-fighting capabilities directed against an ongoing infection, or to produce antibodies directed against the antigen produced in vivo by the transfected cells that can be useful for therapeutic or diagnostic purposes. Removable barrier devices containing the cells can be used to allow a simple means of terminating exposure to the antigen. Alternatively, the use of cells that will ultimately be rejected (xenogeneic or allogeneic transfected cells) can be used to limit exposure to the antigen, since antigen production will cease when the cells have been rejected.

The methods of the present invention can be used to produce primary, secondary, or immortalized cells producing a wide variety of therapeutically useful products, including (but not limited to): hormones, cytokines, antigens, antibodies, enzymes, clotting factors, transport proteins, receptors, regulatory proteins, structural proteins, transcription factors, ribozymes or anti-sense RNA. Additionally, the methods of the present invention can be used to produce cells which produce non-naturally occurring ribozymes, proteins, or nucleic acids which are useful for in vitro production of a therapeutic product or for gene therapy.

DETAILED DESCRIPTION OF THE INVENTION

Figure 1:
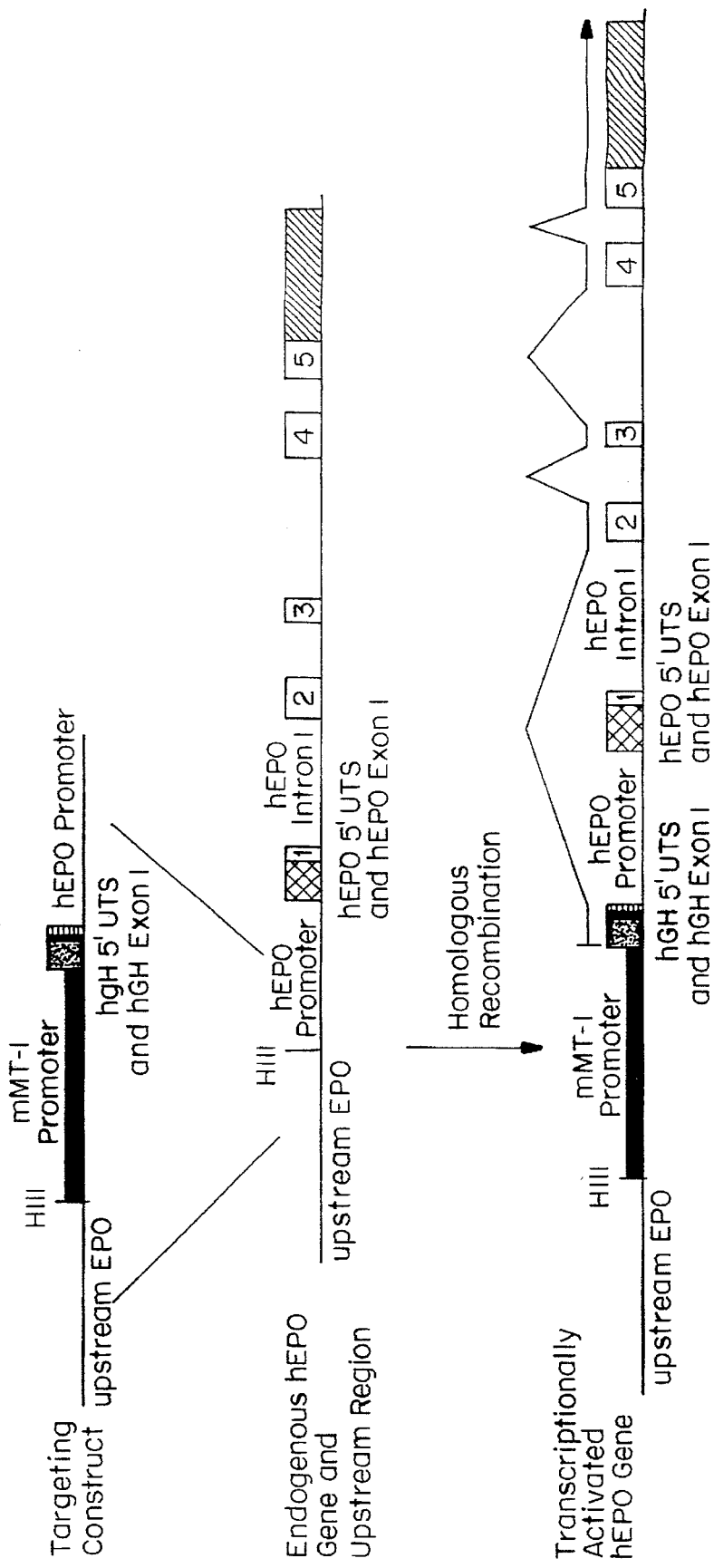
FIG. 1 is a schematic diagram of a strategy for transcriptionally activating the hEPO gene; thick lines, mouse metallothionein I promoter; stippled box, 5' untranslated region of hGH; solid box, hGH exon 1; striped box, 10 bp splice-donor sequence from hEPO intron 1; cross-hatched box, 5' untranslated region of hEPO; open numbered boxes, hEPO coding sequences; diagonally-stripped box, hEPO 3' untranslated sequences; HIII, HindIII site.

The invention is based upon the discovery that the regulation or activity of endogenous genes of interest in a cell can be altered by inserting into the cell genome, at a preselected site, through homologous recombination, DNA constructs comprising: (a) a targeting sequence; (b) a regulatory sequence; (c) an exon and (d) an unpaired splice-donor site, wherein the targeting sequence directs the integration of elements (a)–(d) such that the elements (b)–(d) are operatively linked to the endogenous gene. In another embodiment, the DNA constructs comprise: (a) a targeting sequence, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the first exon of the endogenous gene. The targeting sequences used are selected with reference to the site into which the DNA is to be inserted. In both embodiments the targeting event is used to create a new transcription unit, which is a fusion product of sequences introduced by the targeting DNA constructs and the endogenous cellular gene. As discussed herein, for example, the formation of the new transcription unit allows transcriptionally silent genes (genes not expressed in a cell prior to transfection) to be activated in host cells by introducing into the host cell's genome DNA constructs of the present invention. As also discussed herein, the expression of an endogenous gene which is expressed in a cell as obtained can be altered in that it is increased, reduced, including eliminated, or the pattern of regulation or induction may be changed through use of the method and DNA constructs of the present invention.

The present invention as set forth above, relates to a method of gene or DNA targeting in cells of eukaryotic origin, such as of fungal, plant or animal, such as, vertebrate, particularly mammalian, and even more particularly human origin. That is, it relates to a method of introducing DNA into a cell, such as primary, secondary, or immortalized cells of vertebrate origin, through homologous recombination or targeting of the DNA, which is introduced into genomic DNA of the cells at a preselected site. It is particularly related to homologous recombination in which the transcription and/or translation products of endogenous genes are modified through the use of DNA constructs comprising a targeting sequence, a regulatory sequence, an exon and a splice-donor site. The present invention further relates to homologously recombinant cells produced by the present method and to uses of the homologously recombinant cells.

The present invention also relates to a method of activating a gene which is present in primary cells, secondary cells or immortalized cells of vertebrate origin, but is normally not expressed in the cells. Homologous recombination or targeting is used to introduce into the cell's genome sequences which causes the gene to be expressed in the recipient cell. In a further embodiment, expression of a gene in a cell is enhanced or the pattern of regulation or induction of a gene is altered, through introduction of the DNA construct. As a result, the encoded product is expressed at levels higher than evident in the corresponding nontransfected cell. The present method and DNA constructs are also useful to produce cells in which expression of a desired product is less in the transfected cell than in the corresponding nontransfected cell. That is, in the transfected cell, less protein (including no protein) is produced than in the cells as obtained.

In another embodiment, a normally silent gene encoding a desired product is activated in a transfected, primary, secondary, or immortalized cell and amplified. This embodiment is a method of introducing, by homologous recombination with genomic DNA, DNA sequences which are not normally functionally linked to the endogenous gene and (1) which, when inserted into the host genome at or near the endogenous gene, serve to alter (e.g., activate) the expression of the endogenous gene, and further (2) allow for selection of cells in which the activated endogenous gene is amplified. Alternatively, expression of a gene normally expressed in the cell as obtained is enhanced and the gene is amplified.

The following is a description of the DNA constructs of the present invention, methods in which they are used to produce transfected cells, transfected cells and uses of these cells.

The DNA Construct

The DNA construct of the present invention includes at least the following components: a targeting sequence; a regulatory sequence; an exon and an unpaired splice-donor site. In the construct, the exon is 3' of the regulatory sequence and the unpaired splice-donor site is 3' of the exon. In addition, there can be multiple exons and/or introns preceding (5' to) the exon flanked by the unpaired splice-donor site. As described herein, there frequently are additional construct components, such as a selectable markers or amplifiable markers.

The DNA in the construct may be referred to as exogenous. The term "exogenous" is defined herein as DNA which is introduced into a cell by the method of the present invention, such as with the DNA constructs defined herein. Exogenous DNA can possess sequences identical to or different from the endogenous DNA present in the cell prior to transfection.

The Targeting Sequence or Sequences

The targeting sequence or sequences are DNA sequences which permit legitimate homologous recombination into the genome of the selected cell containing the gene of interest. Targeting sequences are, generally, DNA sequences which are homologous to (i.e., identical or sufficiently similar to cellular DNA such that the targeting sequence and cellular DNA can undergo homologous recombination) DNA sequences normally present in the genome of the cells as obtained (e.g., coding or noncoding DNA, lying upstream of the transcriptional start site, within, or downstream of the transcriptional stop site of a gene of interest, or sequences present in the genome through a previous modification). The targeting sequence or sequences used are selected with reference to the site into which the DNA in the DNA construct is to be inserted.

One or more targeting sequences can be employed. For example, a circular plasmid or DNA fragment preferably employs a single targeting sequence. A linear plasmid or DNA fragment preferably employs two targeting sequences. The targeting sequence or sequences can, independently, be within the gene of interest (such as, the sequences of an exon and/or intron), immediately adjacent to the gene of interest (i.e., with no additional nucleotides between the targeting sequence and the coding region of the gene of interest), upstream gene of interest (such as the sequences of the upstream non-coding region or endogenous promoter sequences), or upstream of and at a distance from the gene (such as, sequences upstream of the endogenous promoter). The targeting sequence or sequences can include those regions of the targeted gene presently known or sequenced and/or regions further upstream which are structurally uncharacterized but can be mapped using restriction enzymes and determined by one skilled in the art.

As taught herein, gene targeting can be used to insert a regulatory sequence isolated from a different gene, assembled from components isolated from difference cellular and/or viral sources, or synthesized as a novel regulatory sequence by genetic engineering methods within, immediately adjacent to, upstream, or at a substantial distance from an endogenous cellular gene. Alternatively or additionally, sequences which affect the structure or stability of the RNA or protein produced can be replaced, removed, added, or otherwise modified by targeting. For example, RNA stability elements, splice sites, and/or leader sequences of RNA molecules can be modified to improve or alter the function, stability, and/or translatability of an RNA molecule. Protein sequences may also be altered, such as signal sequences, propeptide sequences, active sites, and/or structural sequences for enhancing or modifying transport, secretion, or functional properties of a protein. According to this method, introduction of the exogenous DNA results in the alteration of the normal expression properties of a gene and/or the structural properties of a protein or RNA.

The Regulatory Sequence

The regulatory sequence of the DNA construct can be comprised of one or more promoters (such as a constitutive or inducible promoter), enhancers, scaffold-attachment regions or matrix attachment sites, negative regulatory elements, transcription factor binding sites, or combinations of said sequences.

The regulatory sequence can contain an inducible promoter, with the result that cells as produced or as introduced into an individual do not express the product but can be induced to do so (i.e., expression is induced after the transfected cells are produced but before implantation or after implantation). DNA encoding the desired product can, of course, be introduced into cells in such a manner that it is expressed upon introduction (e.g., under a constitutive promoter). The regulatory sequence can be isolated from cellular or viral genomes, (such regulatory sequences include those that regulate the expression of SV40 early or late genes, adenovirus major late genes, the mouse metallothionein-I gene, the elongation factor-1α gene, cytomegalovirus genes, collagen genes, actin genes, immunoglobulin genes or the HMG-CoA reductase gene). The regulatory sequence preferably contains transcription factor binding sites, such as a TATA Box, CCAAT Box, AP1, Sp1 or NF-κB binding sites.

Additional DNA Construct Elements

The DNA construct further comprises one or more exons. An exon is defined herein as a DNA sequence which is copied into RNA and is present in a mature mRNA molecule. The exons can, optionally, contain DNA which encodes one or more amino acids and/or partially encodes an amino acid (i.e., one or two bases of a codon). Alternatively, the exon contains DNA which corresponds to a 5' noncoding region. Where the exogenous exon or exons encode one or more amino acids and/or a portion of an amino acid, the DNA construct is designed such that, upon transcription and splicing, the reading frame is in-frame with the second exon or coding region of the targeted gene. As used herein, in-frame means that the encoding sequences of a first exon and a second exon, when fused, join together nucleotides in a manner that does not change the appropriate reading frame of the portion of the mRNA derived from the second exon.

Where the first exon of the targeted gene contains the sequence ATG to initiate translation, the exogenous exon of the construct preferably contains an ATG and, if required, one or more nucleotides such that the resulting coding region of the mRNA including the second and subsequent exons of the targeted gene is in-frame. Examples of such targeted genes in which the first exon contains an ATG include the genes encoding hEPO, hGH, human colony stimulating factor-granulocyte/macrophage (hGM-CSF), and human colony stimulating factor-granulocyte (hG-CSF).

A splice-donor site is a sequence which directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. Splice-donor sites have a characteristic consensus sequence represented as: (A/C)AG GURAGU (where R denotes a purine nucleotide) with the GU in the fourth and fifth positions, being required (Jackson, I. J., *Nucleic Acids Research* 19: 3715–3798 (1991)). The first three bases of the splice-donor consensus site are the last three bases of the exon. Splice-donor sites are functionally defined by their ability to effect the appropriate reaction within the mRNA splicing pathway.

An unpaired splice-donor site is defined herein as a splice-donor site which is present in a targeting construct and is not accompanied in the construct by a splice-acceptor site positioned 3' to the unpaired splice-donor site. The unpaired splice-donor site results in splicing to an endogenous splice-acceptor site.

A splice-acceptor site in a sequence which, like a splice-donor site, directs the splicing of one exon to another exon. Acting in conjunction with a splice-donor site, the splicing apparatus uses a splice-acceptor site to effect the removal of an intron. Splice-acceptor sites have a characteristic sequence represented as: YYYYYYYYYYNYAG, where Y denotes any pyrimidine and N denotes any nucleotide (Jackson, I. J., *Nucleic Acids Research* 19:3715–3798 (1991) ).

An intron is defined as a sequence of one or more nucleotides lying between two exons and which is removed, by splicing, from a precursor RNA molecule in the formation of an mRNA molecule.

The regulatory sequence is, for example, operatively linked to an ATG start codon, which initiates translation. Optionally, a CAP site (a specific mRNA initiation site which is associated with and utilized by the regulatory region) is operatively linked to the regulatory sequence and the ATG start codon. Alternatively, the CAP site associated with and utilized by the regulatory sequence is not included in the targeting construct, and the transcriptional apparatus will define a new CAP site. For most genes, a CAP site is usually found approximately 25 nucleotides 3' of the TATA box. In one embodiment, the splice-donor site is placed immediately adjacent to the ATG, for example, where the presence of one or more nucleotides is not required for the exogenous exon to be in-frame with the second exon of the targeted gene. Preferably, DNA encoding one or more amino acids or portions of an amino acid in-frame with the coding sequence of the targeted gene, is placed immediately adjacent to the ATG on its 3' side. In such an embodiment, the splice-donor site is placed immediately adjacent to the encoding DNA on its 3' side.

Operatively linked or functionally placed is defined as a configuration in which the exogenous regulatory sequence, exon, splice-donor site and, optionally, a sequence and splice-acceptor site are appropriately targeted at a position relative to an endogenous gene such that the regulatory element directs the production of a primary RNA transcript which initiates at a CAP site (optionally included in the targeting construct) and includes sequences corresponding to the exon and splice-donor site of the targeting construct, DNA lying upstream of the endogenous gene's regulatory region (if present), the endogenous gene's regulatory region (if present), the endogenous genes 5' nontranscribed region (if present), and exons and introns (if present) of the endogenous gene. In an operatively linked configuration the splice-donor site of the targeting construct directs a splicing event to a splice-acceptor site flanking one of the exons of the endogenous gene, such that a desired protein can be produced from the fully spliced mature transcript. In one embodiment, the splice-acceptor site is endogenous, such that the splicing event is directed to an endogenous exon, for example, of the endogenous gene. In another embodiment where the splice-acceptor site is included in the targeting construct, the splicing event removes the intron introduced by the targeting construct.

The encoding DNA (e.g., in exon 1 of the targeting construct) employed can optionally encode one or more amino acids, and/or a portion of an amino acid, which are the same as those of the endogenous protein. The encoding DNA sequence employed herein can, for example, correspond to the first exon of the gene of interest. The encoding DNA can alternatively encode one or more amino acids or a portion of an amino acid different from the first exon of the protein of interest. Such an embodiment is of particular interest where the amino acids of the first exon of the protein of interest are not critical to the activity or activities of the protein. For example, when fusions to the endogenous hEPO gene are constructed, sequences encoding the first exon of hGH can be employed. In this example, fusion of hGH exon 1 to hEPO exon 2 results in the formation of a hybrid signal peptide which is functional. In related constructs, any exon of human or non-human origin in which the encoded amino acids do not prevent the function of the hybrid signal peptide can be used. In a related embodiment, this technique can also be employed to correct a mutation found in a target gene.

Where the desired product is a fusion protein of the endogenous protein and encoding sequences in the targeting construct, the exogenous encoding DNA incorporated into the cells by the present method includes DNA which encodes one or more exons or a sequence of cDNA corresponding to a translation or transcription product which is to be fused to the product of the endogenous targeted gene. In this embodiment, targeting is used to prepare chimeric or multifunctional proteins which combine structural, enzymatic, or ligand or receptor binding properties from two or more proteins into one polypeptide. For example, the exogenous DNA can encode an anchor to the membrane for the targeted protein or a signal peptide to provide or improve cellular secretion, leader sequences, enzymatic regions, transmembrane domain regions, co-factor binding regions or other functional regions. Examples of proteins which are not normally secreted, but which could be fused to a signal protein to provide secretion include dopa-decarboxylase, transcriptional regulatory proteins, α-galactosidase and tyrosine hydroxylase.

Where the first exon of the targeted gene corresponds to a non-coding region (for example, the first exon of the follicle-stimulating hormone beta (FSHβ) gene, an exogenous ATG is not required and, preferably, is omitted.

The DNA of the construct can be obtained from sources in which it occurs in nature or can be produced, using genetic engineering techniques or synthetic processes.

The Targeted Gene and Resulting Product

The DNA construct, when transfected into cells, such as primary, secondary or immortalized cells, can control the expression of a desired product for example, the active or, functional portion of the protein or RNA. The product can be, for example, a hormone, a cytokine, an antigen, an antibody, an enzyme, a clotting factor, a transport protein, a receptor, a regulatory protein, a structural protein, a transcription factor, an anti-sense RNA, or a ribozyme. Additionally, the product can be a protein or a nucleic acid which does not occur in nature (i.e., a fusion protein or nucleic acid).

The method as described herein can produce one or more therapeutic products, such as erythropoietin, calcitonin, growth hormone, insulin, insulinotropin, insulin-like growth factors, parathyroid hormone, interferon β, and interferon β, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte, CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factors V, blood clotting factor VII, blood clotting factor VIII, blood clotting factor IX, blood clotting factor X, blood clotting factor XIII, apolipoprotein E or apolipoprotein A-I, globins, low density lipoprotein receptor, IL-2 receptor, IL-2 antagonists, alpha-1 anti-trypsin, immune response modifiers, and soluble CD4.

Selectable Markers and Amplification

The identification of the targeting event can be facilitated by the use of one or more selectable marker genes. These markers can be included in the targting construct or be present on different constructs. Selectable markers can be divided into two categories: positively selectable and negatively selectable (in other words, markers for either positive selection or negative selection). In positive selection, cells expressing the positively selectable marker are capable of surviving treatment with a selective agent (such as neo, xanthine-guanine phosphoribosyl transferase (gpt), dhfr, adenosine deaminase (ada), puromycin (pac), hygromycin (hyg), CAD which encodes carbamyl phosphate synthase, aspartate transcarbamylase, and dihydro-orotase glutamine synthetase (GS), multidrug resistance 1 (mdrl) and histidine D (hisD), allowing for the selection of cells in which the targeting construct integrated into the host cell genome. In negative selection, cells expressing the negatively selectable marker are destroyed in the presence of the selective agent. The identification of the targeting event can be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker (Mansour, S. L. et al., Nature 336:348–352 (1988)). Markers useful for this purpose include the Herpes Simplex Virus thymidine kinase (TK) gene or the bacterial gpt gene.

A variety of selectable markers can be incorporated into primary, secondary or immortalized cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac, hyg, CAD, GS, mdrl and hisD. The selectable phenotype conferred makes it possible to identify and isolate recipient cells.

Amplifiable genes encoding selectable markers (e.g., ada, GS, dhfr and the multifunctional CAD gene) have the added characteristic that they enable the selection of cells containing amplified copies of the selectable marker inserted into the genome. This feature provides a mechanism for significantly increasing the copy number of an adjacent or linked gene for which amplification is desirable. Mutated versions of these sequences showing improved selection properties and other amplifiable sequences can also be used.

The order of components in the DNA construct can vary. Where the construct is a circular plasmid, the order of elements in the resulting structure can be: targeting sequence—plasmid DNA (comprised of sequences used for the selection and/or replication of the targeting plasmid in a microbial or other suitable host)—selectable marker(s)—regulatory sequence—exon—splice-donor site. Preferably, the plasmid containing the targeting sequence and exogenous DNA elements is cleaved with a restriction enzyme that cuts one or more times within the targeting sequence to create a linear or gapped molecule prior to introduction into a recipient cell, such that the free DNA ends increase the frequency of the desired homologous recombination event as described herein. In addition, the free DNA ends may be treated with an exonuclease to create protruding 5' or 3' overhanging single-stranded DNA ends to increase the frequency of the desired homologous recombination event. In this embodiment, homologous recombination between the targeting sequence and the cellular target will result in two copies of the targeting sequences, flanking the elements contained within the introduced plasmid.

Where the construct is linear, the order can be, for example: a first targeting sequence—selectable marker—regulatory sequence—an exon—a splice-donor site—a second targeting sequence or, in the alternative, a first targeting sequence—regulatory sequence—an exon—a splice-donor site—DNA encoding a selectable marker—a second targeting sequence. Cells that stably integrate the construct will survive treatment with the selective agent; a subset of the stably transfected cells will be homologously recombinant cells. The homologously recombinant cells can be identified by a variety of techniques, including PCR, Southern hybridization and phenotypic screening.

In another embodiment, the order of the construct can be: a first targeting sequence—selectable marker—regulatory sequence—an exon—a splice-donor site—an intron—a splice-acceptor site—a second targeting sequence.

Alternatively, the order of components in the DNA construct can be, for example: a first targeting sequence—selectable marker 1—regulatory sequence—an exon—a splice-donor site—a second targeting sequence—selectable marker 2, or, alternatively, a first targeting sequence—regulatory sequence—an exon—a splice-donor site—selectable marker 1—a second targeting sequence—selectable marker 2. In this embodiment selectable marker 2 displays the property of negative selection. That is, the gene product of selectable marker 2 can be selected against by growth in an appropriate media formulation containing an agent (typically a drug or metabolite analog) which kills cells expressing selectable marker 2. Recombination between the targeting sequences flanking selectable marker 1 with homologous sequences in the host cell genome results in the targeted integration of selectable marker 1, while selectable marker 2 is not integrated. Such recombination events generate cells which are stably transfected with selectable marker 1 but not stably transfected with selectable marker 2, and such cells can be selected for by growth in the media containing the selective agent which selects for selectable marker 1 and the selective agent which selects against selectable marker 2.

The DNA construct also can include a positively selectable marker that allows for the selection of cells containing amplified copies of that marker. The amplification of such a marker results in the co-amplification of flanking DNA sequences. In this embodiment, the order of construct components is, for example: a first targeting sequence—an amplifiable positively selectable marker—a second selectable marker (optional)—regulatory sequence—an exon—a splice-donor site—a second targeting DNA sequence.

In this embodiment, the activated gene can be further amplified by the inclusion of a selectable marker gene which has the property that cells containing amplified copies of the selectable marker gene can be selected for by culturing the cells in the presence of the appropriate selectable agent. The activated endogenous gene will be amplified in tandem with the amplified selectable marker gene. Cells containing many copies of the activated endogenous gene may produce very high levels of the desired protein and are useful for in vitro protein production and gene therapy.

In any embodiment, the selectable and amplifiable marker genes do not have to lie immediately adjacent to each other.

Figure 4:
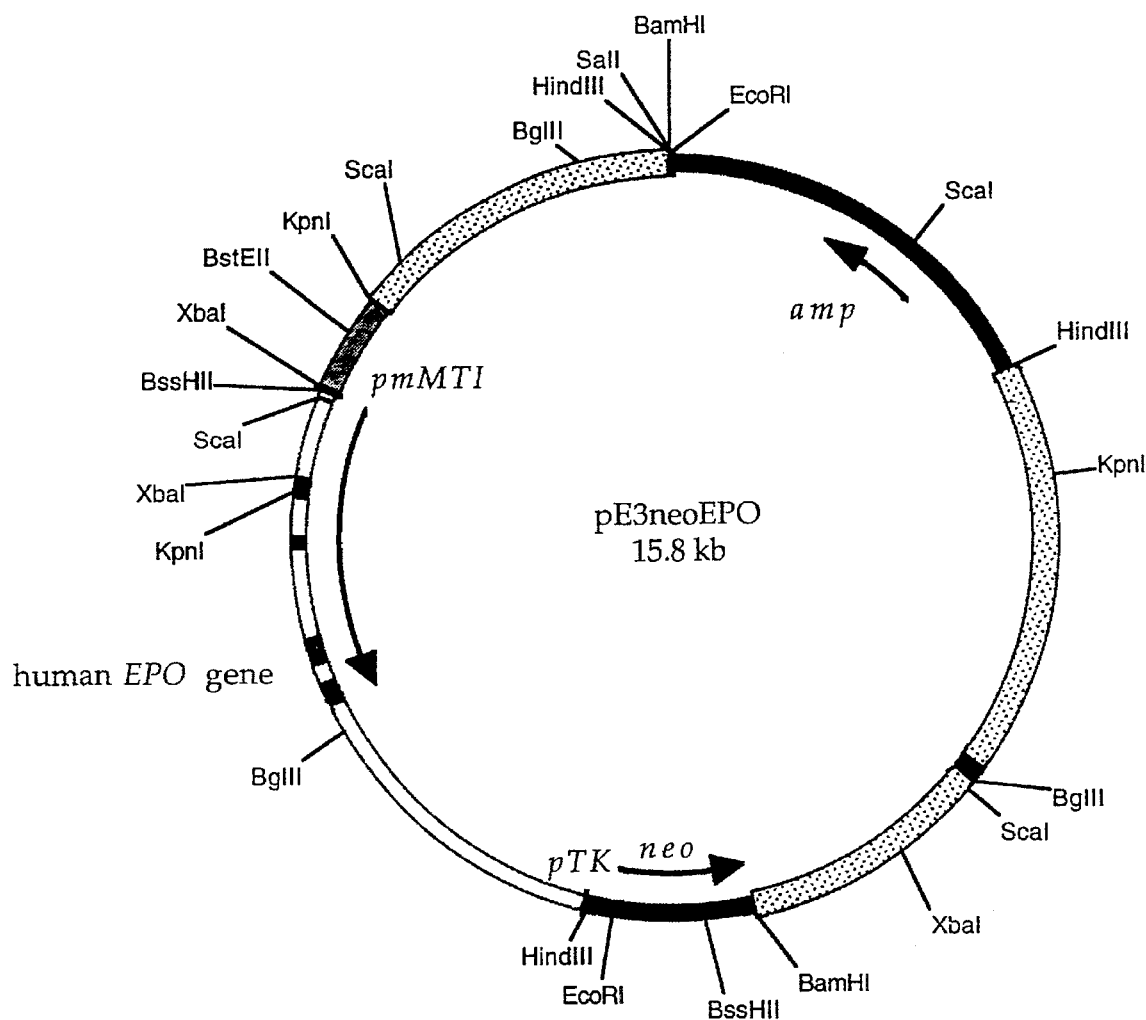
FIG. 4 is a schematic representation of plasmid pE3neoEPO. The positions of the human erythropoietin gene and the neomycin phosphotranferase gene (neo) and ampicillin (amp) resistance genes are indicated. Arrows indicate the directions of transcription of the various genes. pmMT1 denotes the mouse metallothionein promoter (driving hEPO expression) and pTK denotes the Herpes Simplex Virus thymidine kinase promoter (driving neo expression). The dotted regions of the map mark the positions of sequences derived from the human hypoxanthine-guanine phosphoribosyl transferase (HPRT) locus. The relative positions of restriction endonuclease recognition sites are indicated.

Optionally, the DNA construct can include a bacterial origin of replication and bacterial antibiotic resistance markers or other selectable markers, which allow for large-scale plasmid propagation in bacteria or any other suitable cloning/host system. A DNA construct which includes DNA encoding a selectable marker, along with additional sequences, such as a promoter, and splice junctions, can be used to confer a selectable phenotype upon transfected cells (e.g., plasmid pcDNEO, schematically represented in FIG. 4). Such a DNA construct can be co-transfected into primary or secondary cells, along with a targeting DNA sequence, using methods described herein.

Transfection and Homologous Recombination

According to the present method, the construct is introduced into the cell, such as a primary, secondary, or immortalized cell, as a single DNA construct, or as separate DNA sequences which become incorporated into the chromosomal or nuclear DNA of a transfected cell.

The targeting DNA construct, including the targeting sequences, regulatory sequence, an exon, a splice-donor site and selectable marker gene(s), can be introduced into cells on a single DNA construct or on separate constructs. The total length of the DNA construct will vary according to the number of components (targeting sequences, regulatory sequences, exons, selectable marker gene, and other elements, for example) and the length of each. The entire construct length will generally be at least about 200 nucleotides. Further, the DNA can be introduced as linear, double-stranded (with or without single-stranded regions at one or both ends), single-stranded, or circular.

Any of the construct types of the disclosed invention is then introduced into the cell to obtain a transfected cell. The transfected cell is maintained under conditions which permit homologous recombination, as is known in the art (Capecchi, M. R., Science 244:1288–1292 (1989)). When the homologously recombinant cell is maintained under conditions sufficient for transcription of the DNA, the regulatory region introduced by the targeting construct, as in the case of a promoter, will activate transcription.

The DNA constructs may be introduced into cells by a variety of physical or chemical methods, including electroporation, microinjection, microprojectile bombardment, calcium phosphate precipitation, and liposome-, polybrene-, or DEAE dextran-mediated transfection. Alternatively, infectious vectors, such as retroviral, herpes, adenovirus, adenovirus-associated, mumps and poliovirus vectors, can be used to introduce the DNA.

Optionally, the targeting DNA can be introduced into a cell in two or more separate DNA fragments. In the event two fragments are used, the two fragments share DNA sequence homology (overlap) at the 3' end of one fragment and the 5' end of the other, while one carries a first targeting sequence and the other carries a second targeting sequence.

Upon introduction into a cell, the two fragments can undergo homologous recombination to form a single fragment with the first and second targeting sequences flanking the region of overlap between the two original fragments. The product fragment is then in a form suitable for homologous recombination with the cellular target sequences. More than two fragments can be used, designed such that they will undergo homologous recombination with each other to ultimately form a product suitable for homologous recombination with the cellular target sequences as described above.

The Homologously Recombinant Cells

The targeting event results in the insertion of the regulatory sequence of the targeting construct, placing the endogenous gene under their control (for example, by insertion of either a promoter or an enhancer, or both, upstream of the endogenous gene or regulatory region). Optionally, the targeting event can simultaneously result in the deletion of the endogenous regulatory element, such as the deletion of a tissue-specific negative regulatory element. The targeting event can replace an existing element; for example, a tissue-specific enhancer can be replaced by an enhancer that has broader or different cell-type specificity than the naturally-occurring elements, or displays a pattern of regulation or induction that is different from the corresponding nontransfected cell. In this embodiment the naturally occurring sequences are deleted and new sequences are added. Alternatively, the endogenous regulatory elements are not removed or replaced but are disrupted of disabled by the targeting event, such as by targeting the exogenous sequences within the endogenous regulatory elements.

After the DNA is introduced into the cell, the cell is maintained under conditions appropriate for homologous recombination to occur between the genomic DNA and a portion of the introduced DNA, as is known in the art (Capecchi, M. R., Science 244:1288–1292 (1989)).

Homologous recombination between the genomic DNA and the introduced DNA results in a homologously recombinant cell, such as a fungal, plant or animal, and particularly, primary, secondary, or immortalized human or other mammalian cell in which sequences which alter the expression of an endogenous gene are operatively linked to an endogenous gene encoding a product, producing a new transcription unit with expression and/or coding potential that is different from that of the endogenous gene. Particularly, the invention includes a homologously recombinant cell comprising regulatory sequences and an exon, flanked by a splice-donor site, which are introduced at a predetermined site by a targeting DNA construct, and are operatively linked to the second exon of an endogenous gene. Optionally, there may be multiple exogenous exons (coding or non-coding) and introns operatively linked to any exon of the endogenous gene. The resulting homologously recombinant cells are cultured under conditions which select for amplification, if appropriate, of the DNA encoding the amplifiable marker and the novel transcriptional unit. With or without amplification, cells produced by this method can be cultured under conditions, as are known in the art, suitable for the expression of the protein, thereby producing the protein in vitro, or the cells can be used for in vivo delivery of a therapeutic protein (i.e., gene therapy).

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized.

Immortalized cells are cell lines (as opposed to cell strains with the designation "strain" reserved for primary and secondary cells), a critical feature of which is that they exhibit an apparently unlimited lifespan in culture.

Cells selected for the subject method can fall into four types or categories: 1) cells which do not, as obtained, make or contain the protein or product (such as a protein that is not normally expressed by the cell or a fusion protein not normally found in nature), 2) cells which make or contain the protein or product but in quantities other than that desired (such as, in quantities less than the physiologically normal lower level for the cell as it is obtained), 3) cells which make the protein or product at physiologically normal levels for the cell as it is obtained, but are to be augmented or enhanced in their content or production, and 4) cells in which it is desirable to change the pattern of regulation or induction of a gene encoding a protein.

Primary, secondary and immortalized cells to be transfected by the present method can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Where the homologously recombinant cells are to be used in gene therapy, primary cells are preferably obtained from the individual to whom the transfected primary or secondary cells are administered. However, primary cells can be obtained from a donor (other than the recipient) of the same species.

Homologously recombinant immortalized cells can also be produced by the present method and used for either protein production or gene therapy. Examples of immortalized human cell lines useful for protein production or gene therapy by the present method include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A. M. et al., Cancer Res, 48:5927–5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) may be used. In addition, primary, secondary, or immortalized human cells, as well as primary, secondary, or immortalized cells from other species which display the properties of gene amplification in vitro can be used for in vitro protein production or gene therapy.

Method of Converting a Gene into a cDNA Copy

The present invention also relates to a method by which homologous recombination is used to convert a gene into a cDNA copy (a gene copy devoid of introns). The cDNA copy can be transferred into yeast or bacteria for in vitro protein production, or the cDNA copy can be inserted into a mammalian cell for in vitro or in vivo protein production. If the cDNA is to be transferred to microbial cells, two DNA constructs containing targeting sequences are introduced by homologous recombination, one construct upstream of and one construct downstream of a human gene encoding a therapeutic protein. For example, the sequences introduced upstream include DNA sequences homologous to genomic DNA sequences at or upstream of the DNA encoding the first amino acid of a mature, processed therapeutic protein; a retroviral long term repeat (LTR); sequences encoding a marker for selection in microbial cells; a regulatory element that functions in microbial cells; and DNA encoding a leader peptide that promotes secretion from microbial cells with a splice-donor site. The sequences introduced upstream are introduced near to and upstream of genomic DNA encoding the first amino acid of a mature, processed therapeutic protein. The sequences introduced downstream include DNA sequences homologous to genomic DNA sequences at or downstream of the DNA encoding the last amino acid of a mature, processed protein; a microbial transcriptional termination sequence; sequences capable of directing DNA replication in microbial cells; and a retroviral LTR. The sequences introduced downstream are introduced adjacent to and downstream of the DNA encoding the stop codon of the mature, processed therapeutic protein. After the two DNA constructs are introduced into cells, the resulting cells are maintained under conditions appropriate for homologous recombination between the introduced DNA and genomic DNA, thereby producing homologously recombinant cells. Optionally, one or both of the DNA constructs can encode one or more markers for either positive or negative selection of cells containing the DNA construct, and a selection step can be added to the method after one or both of the DNA constructs have been introduced into the cells. Alternatively, the sequences encoding the marker for selection in microbial cells and the sequences capable of directing DNA replication in microbial cells can both be present in either the upstream or the downstream targeting construct, or the marker for selection in microbial cells can be present in the downstream targeting construct and the sequences capable of directing DNA replication in microbial cells can be present in the upstream targeting construct. The homologously recombinant cells are then cultured under conditions appropriate for LTR directed transcription, processing and reverse transcription of the RNA product of the gene encoding the therapeutic protein. The product of reverse transcription is a DNA construct comprising an intronless DNA copy encoding the therapeutic protein, operatively linked to DNA sequences comprising the two exogenous DNA constructs described above. The intronless DNA construct produced by the present method is then introduced into a microbial cell. The microbial cell is then cultured under conditions appropriate for expression and secretion of the therapeutic protein.

In Vivo Protein Production

Homologously recombinant cells of the present invention are useful, as populations of homologously recombinant cell lines, as populations of homologously recombinant primary or secondary cells, homologously recombinant clonal cell strains or lines, homologously recombinant heterogenous cell strains or lines, and as cell mixtures in which at least one representative cell of one of the four preceding categories of homologously recombinant cells is present. Such cells may be used in a delivery system for treating an individual with an abnormal or undesirable condition which responds to delivery of a therapeutic product, which is either: 1) a therapeutic protein (e.g., a protein which is absent, underproduced relative to the individual's physiologic needs, defective or inefficiently or inappropriately utilized in the individual; a protein with novel functions, such as enzymatic or transport functions) or 2) a therapeutic nucleic acid (e.g., RNA which inhibits gene expression or has intrinsic enzymatic activity). In the method of the present invention of providing a therapeutic protein or nucleic acid, homologously recombinant primary cells, clonal cell strains or heterogenous cell strains are administered to an individual in whom the abnormal or undesirable condition is to be treated or prevented, in sufficient quantity and by an appropriate route, to express or make available the protein or exogenous DNA at physiologically relevant levels. A physiologically relevant level is one which either approximates the level at which the product is normally produced in the body or results in improvement of the abnormal or undesirable condition. According to an embodiment of the invention described herein, the homologously recombinant immortalized cell lines to be administered can be enclosed in one or more semipermeable barrier devices. The permeability properties of the device are such that the cells are prevented from leaving the device upon implantation into an animal, but the therapeutic product is freely permeable and can leave the barrier device and enter the local space surrounding the implant or enter the systemic circulation. For example, hGH, hEPO, human insulinotropin, hGM-CSF, hG-CSF, human α-interferon, or human FSHβ can be delivered systemically in humans for therapeutic benefits.

Barrier devices are particularly useful and allow homologously recombinant immortalized cells, homologously recombinant cells from another species (homologously recombinant xenogeneic cells), or cells from a nonhistocompatibility-matched donor (homologously recombinant allogeneic cells) to be implanted for treatment of human or animal conditions or for agricultural uses (i.e., meat and dairy production). Barrier devices also allow convenient short-term (i.e., transient) therapy by providing ready access to the cells for removal when the treatment regimen is to be halted for any reason.

A number of synthetic, semisynthetic, or natural filtration membranes can be used for this purpose, including, but not limited to, cellulose, cellulose acetate, nitrocellulose, polysulfone, polyvinylidene difluoride, polyvinyl chloride polymers and polymers of polyvinyl chloride derivatives. Barrier devices can be utilized to allow primary, secondary, or immortalized cells from another species to be used for gene therapy in humans.

In Vitro Protein Production

Homologously recombinant cells from human or non-human species according to this invention can also be used for in vitro protein production. The cells are maintained under conditions, as are known in the art, which result in expression of the protein. Proteins expressed using the methods described may be purified from cell lysates or cell supernatants in order to purify the desired protein. Proteins made according to this method include therapeutic proteins which can be delivered to a human or non-human animal by conventional pharmaceutical routes as is known in the art (e.g., oral, intravenous, intramuscular, intranasal or subcutaneous). Such proteins include hGH, hEPO, and human insulinotropin, hGM-CSF, hG-CSF, FSHβ or α-interferon. These cells can be immortalized, primary, or secondary cells. The use of cells from other species may be desirable in cases where the non-human cells are advantageous for protein production purposes where the non-human protein is therapeutically or commercially useful, for example, the use of cells derived from salmon for the production of salmon calcitonin, the use of cells derived from pigs for the production of porcine insulin, and the use of bovine cells for the production of bovine growth hormone.

Advantages

The methodologies, DNA constructs, cells, and resulting proteins of the invention herein possess versatility and many other advantages over processes currently employed within the art in gene targeting. The ability to activate an endogenous gene by positioning an exogenous regulatory sequence at various positions ranging from immediately adjacent to the gene of interest (directly fused to the normal gene's transcribed region) to 30 kilobase pairs or further upstream of the transcribed region of an endogenous gene, or within an intron of an endogenous gene, is advantageous for gene expression in cells. For example, it can be employed to position the regulatory element upstream or downstream of regions that normally silence or negatively regulate a gene. The positioning of a regulatory element upstream or downstream of such a region can override such dominant negative effects that normally inhibit transcription. In addition, regions of DNA that normally inhibit transcription or have an otherwise detrimental effect on the expression of a gene may be deleted using the targeting constructs, described herein.

Additionally, since promoter function is known to depend strongly on the local environment, a wide range of positions may be explored in order to find those local environments optimal for function. However, since, ATG start codons are found frequently within mammalian DNA (approximately one occurrence per 48 base pairs), transcription cannot simply initiate at any position upstream of a gene and produce a transcript containing a long leader sequence preceding the correct ATG start codon, since the frequent occurrence of ATG codons in such a leader sequence will prevent translation of the correct gene product and render the message useless. Thus, the incorporation of an exogenous exon, a splice-donor site, and, optionally, an intron and a splice-acceptor site into targeting constructs comprising a regulatory region allows gene expression to be optimized by identifying the optimal site for regulatory region function, without the limitation imposed by needing to avoid inappropriate ATG start codons in the mRNA produced. This provides significantly increased flexibility in the placement of the construct and makes it possible to activate a wider range of genes. The DNA constructs of the present invention are also useful, for example, in processes for making fusion proteins encoded by recombinant, or exogenous, sequences and endogenous sequences.

Gene targeting and amplification as disclosed above are particularly useful for altering on the expression of genes which form transcription units which are sufficiently large that they are difficult to isolate and express, or for turning on genes for which the entire protein coding region is unavailable or has not been cloned. Thus, the DNA constructs described above are useful for operatively linking exogenous regulatory elements to endogenous genes in a way that precisely defines the transcriptional unit, provides flexibility in the relative positioning of exogeneous regulatory elements and endogenous genes ultimately, enables a highly controlled system for obtaining and regulating expression of genes of therapeutic interest.

Explanation of the Examples

As described herein, Applicants have demonstrated that DNA can be introduced into cells, such as primary, secondary or immortalized vertebrate cells and integrated into the genome of the transfected cells by homologous recombination. They have further demonstrated that the exogenous DNA has the desired function in the homologously recombinant (HR) cells and that correctly targeted cells can be identified on the basis of a detectable phenotype conferred by the properly targeted DNA.

Applicants describe construction of a plasmid useful for targeting to a particular locus (the HPRT locus) in the human genome and selection based upon a drug resistant phenotype (Example 1a). This plasmid is designated pE3Neo and its integration into the cellular genome at the HPRT locus produces cells which have an hprt$^-$, 6-TG resistant phenotype and are also G418 resistant. As described, they have shown that pE3Neo functions properly in gene targeting in an established human fibroblast cell line (Example 1b), by demonstrating localization of the DNA introduced into established cells within exon 3 of the HPRT gene.

In addition, Applicants demonstrate gene targeting in primary and secondary human skin fibroblasts using pE3Neo (Example 1c). The subject application further demonstrates that modification of DNA termini enhances targeting of DNA into genomic DNA (Examples 1c and 1e). Applicants also describe methods by which a gene can be inserted at a preselected site in the genome of a cell, such as a primary, secondary, or immortalized cell by gene targeting (Example 1d).

In addition, the present invention relates to a method of protein production using transfected cells. The method involves transfecting cells, such as primary cells, secondary cells or immortalized cells, with exogenous DNA which encodes a therapeutic product or with DNA which is sufficient to target to an endogenous gene which encodes a therapeutic product. For example, Examples 1g, 1h, 1j, 1k, 2, 3, 4 and 6–9 describe protein production by targeting of a selected endogenous gene with DNA sequence elements which will alter the expression of the endogenous gene.

Applicants also describe DNA constructs and methods for amplifying an endogenous cellular gene that has been activated by gene targeting (Examples 3, 6, 8 and 9).

Examples 1f–1h, 2, 4 and 6 illustrate embodiments in which the normal regulatory sequences upstream of the human EPO gene are altered to allow expression of hEPO in primary or secondary fibroblast strains which do not express EPO in detectable quantities in their untransfected state. In one embodiment the product of targeting leaves the normal EPO protein intact, but under the control of the mouse metallothionein promoter. Examples 1i and 1j demonstrate the use of similar targeting constructs to activate the endogenous growth hormone gene in primary or secondary human fibroblasts. In other embodiments described for activating EPO expression in human fibroblasts, the products of targeting events are chimeric transcription units, in which the first exon of the human growth hormone gene is positioned upstream of EPO exons 2–5. The product of transcription (controlled by the mouse metallothionein promoter), splicing, and translation is a protein in which amino acids 1–4 of the hEPO signal peptide are replaced with amino acid residues 1–3 of hGH. The chimeric portion of this protein, the signal peptide, is removed prior to secretion from cells. Example 5 describes targeting constructs and methods for producing cells which will convert a gene (with introns) into an expressible cDNA copy of that gene (without introns) and the recovery of such expressible cDNA molecules in microbial (e.g., yeast or bacterial) cells. Example 6 describes construction of a targeting vector, designated pREPO4 for dual selection and selection of cells in which the dhfr gene is amplified. Plasmid pREPO4 has been used to amplify the human EPO (hEPO) locus in HT1080 cells (an immortalized human cell line) after activation of the endogenous hEPO gene by homologous recombination. As described, stepwise selection in methotrexate-containing media resulted in a 70-fold increase in hEPO production in cells resistant to 0.4 μM methotrexate.

Examples 7 and 8 describe methods for inserting a regulatory sequence upstream of the normal EPO promoter and methods for EPO production using such a construct. In addition, Example 8 describes the amplification of a targeted EPO gene produced by the method of Example 7. Example 9 describes methods for targeting the human α-interferon, GM-CSF, G-CSF, and FSHβ genes to create cells useful for in protein production.

Figure 5:
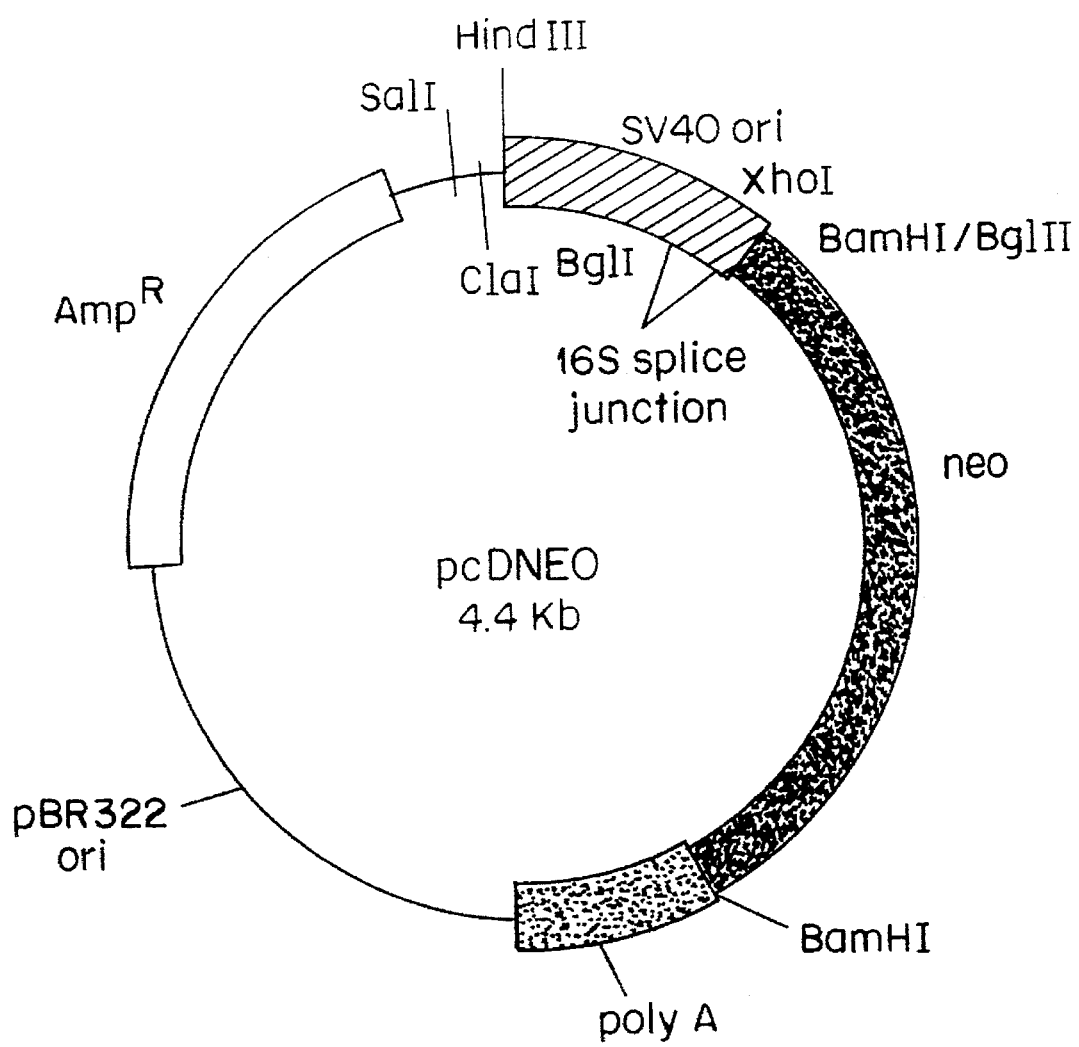
FIG. 5 is a schematic representation of plasmid pcDNEO, which includes the neo coding region (BamHI-BglII fragment) from plasmid pSV2neo inserted into the BamHI site of plasmid pcD; the Amp-R and pBR322Ori sequences from pBR322; and the polyA, 16S splice junctions and early promoter regions from SV40.
Figure 6:
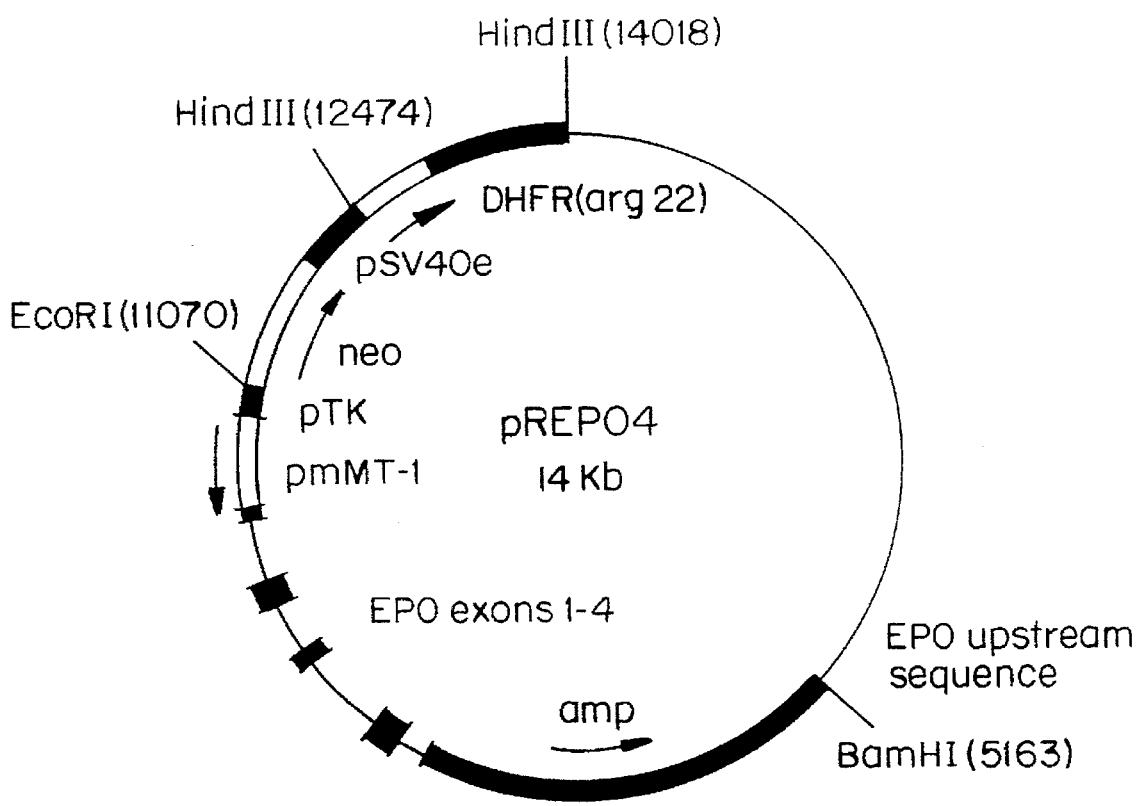
FIG. 6 is a schematic representation of plasmid pREPO4.

The Examples provide methods for activating or for activating and amplifying endogenous genes by gene targeting which do not require manipulation or other uses of the target genes' protein coding regions. Using the methods and DNA constructs or plasmids taught herein or modifications thereof which are apparent to one of ordinary skill in the art, gene expression can be altered in cells that have properties desirable for in vitro protein production (e.g., pharmaceutics) or in vivo protein delivery methods (e.g. gene therapy). FIGS. 5 and 6 illustrate two strategies for transcriptionally activating the hEPO gene.

Using the methods and DNA constructs or plasmids taught herein or modifications thereof which are apparent to one of ordinary skill in the art, exogenous DNA which encodes a therapeutic product (e.g., protein, ribozyme, antisense RNA) can be inserted at preselected sites in the genome of vertebrate (e.g., mammalian, both human and nonhuman) primary or secondary cells.

The present invention will now be illustrated by the following examples, which are not intended to be limiting in any way.

EXAMPLES

Example 1. PRODUCTION OF TRANSFECTED CELL STRAINS BY GENE TARGETING

Gene targeting occurs when transfecting DNA either integrates into or partially replaces chromosomal DNA sequences through a homologous recombinant event. While such events can occur in the course of any given transfection experiment, they are usually masked by a vast excess of events in which plasmid DNA integrates by nonhomologous, or illegitimate, recombination.

a. GENERATION OF A CONSTRUCT USEFUL FOR SELECTION OF GENE TARGETING EVENTS IN HUMAN CELLS

One approach to selecting the targeted events is by genetic selection for the loss of a gene function due to the integration of transfecting DNA. The human HPRT locus encodes the enzyme hypoxanthine-phosphoribosyl transferase. hprt$^-$ cells can be selected for by growth in medium containing the nucleoside analog 6-thioguanine (6-TG): cells with the wild-type (HPRT+) allele are killed by 6-TG, while cells with mutant (hprt$^-$) alleles can survive. Cells harboring targeted events which disrupt HPRT gene function are therefore selectable in 6-TG medium.

To construct a plasmid for targeting to the HPRT locus, the 6.9 kb HindIII fragment extending from positions 11,960–18,869 in the HPRT sequence (Genebank name HUMHPRTB; Edwards, A. et al., *Genomics* 6:593–608 (1990)) and including exons 2 and 3 of the HPRT gene, is subcloned into the HindIII site of pUC12. The resulting clone is cleaved at the unique XhoI site in exon 3 of the HPRT gene fragment and the 1.1 kb SalI-XhoI fragment containing the neo gene from pMC1Neo (Stratagene) is inserted, disrupting the coding sequence of exon 3. One orientation, with the direction of neo transcription opposite that of HPRT transcription was chosen and designated pE3Neo. The replacement of the normal HPRT exon 3 with the neo-disrupted version will result in an hprt$^-$, 6-TG resistant phenotype. Such cells will also be G418 resistant.

b. GENE TARGETING IN AN ESTABLISHED HUMAN FIBROBLAST CELL LINE

As a demonstration of targeting in immortalized cell lines, and to establish that pE3Neo functions properly in gene targeting, the human fibrosarcoma cell line HT1080 (ATCC CCL 121) was transfected with pE3Neo by electroporation.

HT1080 cells were maintained in HAT (hypoxanthine/aminopterin/xanthine) supplemented DMEM with 15% calf serum (Hyclone) prior to electroporation. Two days before electroporation, the cells are switched to the same medium without aminopterin. Exponentially growing cells were trypsinized and diluted in DMEM/15% calf serum, centrifuged, and resuspended in PBS (phosphate buffered saline) at a final cell volume of 13.3 million cells per ml. pE3Neo is digested with HindIII, separating the 8 kb HPRT-neo fragment from the pUC12 backbone, purified by phenol extraction and ethanol precipitation, and resuspended at a concentration of 600 μg/ml. 50 μl (30 μg) was added to the electroporation cuvette (0.4 cm electrode gap; Bio-Rad Laboratories), along with 750 μl of the cell suspension (10 million cells). Electroporation was at 450 volts, 250 μFarads (Bio-Rad Gene Pulser; Bio-Rad Laboratories). The contents of the cuvette were immediately added to DMEM with 15% calf serum to yield a cell suspension of 1 million cells per 25 ml media. 25 ml of the treated cell suspension was plated onto 150 mm diameter tissue culture dishes and incubated at 37° C., 5% $CO_2$. 24 hrs later, a G418 solution was added directly to the plates to yield a final concentration of 800 μg/ml G418. Five days later the media was replaced with DMEM/15% calf serum/ 800 μg/ml G418. Nine days after electroporation, the media was replaced with DMEM/15% calf serum/800 μg/ml G418 and 10 μM 6-thioguanine. Colonies resistant to G418 and 6-TG were picked using cloning cylinders 14–16 days after the dual selection was initiated.

The results of five representative targeting experiments in HT1080 cells are shown in Table 1.

TABLE 1

| Transfection | Number of Treated Cells | Number of G418$^r$ 6-TG$^r$ Clones |
|---|---|---|
| 1 | 1 × 10$^7$ | 32 |
| 2 | 1 × 10$^7$ | 28 |
| 3 | 1 × 10$^7$ | 24 |
| 4 | 1 × 10$^7$ | 32 |
| 5 | 1 × 10$^7$ | 66 |

For transfection 5, control plates designed to determine the overall yield of G418® colonies indicated that 33,700 G418® colonies could be generated from the initial 1×10$^7$ treated cells. Thus, the ratio of targeted to non-targeted events is 66/33,700, or 1 to 510. In the five experiments combined, targeted events arise at a frequency of 3.6×10$^6$, or 0.00036% of treated cells.

Restriction enzyme and Southern hybridization experiments using probes derived from the neo and HPRT genes localized the neo gene to the HPRT locus at the predicted site within HPRT exon 3.

c. GENE TARGETING IN PRIMARY AND SECONDARY HUMAN SKIN FIBROBLASTS pE3Neo is digested with HindIII, separating the 8 kb HPRT-neo fragment from the pUC12 backbone, and purified by phenol extraction and ethanol precipitation. DNA was resuspended at 2 mg/ml. Three million secondary human foreskin fibroblasts cells in a volume of 0.5 ml were electroporated at 250 volts and 960 µFarads, with 100 µg of HindIII pE3Neo (50 µl). Three separate transfections were performed, for a total of 9 million treated cells. Cells are processed and selected for G418 resistance. 500,000 cells per 150 mm culture dish were plated for G418 selection. After 10 days under selection, the culture medium is replaced with human fibroblast nutrient medium containing 400 µg/ml G418 and 10 µM 6-TG. Selection with the two drug combination is continued for 10 additional days. Plates are scanned microscopically to localize human fibroblast colonies resistant to both drugs. The fraction of G418® t-TG® colonies is 4 per 9 million treated cells. These colonies constitute 0.0001% (or 1 in a million) of all cells capable of forming colonies. Control plates designed to determine the overall yield of G418® colonies indicated that 2,850 G418® colonies could be generated from the initial $9\times10^6$ treated cells. Thus, the ratio of targeted to non-targeted events is 4/2,850, or 1 to 712. Restriction enzyme and Southern hybridization experiments using probes derived from the neo and HPRT genes were used to localize the neo gene to the HPRT locus at the predicted site within HPRT exon 3 and demonstrate that targeting had occurred in these four clonal cell strains. Colonies resistant to both drugs have also been isolated by transfecting primary cells ($1/3.0\times 10^7$).

The results of several pE3Neo targeting experiments are summarized in Table 2. HindIII digested pE3Neo was either transfected directly or treated with exonuclease III to generate 5' single-stranded overhangs prior to transfection (see Example 1c). DNA preparations with single-stranded regions ranging from 175 to 930 base pairs in length were tested. Using pE3neo digested with HindIII alone, 1/799 G418-resistant colonies were identified by restriction enzyme and Southern hybridization analysis as having a targeted insertion of the neo gene at the HPRT locus (a total of 24 targeted clones were isolated). Targeting was maximally stimulated (approximately 10-fold stimulation) when overhangs of 175 bp were used, with 1/80 G418® colonies displaying restriction fragments that are diagnostic for targeting at HPRT (a total of 9 targeted clones were isolated). Thus, using the conditions and recombinant DNA constructs described here, targeting is readily observed in normal human fibroblasts and the overall targeting frequency (the number of targeted clones divided by the total number of clones stably transfected to G418-resistance) can be stimulated by transfection with targeting constructs containing single-stranded overhanging tails, by the method as described in Example 1e.

TABLE 2

TARGETING TO THE HPRT LOCUS IN HUMAN FIBROBLASTS

| pE3neo Treatment | Number of Experiments | Number Targeted Per G418$^r$ Colony | Total Number of Targeted Clone |
|---|---|---|---|
| HindIII digest | 6 | 1/799 | 24 |
| 175 bp overhang | 1 | 1/80 | 9 |
| 350 bp overhang | 3 | 1/117 | 20 |
| 930 bp overhang | 1 | 1/144 | 1 | d. GENERATION OF A CONSTRUCT FOR TARGETED INSERTION OF A GENE OF THERAPEUTIC INTEREST INTO THE HUMAN GENOME AND ITS USE IN GENE TARGETING

Figure 3:
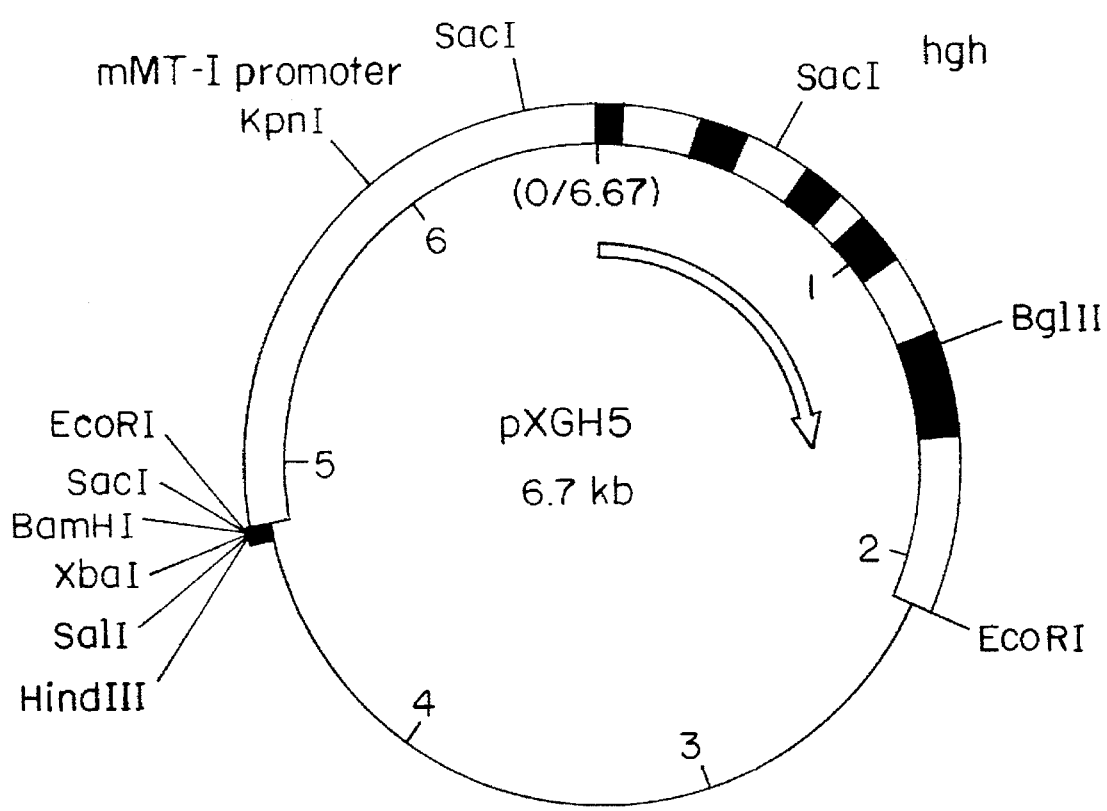
FIG. 3 is a schematic representation of plasmid pXGH5, which includes the hGH gene under the control of the mouse metallothionein promoter.

A variant of pE3Neo, in which a gene of therapeutic interest is inserted within the HPRT coding region, adjacent to or near the neo gene, can be used to target a gene of therapeutic interest to a specific position in a recipient primary or secondary cell genome. Such a variant of pE3Neo can be constructed for targeting the hGH gene to the HPRT locus.

pXGH5 (schematically presented in FIG. 3) is digested with EcoRI and the 4.1 kb fragment containing the hGH gene and linked mouse metallothionein (mMT) promoter is isolated. The EcoRI overhangs are filled in with the Klenow fragment from *E. coli* DNA polymerase. Separately, pE3Neo is digested with XhoI, which cuts at the junction of the neo fragment and HPRT exon 3 (the 3' junction of the insertion into exon 3). The XhoI overhanging ends of the linearized plasmid are filled in with the Klenow fragment from *E. coli* DNA polymerase, and the resulting fragment is ligated to the 4.1 kb blunt-ended hGH-mMT fragment. Bacterial colonies derived from the ligation mixture are screened by restriction enzyme analysis for a single copy insertion of the hGH-mMT fragment and one orientation, the hGH gene transcribed in the same direction as the neo gene, is chosen and designated pE3Neo/hGH. pE3Neo/hGH is digested with HindIII, releasing the 12.1 kb fragment containing HPRT, neo and mMT-hGH sequences. Digested DNA is treated and transfected into primary or secondary human fibroblasts as described in Example 1c. G418® TG® colonies are selected and analyzed for targeted insertion of the mMT-hGH and neo sequences into the HPRT gene as described in Example 1c. Individual colonies are assayed for hGH expression using a commercially available immunoassay (Nichols Institute).

Secondary human fibroblasts were transfected with pE3Neo/hGH and thioguanine-resistant colonies were analyzed for stable hGH expression and by restriction enzyme and Southern hybridization analysis. Of thirteen TG® colonies analyzed, eight colonies were identified with an insertion of the hGH gene into the endogenous HPRT locus. All eight strains stably expressed significant quantities of hGH, with an average expression level of 22.7 µg/$10^6$ cells/24 hours. Alternatively, plasmid pE3neoEPO, FIG. 4, may be used to target EPO to the human HPRT locus.

The use of homologous recombination to target a gene of therapeutic interest to a specific position in a cell's genomic DNA can be expanded upon and made more useful for producing products for therapeutic purposes (e.g., pharmaceutics, gene therapy) by the insertion of a gene through which cells containing amplified copies of the gene can be selected for by exposure of the cells to an appropriate drug selection regimen. For example, pE3neo/hGH (Example 1d) can be modified by inserting the dhfr, ada, or CAD gene at a position immediately adjacent to the hGH or neo genes in pE3neo/hGH. Primary, secondary, or immortalized cells are transfected with such a plasmid and correctly targeted events are identified. These cells are further treated with increasing concentrations of drugs appropriate for the selection of cells containing amplified genes (for dhfr, the selective agent is methotrexate, for CAD the selective agent is N-(phosphonacetyl)-L-aspartate (PALA), and for ada the selective agent is an adenine nucleoside (e.g., alanosine). In this manner the integration of the gene of therapeutic interest will be coamplified along with the gene for which amplified copies are selected. Thus, the genetic engineering of cells to produce genes for therapeutic uses can be readily controlled by preselecting the site at which the targeting construct integrates and at which the amplified copies reside in the amplified cells.

e. MODIFICATION OF DNA TERMINI TO ENHANCE TARGETING

Several lines of evidence suggest that 3'-overhanging ends are involved in certain homologous recombination pathways of E. coli, bacteriophage, S. cerevisiae and Xenopus laevis. In Xenopus laevis oocytes, molecules with 3'-overhanging ends of several hundred base pairs in length underwent recombination with similarly treated molecules much more rapidly after microinjection than molecules with very short overhangs (4 bp) generated by restriction enzyme digestion. In yeast, the generation of 3'-overhanging ends several hundred base pairs in length appears to be a rate limiting step in meiotic recombination. No evidence for an involvement of 3'-overhanging ends in recombination in human cells has been reported, and in no case have modified DNA substrates of any sort been shown to promote targeting (one form of homologous recombination) in any species. The experiment described in the following example and Example 1c suggests that 5'-overhanging ends are effective for stimulating targeting in primary, secondary and immortalized human fibroblasts.

There have been no reports on the enhancement of targeting by modifying the ends of the transfecting DNA molecules. This example serves to illustrate that modification of the ends of linear DNA molecules, by conversion of the molecules' termini from a double-stranded form to a single-stranded form, can stimulate targeting into the genome of primary and secondary human fibroblasts.

1100 µg of plasmid pE3Neo (Example 1a) is digested with HindIII. This DNA can be used directly after phenol extraction and ethanol precipitation, or the 8 kb HindIII fragment containing only HPRT and the neo gene can be separated away from the pUC12 vector sequences by gel electrophoresis. ExoIII digestion of the HindIII digested DNA results in extensive exonucleolytic digestion at each end, initiating at each free 3' end, and leaving 5'-overhanging ends. The extent of exonucleolytic action and, hence, the length of the resulting 5'-overhangs, can be controlled by varying the time of ExoIII digestion. ExoIII digestion of 100 µg of HindIII digested pE3Neo is carried out according to the supplier's recommended conditions, for times of 30 sec, 1 min, 1.5 min, 2 min, 2.5 min, 3 min, 3.5 min, 4 min, 4.5 min, and 5 min. To monitor the extent of digestion an aliquot from each time point, containing 1 µg of ExoIII treated DNA, is treated with mung bean nuclease (Promega), under conditions recommended by the supplier, and the samples fractionated by gel electrophoresis. The difference in size between nontreated, HindIII digested pE3Neo and the same molecules treated with ExoIII and mung bean nuclease is measured. This size difference divided by two gives the average length of the 5'-overhang at each end of the molecule. Using the time points described above and digestion at 30°, the 5'-overhangs produced should range from 100 to 1,000 bases.

60 µg of ExoIII treated DNA (total HindIII digest of pE3Neo) from each time point is purified and electroporated into primary, secondary, or immortalized human fibroblasts under the conditions described in Example 1c. The degree to which targeting is enhanced by each ExoIII treated preparation is quantified by counting the number of G418® 6-TG® colonies and comparing these numbers to targeting with HindIII digested pE3Neo that was not treated with ExoIII.

The effect of 3'-overhanging ends can also be quantified using an analogous system. In this case HindIII digested pE3Neo is treated with bacteriophage T7 gene 6 exonuclease (United States Biochemicals) for varying time intervals under the supplier's recommended conditions. Determination of the extent of digestion (average length of 3'-overhang produced per end) and electroporation conditions are as described for ExoIII treated DNA. The degree to which targeting is enhanced by each T7 gene 6 exonuclease treated preparation is quantified by counting the number of G418® 6-TG® colonies and comparing these numbers to targeting with HindIII digested pE3Neo that was not treated with T7 gene 6 exonuclease.

Other methods for generating 5' and 3' overhanging ends are possible, for example, denaturation and annealing of two linear molecules that partially overlap with each other will generate a mixture of molecules, each molecule having 3'-overhangs at both ends or 5'-overhangs at both ends, as well as reannealed fragments indistinguishable from the starting linear molecules. The length of the overhangs is determined by the length of DNA that is not in common between the two DNA fragments.

f. CONSTRUCTION OF TARGETING PLASMIDS FOR PLACING THE HUMAN ERYTHROPOIETIN GENE UNDER THE CONTROL OF THE MOUSE METALLOTHIONEIN PROMOTER IN PRIMARY, SECONDARY AND IMMORTALIZED HUMAN FIBROBLASTS

The following serves to illustrate one embodiment of the present invention, in which the normal positive and negative regulatory sequences upstream of the human erythropoietin (hEPO) gene are altered to allow expression of human erythropoietin in primary, secondary or immortalized human fibroblasts, which do not express hEPO in significant quantities as obtained.

A region lying exclusively upstream of the human EPO coding region can be amplified by PCR. Three sets of primers useful for this purpose were designed after analysis of the published human EPO sequence [Genbank designation HUMERPA; Lin, F-K., et al., *Proc. Natl. Acad. Sci., USA* 82:7580–7584 (1985)]. These primer pairs can amplify fragments of 609, 603, or 590 bp.

TABLE 3

| Primer | HUMERPA Coordinate | Sequence | Fragment Size |
|---|---|---|---|
| F1 | 2 → 20 | 5' AGCTTCTGGGCTTCCAGAC (SEQ ID NO 1) | |
| R2 | 610 → 595 | 5' GGGGTCCCTCAGCGAC (SEQ ID NO 2) | 609 bp |
| F2 | 8 → 24 | 5' TGGGCTTCCAGACCCAG (SEQ ID NO 3) | |
| R2 | 610 → 595 | 5' GGGGTCCCTCAGCGAC | 603 bp |
| F3 | 21 → 40 | 5' CCAGCTACTTTGCGGAACTC (SEQ ID NO 4) | |
| R2 | 610 → 595 | 5' GGGGTCCCTCAGCGAC (SEQ ID NO 2) | 590 bp |

The three fragments overlap substantially and are interchangeable for the present purposes. The 609 bp fragment, extending from −623 to −14 relative to the translation start site (HUMERPA nucleotide positions 2 to 610), is ligated at both ends with ClaI linkers. The resulting ClaI-linked fragment is digested with ClaI and inserted into the ClaI site of pBluescriptIISK/+ (Stratagene), with the orientation such that HUMERPA nucleotide position 610 is adjacent to the SalI site in the plasmid polylinker). This plasmid, p5'EPO, can be cleaved, separately, at the unique FspI or SfiI sites in the human EPO upstream fragment (HUMERPA nucleotide positions 150 and 405, respectively) and ligated to the mouse metallothionein promoter. Typically, the 1.8 kb EcoRI-BglII from the mMT-I gene [containing no mMT coding sequences; Hamer, D. H. and Walling M., J. Mol. Appl. Gen. 1:273 288 (1982); this fragment can also be isolated by known methods from mouse genomic DNA using PCR primers designed from analysis of mMT sequences available from Genbank; i.e., MUSMTI, MUSMTIP, MUSMTIPRM] is made blunt-ended by known methods and ligated with SfiI digested (also made blunt-ended) or FspI digested p5'EPO. The orientations of resulting clones are analyzed and those in which the former mMT BglII site is proximal to the SalI site in the plasmid polylinker are used for targeting primary and secondary human fibroblasts. This orientation directs mMT transcription towards HUMERPA nucleotide position 610 in the final construct. The resulting plasmids are designated p5'EPO-mMTF and p5'EPO-mMTS for the mMT insertions in the FspI and SfiI sites, respectively.

Additional upstream sequences are useful in cases where it is desirable to modify, delete and/or replace negative regulatory elements or enhancers that lie upstream of the initial target sequence. In the case of EPO, a negative regulatory element that inhibits EPO expression in extrahepatic and extrarenal tissues [Semenza, G. L. et al., Mol. Cell. Biol. 10:930–938 (1990)] can be deleted. A series of deletions within the 6 kb fragment are prepared. The deleted regions can be replaced with an enhancer with broad host-cell activity [e.g. an enhancer from the Cytomegalovirus (CMV)].

The orientation of the 609 bp 5'EPO fragment in the pBluescriptIISK/+ vector was chosen since the HUMERPA sequences are preceded on their 5' end by a BamHI (distal) and HindIII site (proximal). Thus, a 6 kb BamHI-HindIII fragment normally lying upstream of the 609 bp fragment [Semenza, G. L. et al., Mol. Cell. Biol. 10:930–938 (1990)] can be isolated from genomic DNA by known methods. For example, a bacteriophage, cosmid, or yeast artificial chromosome library could be screened with the 609 bp PCR amplified fragment as a probe. The desired clone will have a 6 kb BamHI-HindIII fragment and its identity can be confirmed by comparing its restriction map from a restriction map around the human EPO gene determined by known methods. Alternatively, constructing a restriction map of the human genome upstream of the EPO gene using the 609 bp fragment as a probe can identify enzymes which generate a fragment originating between HUMERPA coordinates 2 and 609 and extending past the upstream BamHI site; this fragment can be isolated by gel electrophoresis from the appropriate digest of human genomic DNA and ligated into a bacterial or yeast cloning vector. The correct clone will hybridize to the 609 bp 5'EPO probe and contain a 6 kb BamHI-HindIII fragment. The isolated 6 kb fragment is inserted in the proper orientation into p5'EPO, p5'EPO-mMTF, or p5'EPO-mMTS (such that the HindIII site is adjacent to HUMERPA nucleotide position 2). Additional upstream sequences can be isolated by known methods, using chromosome walking techniques or by isolation of yeast artificial chromosomes hybridizing to the 609 bp 5'EPO probe.

The cloning strategies described above allow sequences upstream of EPO to be modified in vitro for subsequent targeted transfection of primary, secondary or immortalized human fibroblasts. The strategies describe simple insertions of the mMT promoter, as well as deletion of the negative regulatory region, and deletion of the negative regulatory region and replacement with an enhancer with broad host-cell activity.

g. ACTIVATING THE HUMAN EPO GENE AND ISOLATION OF TARGETED PRIMARY, SECONDARY AND IMMORTALIZED HUMAN FIBROBLASTS BY SCREENING

For targeting, the plasmids are cut with restriction enzymes that free the insert away from the plasmid backbone. In the case of p5'EPO-mMTS, HindIII and SalII digestion releases a targeting fragment of 2.4 kb, comprised of the 1.8 kb mMT promoter flanked on the 5' and 3' sides by 405 bp and 204 base pairs, respectively, of DNA for targeting this construct to the regulatory region of the human EPO gene. This DNA or the 2.4 kb targeting fragment alone is purified by phenol extraction and ethanol precipitation and transfected into primary or secondary human fibroblasts under the conditions described in Example 1c. Transfected cells are plated onto 150 mm dishes in human fibroblast nutrient medium. 48 hours later the cells are plated into 24 well dishes at a density of 10,000 cells/cm$^2$ [approximately 20,000 cells per well; if targeting occurs at a rate of 1 event per $10^6$ clonable cells (Example 1c, then about 50 wells would need to be assayed to isolate a single expressing colony]. Cells in which the transfecting DNA has targeted to the homologous region upstream of the human EPO gene will express hEPO under the control of the mMT promoter. After 10 days, whole well supernatants are assayed for EPO expression using a commercially available immunoassay kit (Amgen). Clones from wells displaying hEPO synthesis are isolated using known methods, typically by assaying fractions of the heterogenous populations of cells separated into individual wells or plates, assaying fractions of these positive wells, and repeating as needed, ultimately isolating the targeted colony by screening 96-well microtiter plates seeded at one cell per well. DNA from entire plate lysates can also be analyzed by PCR for amplification of a fragment using a mMT specific primer in conjunction with a primer lying upstream of HUMERPA nucleotide position 1. This primer pair should amplify a DNA fragment of a size precisely predicted based on the DNA sequence. Positive plates are trypsinized and replated at successively lower dilutions, and the DNA preparation and PCR steps repeated as needed to isolate targeted cells.

The targeting schemes herein described can also be used to activate hGH expression in immortalized human cells (for example, HT1080 cells (ATCC CCL 121), HeLa cells and derivatives of HeLa cells (ATCC CCL2, 2.1 and 2.2), MCF-7 breast cancer cells (ATCC HBT 22), K-562 leukemia cells (ATCC CCL 232), KB carcinoma cells (ATCC CCL 17), 2780AD ovarian carcinoma cells (Van der Blick, A. M. et al., Cancer Res, 48:5927–5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), MOLT-4 cells (ATCC CRL 1582), and varous heterohybridoma cells) for the purposes of producing hGH for conventional pharmaceutic delivery.

h. ACTIVATING THE HUMAN EPO GENE AND ISOLATION OF TARGETED PRIMARY, SECONDARY AND IMMORTALIZED HUMAN FIBROBLASTS BY A POSITIVE OR A COMBINED POSITIVE/NEGATIVE SELECTION SYSTEM

The strategy for constructing p5'EPO-mMTF, p5'EPO-mMTS, and derivatives of such with the additional upstream 6 kb BamHI-HindIII fragment can be followed with the additional step of inserting the neo gene adjacent to the mMT promoter. In addition, a negative selection marker, for example, gpt [from pMSG (Pharmacia) or another suitable source], can be inserted adjacent to the HUMERPA sequences in the pBluescriptIISK/+ polylinker. In the former case, G418® colonies are isolated and screened by PCR amplification or restriction enzyme and Southern hybridization analysis of DNA prepared from pools of colonies to identify targeted colonies. In the latter case, G418® colonies are placed in medium containing 6-thioxanthine to select against the integration of the gpt gene [Besnard, C. et al., Mol. Cell. Biol. 7:4139–4141 (1987)]. In addition, the HSV-TK gene can be placed on the opposite side of the insert as gpt, allowing selection for neo and against both gpt and TK by growing cells in human fibroblast nutrient medium containing 400 µg/ml G418, 100 µM 6-thioxanthine, and 25 µg/ml gancyclovir. The double negative selection should provide a nearly absolute selection for true targeted events and Southern blot analysis provides an ultimate confirmation.

The targeting schemes herein described can also be used to activate hEPO expression in immortalized human cells (for example, HT1080 cells (ATCC CCL 121), HeLa cells and derivatives of HeLa cells (ATCC CCL2, 2.1 and 2.2), MCF-7 breast cancer cells (ATCC HBT 22), K-562 leukemia cells (ATCC CCL 232), KB carcinoma cells (ATCC CCL 17), 2780AD ovarian carcinoma cells (Van der Blick, A. M. et al., Cancer Res, 48:5927–5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), MOLT-4 cells (ATCC CRL 1582), and various heterohybridoma cells) for the purposes of producing hEPO for conventional pharmaceutic delivery.

i. CONSTRUCTION OF TARGETING PLASMIDS FOR PLACING THE HUMAN GROWTH HORMONE GENE UNDER THE CONTROL OF THE MOUSE METALLOTHIONEIN PROMOTER IN PRIMARY, SECONDARY OR IMMORTALIZED HUMAN FIBROBLASTS

The following example serves to illustrate one embodiment of the present invention, in which the normal regulatory sequences upstream of the human growth hormone gene are altered to allow expression of human growth hormone in primary, secondary or immortalized human fibroblasts.

Targeting molecules similar to those described in Example 1f for targeting to the EPO gene regulatory region are generated using cloned DNA fragments derived from the 5' end of the human growth hormone N gene. An approximately 1.8 kb fragment spanning HUMGHCSA (Genbank Entry) nucleotide positions 3787–5432 (the positions of two EcoNI sites which generate a convenient sized fragment for cloning or for diagnostic digestion of subclones involving this fragment) is amplified by PCR primers designed by analysis of the HUMGHCSA sequence in this region. This region extends from the middle of hGH gene N intron 1 to an upstream position approximately 1.4 kb 5' to the translational start site. pUC12 is digested with EcoRI and BamHI, treated with Klenow to generate blunt ends, and recircularized under dilute conditions, resulting in plasmids which have lost the EcoRI and BamHI sites. This plasmid is designated pUC12XEB. HindIII linkers are ligated onto the amplified hGH fragment and the resulting fragment is digested with HindIII and ligated to HindIII digested pUC12XEB. The resulting plasmid, pUC12XEB-5'hGH, is digested with EcoRI and BamHI, to remove a 0.5 kb fragment lying immediately upstream of the hGH transcriptional initiation site. The digested DNA is ligated to the 1.8 kb EcoRI-BglII from the mMT-I gene [containing no mMT coding sequences; Hamer, D. H. and Walling, M., J. Mol. Appl. Gen. 1:273–288 (1982); the fragment can also be isolated by known methods from mouse genomic DNA using PCR primers designed from analysis of mMT sequences available from Genbank; i.e., MUSMTI, MUSMTIP, MUSMTIPRM]. This plasmid p5'hGH-mMT has the mMT promoter flanked on both sides by upstream hGH sequences.

The cloning strategies described above allow sequences upstream of hGH to be modified in vitro for subsequent targeted transfection of primary, secondary or immortalized human fibroblasts. The strategy described a simple insertion of the mMT promoter. Other strategies can be envisioned, for example, in which an enhancer with broad host-cell specificity is inserted upstream of the inserted mMT sequence.

j. ACTIVATING THE HUMAN hGH GENE AND ISOLATION OF TARGETED PRIMARY, SECONDARY AND IMMORTALIZED HUMAN FIBROBLASTS BY SCREENING

For targeting, the plasmids are cut with restriction enzymes that free the insert away from the plasmid backbone. In the case of p5'hGH-mMT, HindIII digestion releases a targeting fragment of 2.9 kb, comprised of the 1.8 kb mMT promoter flanked on the 5' end 3' sides by DNA for targeting this construct to the regulatory region of the hGH gene. This DNA or the 2.9 kb targeting fragment alone is purified by phenol extraction and ethanol precipitation and transfected into primary or secondary human fibroblasts under the conditions described in Example 11. Transfected cells are plated onto 150 mm dishes in human fibroblast nutrient medium. 48 hours later the cells are plated into 24 well dishes at a density of 10,000 cells/cm$^2$ [approximately 20,000 cells per well; if targeting occurs at a rate of 1 event per $10^6$ clonable cells (Example 1c), then about 50 wells would need to be assayed to isolate a single expressing colony]. Cells in which the transfecting DNA has targeted to the homologous region upstream of hGH will express hGH under the control of the mMT promoter. After 10 days, whole well supernatants are assayed for hGH expression using a commercially available immunoassay kit (Nichols). Clones from wells displaying hGH synthesis are isolated using known methods, typically by assaying fractions of the heterogenous populations of cells separated into individual wells or plates, assaying fractions of these positive wells, and repeating as needed, ultimately isolated the targeted colony by screening 96-well microtiter plates seeded at one cell per well. DNA from entire plate lysates can also be analyzed by PCR for amplification of a fragment using a mMT specific primer in conjunction with a primer lying downstream of HUMGHCSA nucleotide position 5,432. This primer pair should amplify a DNA fragment of a size precisely predicted based on the DNA sequence. Positive plates are trypsinized and replated at successively lower dilutions, and the DNA preparation and PCR steps repeated as needed to isolate targeted cells.

The targeting schemes herein described can also be used to activate hGH expression in immortalized human cells (for example, HT1080 cells (ATCC CCL 121), HeLa cells and derivatives of HeLa cells (ATCC CCL2, 2.1 and 2.2), MCF-7 breast cancer cells (ATCC HBT 22), K-562 leukemia cells (ATCC CCL 232), KB carcinoma cells (ATCC CCL 17), 2780AD ovarian carcinoma cells (Van der Blick, A. M. et al., *Cancer Res*, 48:5927–5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), MOLT-4 cells (ATCC CRL 1582), and various heterohybridoma cells) for the purposes of producing hGH for conventional pharmaceutic delivery.

k. ACTIVATING THE HUMAN hGH GENE AND ISOLATION OF TARGETED PRIMARY, SECONDARY AND IMMORTALIZED HUMAN FIBROBLASTS BY A POSITIVE OR A COMBINED POSITIVE/NEGATIVE SELECTION SYSTEM

The strategy for constructing p5'hGH-mMT can be followed with the additional step of inserting the neo gene adjacent to the mMT promoter. In addition, a negative selection marker, for example, gpt [from pMSG (Pharmacia) or another suitable source], can be inserted adjacent to the HUMGHCSA sequences in the pUC12 poly-linker. In the former case, G418® colonies are isolated and screened by PCR amplification or restriction enzyme and Southern hybridization analysis of DNA prepared from pools of colonies to identify targeted colonies. In the latter case, G418® colonies are placed in medium containing thioxanthine to select against the integration of the gpt gene (Besnard, C. et al., *Mol. Cell. Biol*. 7: 4139–4141 (1987)]. In addition, the HSV-TK gene can be placed on the opposite side of the insert as gpt, allowing selection for neo and against both gpt and TK by growing cells in human fibroblast nutrient medium containing 400 µg/ml G418, 100 µM 6-thioxanthine, and 25 µg/ml gancyclovir. The double negative selection should provide a nearly absolute selection for true targeted events. Southern hybridization analysis is confirmatory.

The targeting schemes herein described can also be used to activate hGH expression in immortalized human cells (for example, HT1080 cells (ATCC CCL 121), HeLa cells and derivatives of HeLa cells (ATCC CCL2, 2.1 and 2.2), MCF-7 breast cancer cells (ATCC HBT 22), K-562 leukemia cells (ATCC CCL 232), KB carcinoma cells (ATCC CCL 17), 2780AD ovarian carcinoma cells (Van der Blick, A. M. et al., *Cancer Res*, 48:5927–5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), MOLT-4 cells (ATCC CRL 1582), and various heterohybridoma cells) for the purposes of producing hGH for conventional pharmaceutic delivery.

The targeting constructs described in Examples 1f and 1i, and used in Examples 1g, 1h, 1j and 1k can be modified to include an amplifiable selectable marker (e.g., ada, dhfr, or CAD) which is useful for selecting cells in which the activated endogenous gene, and the amplifiable selectable marker, are amplified. Such cells, expressing or capable of expressing the endogenous gene encoding a therapeutic product can be used to produce proteins (e.g., hGH and hEPO) for conventional pharmaceutic delivery or for gene therapy.

l. TRANSFECTION OF PRIMARY AND SECONDARY FIBROBLASTS WITH EXOGENOUS DNA AND A SELECTABLE MARKER GENE BY ELECTROPORATION

Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na$_2$HPO$_4$, 6 mM dextrose). The cells are recentrifuged, the supernatant aspirated, and the cells resuspended in electroporation buffer containing 1 mg/ml acetylated bovine serum albumin. The final cell suspension contains approximately 3×10$^6$ cells/ml. Electroporation should be performed immediately following resuspension.

Supercoiled plasmid DNA is added to a sterile cuvette with a 0.4 cm electrode gap (Bio-Rad.) The final DNA concentration is generally at least 120 µg/ml. 0.5 ml of the cell suspension (containing approximately 1.5×10$^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (as above with 15% calf serum) in a 10 cm dish and incubated as described above. The following day, the media is aspirated and replaced with 10 ml of fresh media and incubated for a further 16–24 hours. Subculture of cells to determine cloning efficiency and to select for G418-resistant colonies is performed the following day. Cells are trypsinized, counted and plated; typically, fibroblasts are plated at $10^3$ cells/10 cm dish for the determination of cloning efficiency and at $1-2 \times 10^4$ cells/10 cm dish for G418 selection.

Human fibroblasts are selected for G418 resistance in medium consisting of 300–400 μg/ml G418 (Geneticin, disulfate salt with a potency of approximately 50%; Gibco) in fibroblasts nutrient media (with 15% calf serum). Cloning efficiency is determined in the absence of G418. The plated cells are incubated for 12–14 days, at which time colonies are fixed with formalin, stained with crystal violet and counted (for cloning efficiency plated) or isolated using cloning cylinders (for G418 plates). Electroporation and selection of rabbit fibroblasts is performed essentially as described for human fibroblasts, with the exception of the selection conditions used. Rabbit fibroblasts are selected for G418 resistance in medium containing 1 gm/ml G418.

Fibroblasts were isolated from freshly excised human foreskins. Cultures were seeded at 50,000 cells/cm in DMEM+10% calf serum. When cultures became confluent, fibroblasts were harvested by trypsinization and transfected by electroporation. Electroporation conditions were evaluated by transfection with the plasmid pcDNEO (FIG. 5). A representative electroporation experiment using near optimal conditions (60 μg of plasmid pcDNEO at an electroporation voltage of 250 volts and a capacitance setting of 960 μFarads) resulted in one G418 colony per 588 treated cells (0.17% of all cells treated), or one G418 colony per 71 clonable cells(1.4%).

When nine separate electroporation experiments at near optimal conditions (60 μg of plasmid pcDNEO at an electroporation voltage of 300 volts and a capacitance setting of 960 μFarads) were performed, an average of one G418 colony per 1,899 treated cells (0.05%) was observed, with a range of 1/882 to 1/7,500 treated cells. This corresponds to an average of one G418 colony per 38 clonable cells (2.6%).

Low passage primary human fibroblasts were converted to hGH expressing cells by co-transfection with plasmids; pcDNEO and pXGH5. Typically, 60 μg of an equimolar mixture of the two plasmids were transfected at near optimal conditions (electropotation voltage of 300 volts and a capacitance setting of 960 μFarads). The results of such an experiment resulted in one G418 colony per 14,705 treated cells.

hGH expression data for these and other cells isolated under identical transfection conditions are summarized below. Ultimately, 98% of all G418® colonies could be expanded to generate mass cultures.

| | |
|---|---|
| Number of G418$^r$ Clones Analyzed | 154 |
| Number of G418$^r$/hGH Expressing Clones | 65 |
| Average hGH Expression Level | 2.3 μg hGH/$10^6$ Cells/24 hr |
| Maximum hGH Expression Level | 23.0 μg hGH/$10^6$ Cells/24 hr |

Stable transfectants also have been generated by electroporation of primary or secondary human fibroblasts with pXGH301, a DNA construct in which the neo and hGH genes are present on the same plasmid molecule. pXGH301 was constructed by a two-step procedure. The SalI-ClaI fragment from pBR322 (positions 23–651 in pBR322) was isolated and inserted into SalI-ClaI digested pcDNEO, introducing a BamHI site upstream of the SV40 early promoter region of pcDNEO. This plasmid, pBNEO was digested with BamHi and the 2.1 kb fragment containing the neo gene under the control of the SV40 early promoter, was isolated and inserted into BamHI digested pXGH5. A plasmid with a single insertion of the 2.1 kb BamHI fragment was isolated in which neo and hGH are transcribed in the same direction relative to each other. This plasmid was designated pXGH301. For example, $1.5 \times 10^6$ cells were electroporated with 60 μg pXGH301 at 300 volts and 960 μFarads. G418 resistant colonies were isolated from transfected secondary fibroblasts at a frequency of 652 G418 resistant colonies per $1.5 \times 10$ treated cells (1 per 2299 treated cells). Approximately 59% of these colonies express hGH.

Example 2. CONSTRUCTION OF TARGETING PLASMIDS WHICH RESULT IN CHIMERIC TRANSCRIPTION UNITS IN WHICH HUMAN GROWTH HORMONE AND ERYTHROPOIETIN SEQUENCES ARE FUSED The following serves to illustrate two further embodiments of the present invention, in which the normal regulatory sequences upstream of the human EPO gene are altered to allow expression of hEPO in primary or secondary fibroblast strains which do not express hEPO in detectable quantities in their untransfected state as obtained. In these embodiments, the products of the targeting events are chimeric transcription units in which the first exon of the human growth hormone gene is positioned upstream of hEPO exons 2–5. The product of transcription, splicing and translation is a protein in which amino acids 1–4 of the hEPO signal peptide are replaced with amino acid residues 1–3 of hGH. The two embodiments differ with respect to both the relative positions of the foreign regulatory sequences that are inserted and the specific pattern of splicing that needs to occur to produce the final, processed transcript.

Plasmid pXEPO-10 is designed to replace exon 1 of hEPO with exon 1 of hGH by gene targeting to the endogenous hEPO gene on human chromosome 7. Plasmid pXEPO-10 is constructed as follows. First, the intermediate plasmid pT163 is constructed by inserting the 6 kb HindIII-BamHI fragment (see Example 1f) lying upstream of the hEPO coding region into HindIII-BamHI digested pBluescriptII SK+ (Stratagene, LaJolla, Calif.). The product of this ligation is digested with XhoI and HindIII and ligated to the 1.1 kb HindIII-XhoI fragment from pMC1neoPolyA [Thomas, K. R. and Capecchi, M. R. Cell 51:503–512 (1987) available from Stratagene, LaJolla, Calif.] to create pT163. Oligonucleotides 13.1–13.4 are utilized in polymerase chain reactions to generate a fusion fragment in which the mouse metallothionein 1 (mMT-I) promoter—hGH exon 1 sequences are additionally fused to hEPO intron 1 sequences. First, oligonucleotides 13.1 and 13.3 are used to amplify the approximately 0.73 kb mMT-I promoter—hGH exon 1 fragment from pXGH5 (FIG. 5). Next, oligonucleotides 13.2 and 13.4 are used to amplify the approximately 0.57 kb fragment comprised predominantly of hEPO intron 1 from human genomic DNA. Finally, the two amplified fragments are mixed and further amplified with oligonucleotides 13.1 and 13.4 to generate the final fusion fragment (fusion fragment 3) flanked by a SalI site at the 5' side of the mMT-I moiety and an XhoI site at the 3' side of the hEPO intron 1 sequence. Fusion fragment 3 is digested with XhoI and SalI and ligated to XhoI digested pT163. The ligation mixture is transformed into *E. coli* and a clone containing a single insert of fusion fragment 3 in which the XhoI site is regenerated at the 3' side of hEPO intron 1 sequences is identified and designated pXEPO-10.

13.1  5' TTTTGTCGAC  GGTACCTTGG  TTTTTAAAAC  C  (SEQ ID NO 5)
           SalI          KpnI 13.2  5' CCTAGCGGCA  ATGGCTACAG  GTGAGTACTC  GCGGGCTGGG  CG  (SEQ ID NO 6)

13.3  5' CGCCCAGCCC  GCGAGTACTC  ACCTGTAGCC  ATTGCCGCTA  GG  (SEQ ID NO 7)

13.4  5' TTTTCTCGAG  CTAGAACAGA  TAGCCAGGCT  G  (SEQ ID NO 8)
           XhoI

The non-boldface region of oligo 13.1 is identical to the mMT-I promoter, with the natural KpnI site as its 5'

13.5  5' *GACAGCTCAC*  CTAGCGGCAA  TGGCTACAG*G*  *TGAGTACTC*  (SEQ ID NO 9)
         *AAGCTTCTGG*  GCTTCCAGAC  CCAG
          HindIII 13.6  5' CTGGGTCTGG  AAGCCCAGAA  GCTT*GAGTAC*  *TCACCTGTAG*  (SEQ ID NO 10)
                        HindIII
         CCATTGCCGC  TAGGTGAGCT  GTC

13.7  5' TTTTCTCGAG  CTCCGCGCCT  GGCCGGGGTC  CCTC  (SEQ ID NO 11)
           XhoI boundary. The boldface type denotes a SalI site tail to convert the 5' boundary to a SalI site. The boldface region of oligos 13.2 and 13.3 denote hGH sequences, while the non-boldface regions are intron 1 sequences from the hEPO gene. The non-boldface region of oligo 13.4 is identical to the last 25 bases of hEPO intron 1. The boldface region includes an XhoI site tail to convert the 3' boundary of the amplified fragment to an XhoI site.

Plasmid pXEPO-11 is designed to place, by gene targeting, the mMT-I promoter and exon 1 of hGH upstream of the hEPO structural gene and promoter region at the endogenous hEPO locus on human chromosome 7. Plasmid pXEPO-11 is constructed as follows. Oligonucleotides 13.1 and 13.5–13.7 are utilized in polymerase chain reactions to generate a fusion fragment in which the mouse metallothionein I (mMT-I) promoter—hGH exon 1 sequences are additionally fused to hEPO sequences from –1 to –630 relative to the hEPO coding region. First, oligonucleotides 13.1 and 13.6 are used to amplify the approximately 0.75 kb mMT-I promoter—hGH exon 1 fragment from pXGH5 (FIG. 5). Next, oligonucleotides 13.5 and 13.7 are used to amplify, from human genomic DNA, the approximately 0.65 kb fragment comprised predominantly of hEPO sequences from –1 to –620 relative to the hEPO coding region. Both oligos 13.5 and 13.6 contain a 10 bp linker sequence located at the hGH intron 1—hEPO promoter region, which corresponds to the natural hEPO intron 1 splice-donor site. Finally, the two amplified fragments are mixed and further amplified with oligonucleotides 13.1 and 13.7 to generate the final fusion fragment (fusion fragment 6) flanked by a SalI site at the 5' side of the mMT-I moiety and an XhoI site at the 3' side of the hEPO promoter region. Fusion fragment 6 is digested with XhoI and SalI and ligated to XhoI digested pT163. The ligation mixture is transformed into *E. coli* and a clone containing a single insert of fusion fragment 6 in which the XhoI site is regenerated at the 3' side of hEPO promoter sequences is identified and designated pXEPO-11.

The boldface regions of oligos 13.5 and 13.6 denote hGH sequences. The italicized regions correspond to the first 10 base pairs of hEPO intron 1. The remainder of the oligos correspond to hEPO sequences from –620 to –597 relative to the hEPO coding region. The non-boldface region of oligo 13.7 is identical to bases –1 to –24 relative to the hEPO coding region. The boldface region includes an XhoI site tail to convert the 3' boundary of the amplified fragment to an XhoI site.

Plasmid pXEPO-10 can be used for gene targeting by digestion with BamHI and XhoI to release the 7.3 kb fragment containing the mMT-I/hGH fusion flanked on both sides by hEPO sequences. This fragment (targeting fragment 1) contains no hEPO coding sequences, having only sequences lying between –620 and approximately –6620 upstream of the hEPO coding region and hEPO intron 1 sequences to direct targeting to the human EPO locus. Targeting fragment 1 is transfected into primary or secondary human skin fibroblasts using conditions similar to those described in Example 1c. G418-resistant colonies are picked into individual wells of 96-well plates and screened for EPO expression by an ELISA assay (R&D Systems, Minneapolis Minn.). Cells in which the transfecting DNA integrates randomly into the human genome cannot produce EPO. Cells in which the transfecting DNA has undergone homologous recombination with the endogenous hEPO intron 1 and hEPO upstream sequences contain a chimeric gene in which the mMT-I promoter and non-transcribed sequences and the hGH 5' untranslated sequences and hGH exon 1 replace the normal hEPO promoter and hEPO exon 1 (see FIG. 1). Non-hEPO sequences in targeting fragment 1 are joined to hEPO sequences down-stream of hEPO intron 1. The replacement of the normal hEPO regulatory region with the mMT-I promoter will activate the EPO gene in fibroblasts, which do not normally express hEPO. The replacement of hEPO exon 1 with hGH exon 1 results in a protein in which the first 4 amino acids of the hEPO signal peptide are replaced with amino acids 1–3 of hGH, creating a functional, chimeric signal peptide which is removed by post-translation processing from the mature protein and is secreted from the expressing cells.

Figure 2:
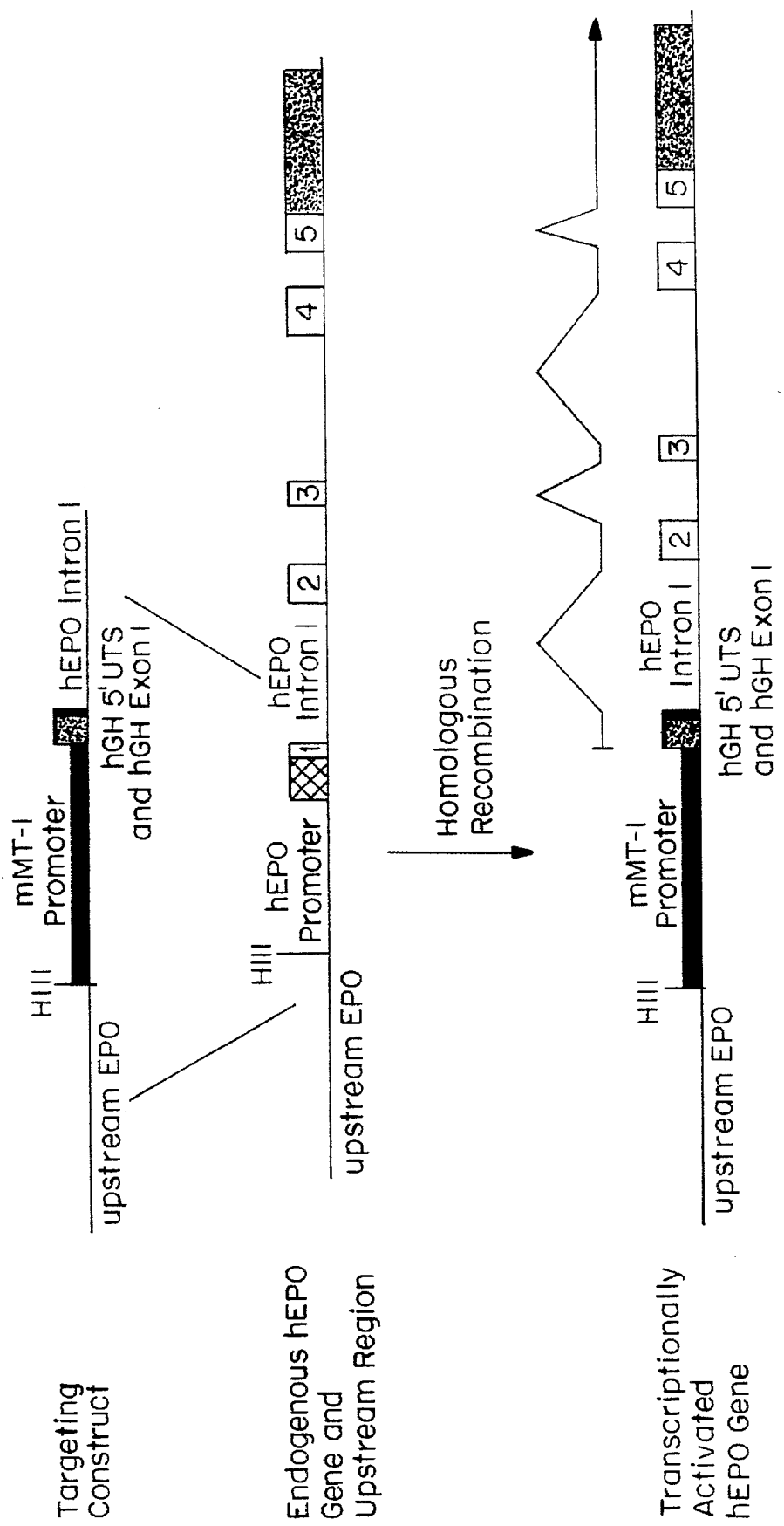
FIG. 2 is a schematic diagram of a strategy for transcriptionally activating the hEPO gene; thick lines, mouse metallothionein I promoter; stippled box, 5' untranslated region of hGH; solid box, hGH exon 1; open numbered boxes, hEPO coding sequences; diagonally-stripped box, hEPO 3' translated sequences; HIII, HindIII site.

Plasmid pXEPO-11 can be used for gene targeting by digestion with BamHI and XhoI to release the 7.4 kb fragment containing the mMT-I/hGH fusion flanked on both sides by hEPO sequences. This fragment (targeting fragment 2) contains no hEPO coding sequences, having only sequences lying between -1 and approximately -6620 upstream of the hEPO coding region to direct targeting to the human EPO locus. Targeting fragment 2 is transfected into primary or secondary human skin fibroblasts using conditions similar to those described in Example 1g. G418-resistant colonies are picked into individual wells of 96-well plates and screened for EPO expression by an ELISA assay (R&D Systems, Minneapolis, Minn.). Cells in which the transfecting DNA integrates randomly into the human genome cannot produce EPO. Cells in which the transfecting DNA has undergone homologous recombination with the endogenous hEPO promoter and upstream sequences contain a chimeric gene in which the mMT-I promoter and non-transcribed sequences, hGH 5' untranslated sequences and hGh exon 1, and a 10 base pair linker comprised of the first 10 bases of hEPO intron 1 are inserted at the HindIII site lying at position -620 relative to the hEPO coding region (see FIG. 2). The localization of the mMT-I promoter upstream of the normally silent hEPO promoter will direct the synthesis, in primary or secondary skin fibroblasts, of a message reading (5' to 3') non-translated metallothionein and hGH sequences, hGH exon 1, 10 bases of DNA identical to the first 10 base pairs of hEPO intron 1, and the normal hEPO promoter and hEPO exon 1 (-620 to +13 relative to the hEPO coding sequence). The 10 base pair linker sequence from hEPO intron 1 acts as a splice-donor site to fuse hGH exon 1 to the next downstream splice acceptor site, that lying immediately upstream of hEPO exon 2. Processing of the resulting transcript will therefore splice out the hEPO promoter, exon 1, and intron 1 sequences. The replacement of hEPO exon 1 with hGH exon 1 results in a protein in which the first 4 amino acids of the hEPO signal peptide are replaced with amino acids 1-3 of hGH, creating a functional, chimeric signal peptide which is removed by post-translation processing from the mature protein and is secreted from the expressing cells.

A series of constructs related to pXEPO-10 and pXEPO-11 can be constructed, using known methods. In these constructs, the relative positions of the mMT-I promoter and hGH sequences, as well as the position at which the mMT-I/hGH sequences are inserted into hEPO upstream sequences, are varied to create alternative chimeric transcription units that facilitate gene targeting, result in more efficient expression of the fusion transcripts, or have other desirable properties. Such constructs will give similar results, such that an hGH-hEPO fusion gene is placed under the control of an exogenous promoter by gene targeting to the normal hEPO locus. For example, the 6 kb HindIII-BamHI fragment upstream of the hEPO gene (See Example 1f) has numerous restriction enzyme recognition sequences that can be utilized as sites for insertion of the neo gene and the mMT-I promoter/hGH fusion fragment. One such site, a BglII site lying approximately 1.3 kb upstream of the HindIII site, is unique in this region and can be used for insertion of one or more selectable markers and a regulatory region derived from another gene that will serve to activate hEPO expression in primary, secondary, or immortalized human cells.

First, the intermediate plasmid pT164 is constructed by inserting the 6 kb HindIII-BamHI fragment (Example 1f) lying upstream of the hEPO coding region into HindIII-BamHI digested pBluescriptII SK+ (Stratagene, LaJolla, Calif.). Plasmid pMC1neoPolyA [Thomas, K. R. and Capecchi, M. R. Cell 51:503–512 (1987); available from Stratagene, LaJolla, Calif.] is digested with BamHI and XhoI, made blunt-ended by treatment with the Klenow fragment of E. coli DNA polymerase, and the resulting 1.1 kb fragment is purified. pT164 is digested with BglII and made blunt-ended by treatment with the Klenow fragment of E. coli DNA polymerase. The two preceding blunt-ended fragments are ligated together and transformed into competent E. coli. Clones with a single insert of the 1.1 kb neo fragment are isolated and analyzed by restriction enzyme analysis to identify those in which the BglII site recreated by the fusion of the blunt XhoI and BglII sites is localized 1.3 kb away from the unique HindIII site present in plasmid pT164. The resulting plasmid, pT165, can now be cleaved at the unique BglII site flanking the 5' side of the neo transcription unit.

Oligonucleotides 13.8 and 13.9 are utilized in polymerase chain reactions to generate a fragment in which the mouse metallothionein I (mMT-I) promoter—hGH exon 1 sequences are additionally fused to a 10 base pair fragment comprising a splice-donor site. The splice-donor site chosen corresponds to the natural hEPO intron 1 splice-donor site, although a larger number of splice-donor sites or consensus splice-donor sites can be used. The oligonucleotides (13.8 and 13.9) are used to amplify the approximately 0.73 kb mMT-I promoter—hGH exon 1 fragment from pXGH5 (FIG. 5). The amplified fragment (fragment 7) is digested with BglII and ligated to BglII digested pT165. The ligation mixture is transformed into E. coli and a clone, containing a single insert of fragment 7 in which the KpnI site in the mMT-I promoter is adjacent to the 5' end of the neo gene and the mMT-I promoter is oriented such that transcription is directed towards the unique HindIII site, is identified and designated pXEPO-12.

```
13.8  5' AAAAAGATCT   GGTACCTTGG   TTTTTAAAAC   CAGCCTGGAG      (SEQ ID NO 12)
         BglII        KpnI
```

The non-boldface region of oligo 13.8 is identical to the mMT-I promoter, with the natural KpnI site as its 5' boundary. The boldface type denotes a BglII site tail to convert the 5' boundary to a BglII site.

```
13.9  5' TTTTAGATCT   GAGTACTCAC   CTGTAGCCAT   TGCCGCTAGG      (SEQ ID NO 13)
         BglII
```

The boldface region of oligos 13.9 denote hGH sequences. The italicized region corresponds to the first 10 base pairs of hEPO intron 1. The underlined BglII site is added for plasmid construction purposes.

Plasmid pXEPO-12 can be used for gene targeting by digestion with BamHI and HindIII to release the 7.9 kb fragment containing the neo gene and the mMT-I/hGH fusion flanked on both sided by hEPO sequences. This fragment (targeting fragment 3) contains no hEPO coding sequences, having only sequences lying between approximately −620 and approximately −6620 upstream of the hEPO coding region to direct targeting upstream of the human EPO locus. Targeting fragment 3 is transfected into primary, secondary, or immortalized human skin fibroblasts using conditions similar to those described in Examples 1b and 1c. G418-resistant colonies are picked into individual wells of 96-well plates and screened for EPO expression by an ELISA assay (R&D Systems, Minneapolis Minn.). Cells in which the transfecting DNA integrates randomly into the human genome cannot produce hEPO. Cells in which the transfecting DNA has undergone homologous recombination with the endogenous hEPO promoter and upstream sequences contain a chimeric gene in which the mMT-I promoter and non-transcribed sequences, hGH 5' untranslated sequences, and hGH exon 1, and a 10 base pair linker comprised of the first 10 bases of hEPO intron 1 are inserted at the BglII site lying at position approximately −1920 relative to the hEPO coding region. The localization of the mMT-I promoter upstream of the normally silent hEPO promoter will direct the synthesis, in primary, secondary, or immortalized human fibroblasts (or other human cells), of a message reading: (5' to 3') nontranslated metallothionein and hGH sequences, hGH exon 1, 10 bases of DNA identical to the first 10 base pairs of hEPO intron 1, and hEPO upstream region and hEPO exon 1 (from approximately −1920 to +13 relative to the EPO coding sequence). The 10 base pair linker sequence from hEPO intron 1 acts as a splice-donor site to fuse hGH exon 1 to a downstream splice acceptor site, that lying immediately upstream of hEPO exon 2. Processing of the resulting transcript will therefore splice out the hEPO upstream sequences, promoter region, exon 1, and intron 1 sequences. When using pXEPO-10, -11 and -12, post-transcriptional processing of the message can be improved by using in vitro mutagenesis to eliminate splice acceptor sites lying in hEPO upstream sequences between the mMT-I promoter and hEPO exon 1, which reduce level of productive splicing events needed create the desired message. The replacement of hEPO exon 1 with hGH exon 1 results in a protein in which the first 4 amino acids of the hEPO signal peptide are replaced with amino acids 1-3 of hGH, creating a functional, chimeric signal peptide which is removed by post-translation processing from the mature protein and is secreted from the expressing cells.

Example 3. TARGETED MODIFICATION OF SEQUENCES UPSTREAM AND AMPLIFICATION OF THE TARGETED GENE Human cells in which the hEPO gene has been activated by the methods previously described can be induced to amplify the neo/mMT-1/EPO transcription unit if the targeting plasmid contains a marker gene that can confer resistance to a high level of a cytotoxic agent by the phenomenon of gene amplification. Selectable marker genes such as dihydrofolate reductase (dhfr, selective agent is methotrexate), the multifunctional CAD gene [encoding carbamyl phosphate synthase, aspartate transcarbamylase, and dihydro-orotase; selective agent is N-(phosphonoacetyl) -L-aspartate (PALA)], glutamine synthetase; selective agent is methionine sulphoximine (MSX), and adenosine deaminase (ada; selective agent is an adenine nucleoside), have been documented, among other genes, to be amplifiable in immortalized human cell lines (Wright, J. A. et al. Proc. Natl. Acad. Sci. USA 87:1791–1795 (1990); Cockett, M. I. et al. Bio/Technology 8:662–667 (1990)). In these studies, gene amplification has been documented to occur in a number of immortalized human cell lines. HT1080, HeLa, MCF-7 breast cancer cells, K-562 leukemia cells, KB carcinoma cells, or 2780AD ovarian carcinoma cells, among other cells, display amplification under appropriate selection conditions.

Plasmids pXEPO-10 and pXEPO-11 can be modified by the insertion of a normal or mutant dhfr gene into the unique HindIII sites of these plasmids. After transfection of HT1080 cells with the appropriate DNA, selection for G418-resistance (conferred by the neo gene), and identification of cells in which the hEPO gene has been activated by gene targeting of the neo, dhfr, and mMT-1 sequences to the correct position upstream of the hEPO gene, these cells can be exposed to stepwise selection in methotrexate (MTX) in order to select for amplification of dhfr and co-amplification of the linked neo, mMT-1, and hEPO sequences (Kaufman, R. J. Technique 2:221–236 (1990)). A stepwise selection scheme in which cells are first exposed to low levels of MTX (0.01 to 0.08 µM), followed by successive exposure to incremental increases in MTX concentrations up to 250 µM MTX or higher is employed. Linear incremental steps of 0.04 to 0.08 µM MTX and successive 2-fold increases in MTX concentration will be effective in selecting for amplified transfected cell lines, although a variety of relatively shallow increments will also be effective. Amplification is monitored by increases in dhfr gene copy number and confirmed by measuring in vitro hEPO expression. By this strategy, substantial overexpression of hEPO can be attained by targeted modification of sequences lying completely outside of the hEPO coding region.

Constructs similar to those described (Examples 1f, 1h, 1i, 1k, 2 and 7) to activate hGH expression in human cells can also be further modified to include the dhfr gene for the purpose of obtaining cells that overexpress the hGH gene by gene targeting to non-coding sequences and subsequent amplification.

Example 4. TARGETING AND ACTIVATION OF THE HUMAN EPO LOCUS IN AN IMMORTALIZED HUMAN FIBROBLAST LINE The targeting construct pXEPO-13 was made to test the hypothesis that the endogenous hEPO gene could be activated in a human fibroblast cell. First, plasmid pT22.1 was constructed, containing 63 bp of genomic hEPO sequence upstream of the first codon of the hEPO gene fused to the mouse metallothionein-1 promoter (mMT-I). Oligonucleotides 22.1 to 22.4 were used in PCR to fuse mMT-I and hEPO sequences. The properties of these primers are as follows: 22.1 is a 21 base oligonucleotide homologous to a segment of the mMT-I promoter beginning 28 bp upstream of the mMT-I KpnI site; 22.2 and 22.3 are 58 nucleotide complementary primers which define the fusion of hEPO and mMT-I sequences such that the fusion contains 28 bp of hEPO sequence beginning 35 bases upstream of the first codon of the hEPO gene, and mMT-I sequences beginning at base 29 of oligonucleotide 22.2, comprising the natural BglII site of mMT-I and extending 30 bases into mMT-I sequence; 22.4 is 21 nucleotides in length and is homologous to hEPO sequences beginning 725 bp downstream of the first codon of the hEPO gene. These primers were used to amplify a 1.4 kb DNA fragment comprising a fusion of mMT-I and hEPO sequences as described above. The resulting fragment was digested with KpnI (the PCR fragment contained two KpnI sites: a single natural KpnI site in the mMT-I promoter region and a single natural KpnI site in the hEPO sequence), and purified. The plasmid pXEPO1 was also digested with KpnI, releasing a 1.4 kb fragment and a 6.4 kb fragment. The 6.4 kb fragment was purified and ligated to the 1.4 kb KpnI PCR fusion fragment. The resulting construct was called pT22.1. A second intermediate, pT22.2, was constructed by ligating the approximately 6 kb HindIII-BamHI fragment lying upstream of the hEPO structural gene (see Example 1f) to BamHI and HindIII digested pBSIISK+ (Stratagene, LaJolla, Calif.). A third intermediate, pT22.3, was constructed by first excising a 1.1 kb XhoI/BamHI fragment from pMCINEOpolyA (Stratagene,, LaJolla, Calif.) containing the neomycin phosphotransferase gene. The fragment was then made blunt-ended with the Klenow fragment of DNA polymerase I (New England Biolabs). This fragment was then ligated to the HincII site of pBSIISK+ (similarly made blunt with DNA polymerase I) to produce pT22.3. A fourth intermediate, pT22.4, was made by purifying a 1.1 kb XhoI/HindIII fragment comprising the neo gene from pT22.3 and ligating this fragment to XhoI and HindIII digested pT22.2. pT22.4 thus contains the neo gene adjacent to the HindIII side of the BamHI-HindIII upstream hEPO fragment. Finally, pXEPO-13 was generated by first excising a 2.0 kb EcoRI/AccI fragment from pT22.-1. The EcoRI site of this fragment defines the 5' boundary of the mMT-I promoter, while the AccI site of this fragment lies within hEPO exon 5. Thus, the AccI/EcoRI fragment contains a nearly complete hEPO expression unit, missing only a part of exon 5 and the natural polyadenylation site. This 2.0 kb EcoRI/AccI fragment was purified, made blunt-ended by treatment with the Klenow fragment of DNA polymerase I, and ligated to XhoI digested, blunt-ended, pT22.4.

HT1080 cells were transfected with PvuI-BamHI digested pXEPO-13. pXEPO-13 digested in this way generates three fragments; a 1 kb vector fragment including a portion of the amp gene, a 1.7 kb fragment of remaining vector sequences and an approximately 9 kb fragment containing hEPO, neo and mMT-I sequences. This approximately 9 kb BamHI/PvuI fragment contained the following sequences in order from the BamHI site: an approximately 5.2 kb of upstream hEPO genomic sequence, the 1.1 kb neo transcription unit, the 0.7 kb mMT-I promoter and the 2.0 kb fragment containing hEPO coding sequence truncated within exon 5. 45 μg of pEXPO-13 digested in this way was used in an electroporation of 12 million cells (electroporation conditions were described in Example 1b). This electroporation was repeated a total of eight times, resulting in electroporation of a total of 96 million cells. Cells were mixed with media to provide a cell density of 1 million cells per ml and 1 ml aliquots were dispensed into a total of 96, 150 mm tissue culture plates (Falcon) each containing a minimum of 35 ml of DMEM/15% calf serum. The following day, the media was aspirated and replaced with fresh medium containing 0.8 mg/ml G418 (Gibco). After 10 days of incubation, the media of each plate was sampled for hEPO by ELISA analysis (R & D Systems). Six of the 96 plates contained at least 10 mU/ml hEPO. One of these plates, number 18, was selected for purification of hEPO expressing colonies. Each of the 96, 150 mm plates contained approximately 600 G418 resistant colonies (an estimated total of 57,600 G418 resistant colonies on all 96 plates). The approximately 600 colonies on plate number 18 were trypsinized and replated at 50 cells/ml into 364 well plates (Sterilin). After one week of incubation, single colonies were visible at approximately 10 colonies per large well of the 364 well plates (these plates are comprised of 16 small wells within each of the 24 large wells). Each well was screened for hEPO expression at this time. Two of the large wells contained media with at least 20 mU/ml hEPO. Well number A2 was found to contain 15 colonies distributed among the 16 small wells. The contents of each of these small wells were trypsinized and transferred to 16 individual wells of a 96 well plate. following 7 days of incubation the media from each of these wells was sampled for hEPO ELISA analysis. Only a single well, well number 10, contained hEPO. This cell strain was designated HT165-18A2-10 and was expanded in culture for quantitative hEPO analysis, RNA isolation and DNA isolation. Quantitative measurement of hEPO production resulted in a value of 2,500 milliunits/million cells/24 hours.

A 0.2 kb DNA probe extending from the AccI site in hEPO exon 5 to the BglII site in the 3' untranslated region was used to probe RNA isolated from HT165-18A2-10 cells. The targeting construct, pXEPO-13, truncated at the AccI site in exon 5 does not contain these AccI/BglII sequences and, therefore, is diagnostic for targeting at the hEPO locus. Only cell strains that have recombined in a homologous manner with natural hEPO sequences would produce an hEPO mRNA containing sequence homologous to the AccI/BglII sequences. HT165-18A2-10 was found to express an mRNA of the predicted size hybridizing with the 32-P labeled AccI/BglII hEPO probe on Northern blots. Restriction enzyme and Southern blot analysis confirmed that the neo gene and mMT-I promoter were targeted to one of the two hEPO alleles in HT165-18A2-10 cells.

These results demonstrate that homologous recombination can be used to target a regulatory region to a gene that is normally silent in human fibroblasts, resulting in the functional activation of that gene.

| | | | | |
|---|---|---|---|---|
| 22.1 | 5' CACCTAAAAT | GATCTCTCTG | G | (SEQ ID NO 14) |
| 22.2 | 5' CGCGCCGGGT GCTGGAGCTA | GACCACACCG CGGAGTAA | GGGGCCCTAG | ATCTGGTGAA (SEQ ID NO 15) |
| 22.3 | 5' TTACTCCGTA GTGTGGTCAC | GCTCCAGCTT CCGGCGCG | CACCAGATCT | AGGGCCCCCG (SEQ ID NO 16) |
| 22.4 | 5' GTCTCACCGT | GATATTCTCG | G | (SEQ ID NO 17) |

Example 5. PRODUCTION OF INTRONLESS GENES

Gene targeting can also be used to produce a processed gene, devoid of introns, for transfer into yeast or bacteria for gene expression and in vitro protein production. For example, hGH can by produced in yeast by the approach described below.

Two separate targeting constructs are generated. Targeting construct 1 (TC1) includes a retroviral LTR sequence, for example the LTR from the Moloney Murine Leukemia Virus (MoMLV), a marker for selection in human cells (e.g., the neo gene from Tn5), a marker for selection in yeast (e.g., the yeast URA3 gene), a regulatory region capable of directing gene expression in yeast (e.g., the GAL4 promoter), and optionally, a sequence that, when fused to the hGH gene, will allow secretion of hGH from yeast cells (leader sequence). The vector can also include a DNA sequence that permits retroviral packaging in human cells. The construct is organized such that the above sequences are flanked, on both sides, by hGH genomic sequences which, upon homologous recombination with genomic hGH gene N sequences, will integrate the exogenous sequences in TC1 immediately upstream of hGH gene N codon 1 (corresponding to amino acid position 1 in the mature, processed protein). The order of DNA sequences upon integration is: hGH upstream and regulatory sequences, neo gene, LTR, URA3 gene, GAL4 promoter, yeast leader sequence, hGH sequences including and downstream of amino acid 1 of the mature protein. Targeting Construct 2 (TC2) includes sequences sufficient for plasmid replication in yeast (e.g., 2-micron circle or ARS sequences), a yeast transcriptional termination sequence, a viral LTR, and a marker gene for selection in human cells (e.g., the bacterial gpt gene). The construct is organized such that the above sequences are flanked on both sides by hGH genomic sequences which, upon homologous recombination with genomic hGH gene N sequences, will integrate the exogenous sequences in TC2 immediately downstream of the hGH gene N stop codon. The order of DNA sequences upon integration is: hGH exon 5 sequences, yeast transcription termination sequences, yeast plasmid replication sequences, LTR, gpt gene, hGH 3' non-translated sequences.

Linear fragments derived from TC1 and TC2 are sequentially targeted to their respective positions flanking the hGH gene. After superinfection of these cells with helper retrovirus, LTR directed transcription through this region will result in an RNA with LTR sequences on both ends. Splicing of this RNA will generate a molecule in which the normal hGH introns are removed. Reverse transcription of the processed transcript will result in the accumulation of double-stranded DNA copies of the processed hGH fusion gene. DNA is isolated from the doubly-targeted, retrovirally-infected cells, and digested with an enzyme that cleaves the transcription unit once within the LTR. The digested material is ligated under conditions that promote circularization, introduced into yeast cells, and the cells are subsequently exposed to selection for the URA3 gene. Only cells which have taken up the URA3 gene (linked to the sequences introduced by TC1 and TC2 and the processed hGH gene) can grow. These cells contain a plasmid which will express the hGH protein upon galactose induction and secrete the hGH protein from cells by virtue of the fused yeast leader peptide sequence which is cleaved away upon secretion to produce the mature, biologically active, hGH molecule.

Expression in bacterial cells is accomplished by simply replacing, in TC1 and TC2, the ampicillin-resistance gene from pBR322 for the yeast URA3 gene, the tac promoter (deBoer et al., Proc. Natl. Acad. Sci. 80:21–25 (1983)) for the yeast GAL4 promoter, a bacterial leader sequence for the yeast leader sequence, the pBR322 origin of replication for the 2-micron circle or ARS sequence, and a bacterial transcriptional termination (e.g., trpA transcription terminator; Christie, G. E. et al., Proc. Natl. Acad. Sci. 78:4180–4184 (1981)) sequence for the yeast transcriptional termination sequence. Similarly, hEPO can be expressed in yeast and bacteria by simply replacing the hGH targeting sequences with hEPO targeting sequences, such that the yeast or bacterial leader sequence is positioned immediately upstream of hEPO codon 1 (corresponding to amino acid position 1 in the mature processed protein).

Example 6. ACTIVATION AND AMPLIFICATION OF THE EPO GENE IN AN IMMORTALIZED HUMAN CELL LINE Incorporation of a dhfr expression unit into the unique HindIII site of pXEPO-13 (see Example 4) results in a new targeting vector capable of dual selection and selection of cells in which the dhfr gene is amplified. The single HindIII site in pXEPO-13 defines the junction of the neo gene and genomic sequence naturally residing upstream of the human EPO gene. Placement of a dhfr gene at this site provides a construct with the neo and dhfr genes surrounded by DNA sequence derived from the natural hEPO locus. Like pXEPO-13, derivatives with the dhfr gene inserted are useful to target to the hEPO locus by homologous recombination. Such a construct designated pREPO4, is represented in FIG. 6. The plasmid includes exons 1–4 and part of exon 5 of the human EPO gene, as well as the HindIII-BamHI fragment lying upstream of the hEPO coding region. pSVe, pTK and pmMT-I correspond to the promoters from the SV40 early region, the Herpes Simplex Virus (HSV) thymidine kinase (TK) gene and the mouse metallothionein-I gene. It was produced as follows: HindIII-digested pXEPO-13 was purified and made blunt with the Klenow fragment of DNA polymerase I. To obtain a dhfr expression unit, the plasmid construct pF8CIS9080 (Eaton et al., *Biochemistry* 25:8343-8347 (1986)) was digested with EcoRI and SalI. A 2 Kb fragment containing the dhfr expression unit was purified from this digest and made blunt with Klenow fragment of DNA polymerase I. This dhfr-containing fragment was then ligated to the blunted HindIII site of pXEPO-13. An aliquot of this ligation was transformed into *E. coli* and plated on ampicillin selection plates. Following an overnight incubation at 37° C., individual bacterial colonies were observed, picked and grown. Miniplasmid preparations were made from these cultures and the resulting DNA was then subjected to restriction enzyme digestion with the enzymes BglII+HindIII, and SfiI in order to determine the orientation of the inserted dhfr fragments. Plasmid DNA from one of these preparations was found to contain such a 2 Kb insertion of the dhfr fragment. The transcription orientation of the dhfr expression unit in this plasmid was found to be opposite that of the adjacent neo gene. This is the construct designated pREPO4.

Plasmid pREPO4 was used to amplify the hEPO locus in cells subsequent to activation of the endogenous hEPO gene by homologous recombination. Gene activation with this construct allows selection for increased DHFR expression by the use of the drug methotrexate (MTX). Typically, increased DHFR expression would occur by an increase in copy number through DNA amplification. The net result would be co-amplification of the activated hEPO gene along with dhfr sequences. Co-amplification of the activated EPO locus should result in increased EPO expression.

Figure 7:
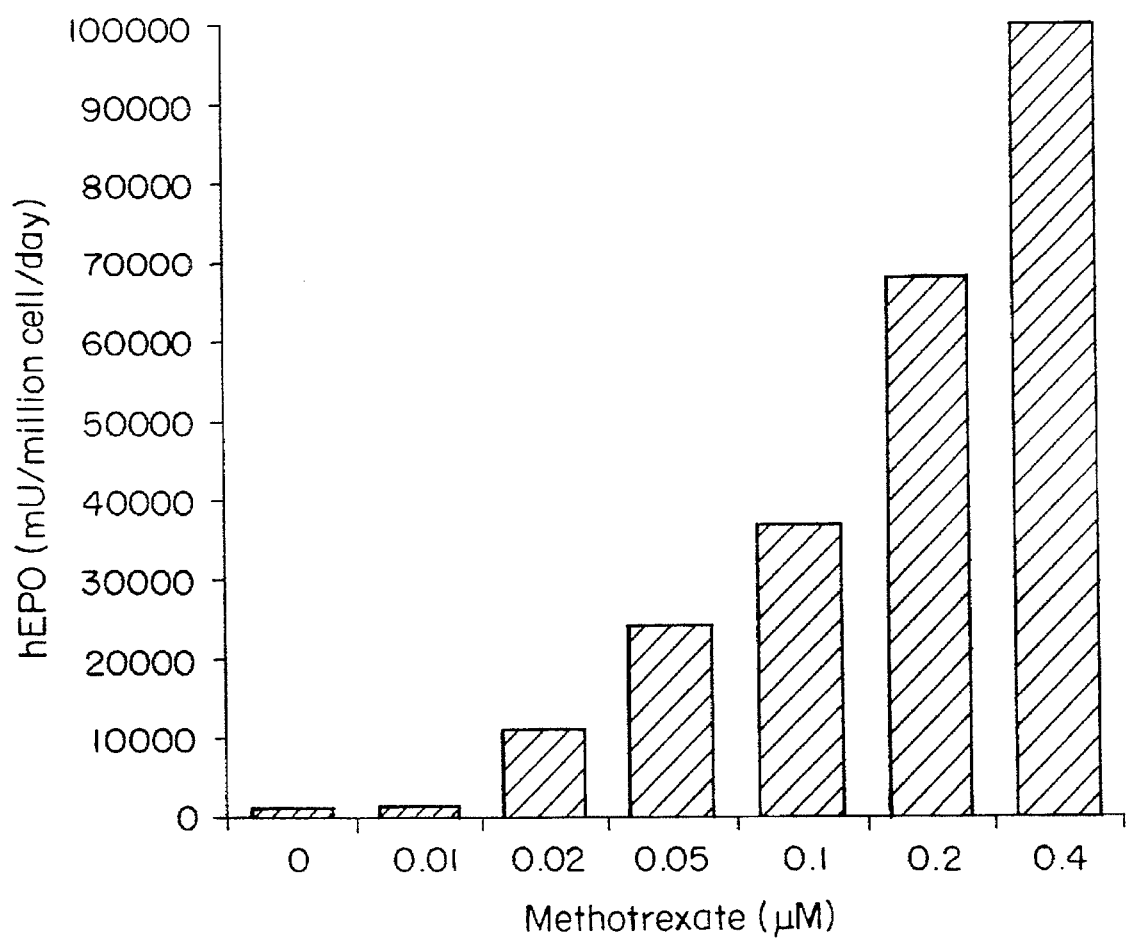
FIG. 7 is a graphic representation of erythropoietin expression in a targeted human cell line subjected to stepwise selection in 0.02, 0.05, 0.1, 0.2 and 0.4 µM methotrexate.

Targeting experiments were performed in HT1080 cells with pREPO4. hEPO expressing line HTREPO-52 was isolated. This line was analyzed quantitatively for EPO production and by Southern and Northern blot. This strain was found to be targeted with a single copy of dhfr/neo/mMT-1 sequences. Expression levels obtained under 0.8 mg/ml G418 selection were approximately 1300 mU/million cells/day. Because the targeted EPO locus contained a dhfr expression unit, it was possible to select for increased expression of DHFR with the antifolate drug, MTX. This strain was therefore subjected to stepwise selection in 0.02, 0.05, 0.1, 0.2 and 0.4 µM MTX. Results of initial selection of this strain are shown in Table 4 and FIG. 7.

TABLE 4

| Cell Line | MTX (µM) | mU/Million Cells/24 h |
| --- | --- | --- |
| 52C20-5-0 | 0 | 1368 |
| 52C20-5-.01 | 0.01 | 1744 |
| 52C20-5-.02 | 0.02 | 11643 |
| 52C20-5-0.05 | 0.05 | 24449 |
| 52-3-5-0.10 | 0.1 | 37019 |
| 52-3-2-0.20 | 0.2 | 67867 |
| 52-3-2-0.4B | 0.4 | 99919 |

Selection with elevated levels of MTX was successful in increasing hEPO expression in line HTREPO-52, with a 70-fold increase in EPO production seen in the cell line resistant to 0.4 µM MTX. Confirmation of amplification of the hEPO locus was accomplished by Southern blot analysis in MTX-resistant cell lines, which revealed an approximately 10-fold increase in the copy number of the activated hEPO locus relative to the parental (untargeted) hEPO allele.

Figure 8:
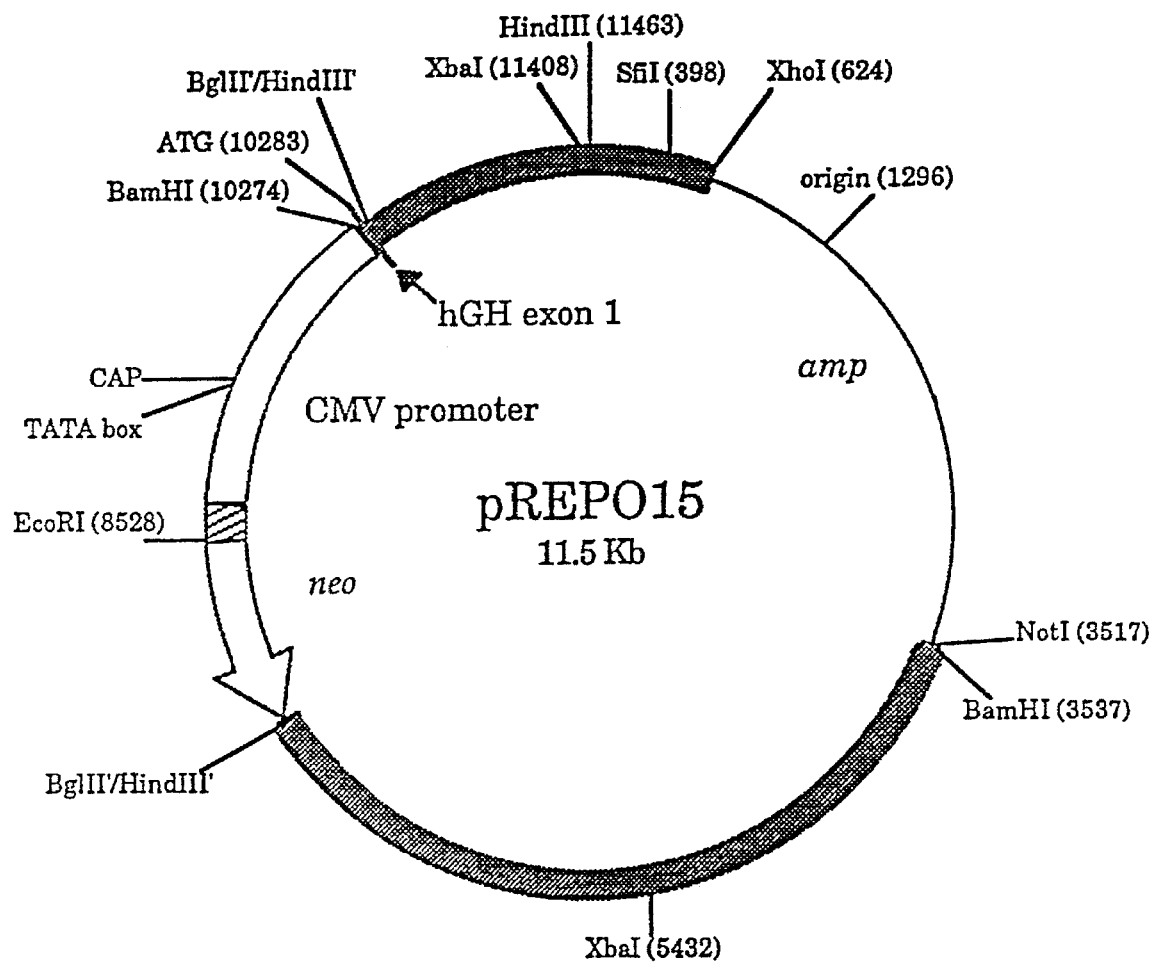
FIG. 8 is a schematic representation of plasmid pREPO15. Fragments derived from genomic hEPO sequences are indicated by filled boxes. The region between BamHI (3537) and BglII/HindIII corresponds to sequences at positions 1–4008 in Genbank entry HUMERPALU. The region between BglII/HindIII (11463) corresponds to DNA sequences at positions 4009–5169 in Genbank entry HUMERPALU. The region between HindIII (11463) and XhoI (624) contains sequence corresponding to positions 7–624 of Genbank entry HUMERPA. CMV promoter sequences are shown as an open box and contains sequence from nucleotides 546–2105 of Genbank sequence HS5MIEP. The neo gene is shown as an open box with an arrow. The thymidine kinase (tk) promoter driving the neo gene is shown as a hatched box. pBSIISK+ sequences including the amp gene are indicated by a thin line.

Example 7: PRODUCTION OF AN hEPO FUSION GENE BY INSERTION OF THE CMV PROMOTER 1.8 KB UPSTREAM OF THE GENOMIC hEPO CODING REGION Construction of targeting plasmid pREPO15:

pREPO15 was constructed by first fusing the CMV promoter to hGH exon 1 by PCR amplification. A 1.6 kb fragment was amplified from hGH expression construct pXGH308, which has the CMV promoter region beginning at nucleotide 546 and ending at nucleotide 2105 of Genbank sequence HSBMIEP fused to the hGH sequences beginning at nucleotide 5225 and ending at nucleotide 7322 of Genbank sequence HUMGHCSA, using oligonucleotides 20 and 35. Oligo 20 (35 bp, SEQ ID NO: 18), hybridized to the CMV promoter at −614 relative to the cap site (in Genbank sequence HEHCMVP1), and included a SalI site at its 5' end. Oligo 35 (42 bp, SEQ ID NO: 19), annealed to the CMV promoter at +966 and the adjacent hGH exon 1, and included the first 10 base pairs of hEPO intron 1(containing a portion of the splice-donor site) and a HindIII site at its 5' end. The resulting PCR fragment was digested with HindIII and SalI and gel-purified. Plasmid pT163 (Example 2) was digested with XhoI and HindIII and the approximately 1.1 kb fragment containing the neo expression unit was gel-purified. The 1.6 kb CMV promoter/hGH exon 1/splice-donor site fragment and the 1.2 kb neo fragment were ligated together and inserted into the HindIII site of pBSIISK+ (Stratagene, Inc.). The resulting intermediate plasmid (designated pBNCHS) contained a neo expression unit in a transcriptional orientation opposite to that of the CMV promoter/hGH exon 1/splice-donor site fragment). A second intermediate, pREPO5ΔHindIII, was constructed by first digesting pREPO5 with HindIII. This released two fragments of 1.9 kb and 8.7 kb, and the 8.7 Kb fragment containing EPO targeting sequences was gel purified and circularized by self-ligation. The resulting plasmid, pREPO5ΔHindIII, contained only non-coding genomic DNA sequences normally residing upstream of the hEPO gene. This included sequence from −5786 to −1 relative to EPO exon 1. The 2.8 kb fragment containing neo, the CMV promoter, hGH exon 1, and the splice-donor site was excised from pBNCHS with HindIII and gel-purified. This fragment was made blunt with the Klenow fragment of DNA polymerase I (New England Biolabs, Inc.) and ligated to BglII-digested and blunt-ended pREPO5ΔHindIII. BglII cuts at a position −1779 bp upstream of hEPO exon 1 in pREPO5ΔHindIII. The resulting construct, pREPO15 (FIG. 8), contained EPO upstream sequences from −5786 to −1779 relative to the hEPO coding region, the neo expression unit, the CMV promoter, hGH exon 1, a splice-donor site, and sequences from −1778 to −1 bp upstream of the hEPO coding region, with the various elements assembled, in the order listed, 5' to 3' relative to nucleotide sequence of the hEPO upstream region. For transfection of human cells, pREPO15 was digested with Not I and PvuI to liberate an 8.6 kb targeting fragment. The targeting fragment contained first and second targeting sequences of 4.0 kb and 1.8 kb, respectively, with homology to DNA upstream of the hEPO gene.

Cell culture, transfection, and identification of EPO expressing targeted clones:

All cells were maintained at 37° C., 5% $CO_2$ and 98% humidity in DMEM containing 10% calf serum (DMEM/10, HyClone Laboratories). Transfection of secondary human foreskin fibroblasts was performed by electroporating $12\times10^6$ cells in PBS (GIBCO) with 100 µg of DNA at 250 volts and 960 µF. The treated cells were seeded at $1\times10^6$ cells per 150 mm plate. The following day, the media was changed to DMEM/10 containing 0.8 mg/ml G418 (GIBCO). Selection proceeded for 14 days, at which time the media was sampled for EPO production. All colonies on plates exhibiting significant hEPO levels (>5 mU/ml) as determined by an EPO ELISA (Genzyme Inc.) were isolated with sterile glass cloning cylinders (Bellco) and transferred to individual wells of a 96 well plate. Following incubation for 1–2 days, these wells were sampled for hEPO production by ELISA. Resulting hEPO-producing cell strains were expanded in culture for freezing, nucleic acid isolation, and quantification of EPO production.

Transfection of HT1080 cells (ATCC CCL 121) was performed by treating $12\times10^6$ cells in PBS (GIBCO) with 45 µg of DNA at 450 volts and 250 µF. Growth and identification of clones occurred as for secondary human foreskin fibroblasts described above. Isolation of hEPO producing clonal cell lines occurred by limiting dilution. This was performed by first plating colonies harvested from the initial selection plates in pools of 10–15 colonies per well of a 24 well plate. hEPO producing pools were then plated at cell densities resulting in <1 colony per well of a 96 well plate. Individual clones were expanded for further analysis as described for human foreskin fibroblasts above.

Characterization of EPO expressing clones:

pREPO15 is devoid of any hEPO coding sequence. Upon targeting of the neo/CMV promoter/hGH exon 1/splice-donor fragment upstream of hEPO exon 1, hEPO expression occurs by transcriptional initiation from the CMV promoter, producing a primary transcript that includes CMV sequences, hGH exon 1 and the splice-donor site, 1.8 kb of upstream hEPO sequences, and the normal hEPO exons, introns, and 3' untranslated sequences. Splicing of this transcript would occur from the splice-donor site adjacent to hGH exon 1 to the next downstream splice-acceptor site, which is located adjacent to hEPO exon 2. Effectively, this results in a new intron consisting of genomic sequence upstream of the hEPO gene, the normal hEPO promoter, hEPO exon 1, and hEPO intron 1. In the mature transcript, hGH exon 1 would replace hEPO exon 1. hEPO exon 1 encodes only the first four and one-third amino acids of the 26 amino acid signal peptide, which is cleaved off of the precursor protein prior to secretion from the cell. hGH exon 1 encodes the first three and one-third amino acids of the hGH signal peptide, which also is cleaved off of the precursor protein prior to secretion from the cell. Translation of the message in which hGH exon 1 replaces hEPO exon 1 would therefore result in a protein in which the signal peptide is a chimera of hGH and hEPO sequence. Removal of the signal peptide by the normal post-translational cleavage event will produce a mature hEPO molecule whose primary sequence is indistinguishable from the normal product.

Transfection of pREPO15 into human fibroblasts resulted in EPO expression by these cells. Table 5 shows the results of targeting experiments with pREPO15 in human fibroblasts and HT1080 cells. The targeting frequency in normal human fibroblasts was found to be 1/264 G418® colonies, and the targeting frequency with HT1080 cells was found to be 1/450 G418® colonies. hEPO production levels from each of these cell strains was quantified. An hEPO producer obtained from transfection of human fibroblasts was found to be secreting 7,679 $mU/10^6$ cells/day (Table 5). An activated hEPO cell line from HT1080 cells was producing 12,582 $mU/10^6$ cells/day (Table 5). These results indicated that activation of the hEPO locus was efficient and caused hEPO to be produced constituitively at relatively high levels. Restriction enzyme and Southern hybridization analysis was used to confirm that targeting events had occurred at the EPO locus.

Figure 9A:
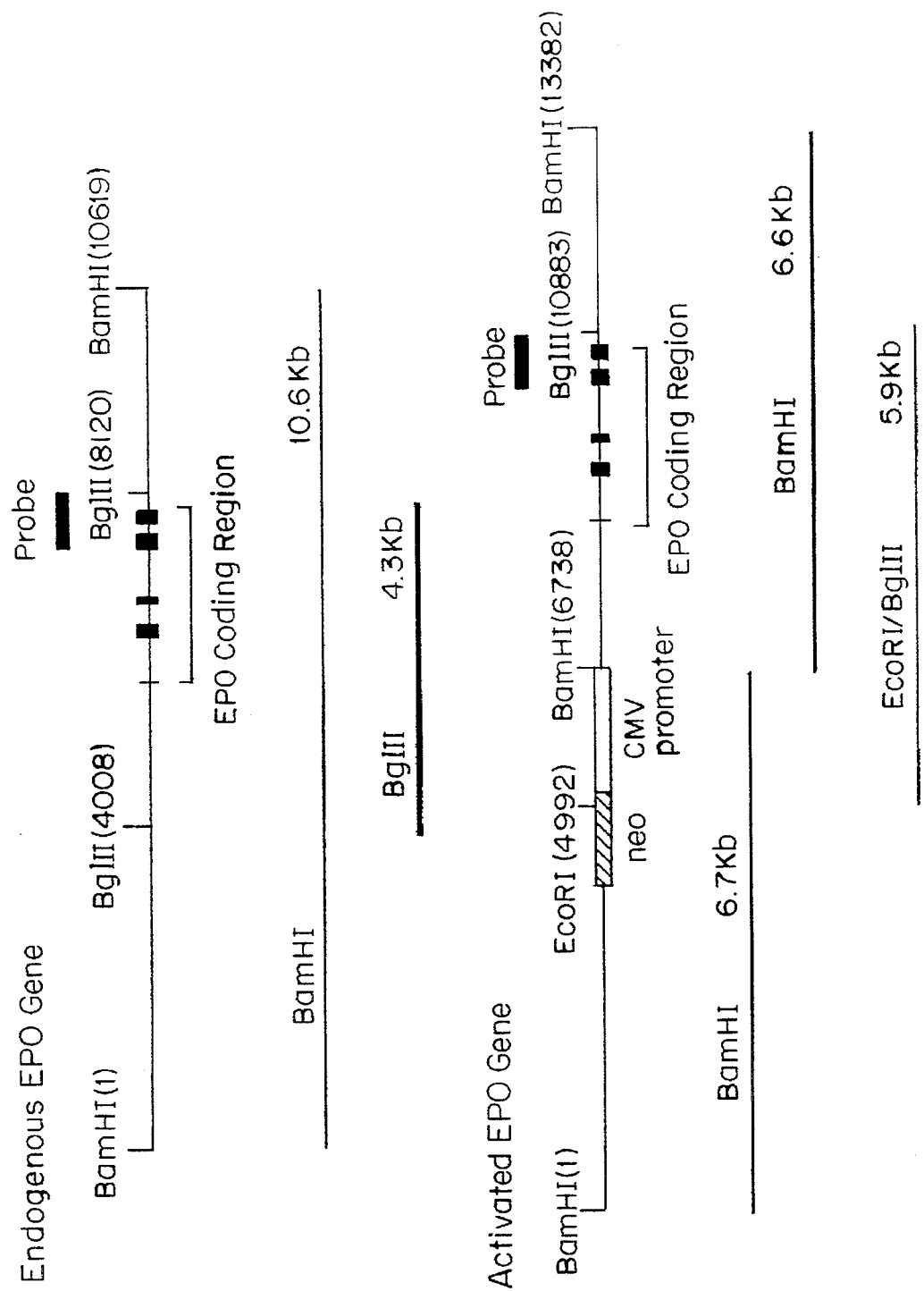
FIG. 9A presents restriction enzyme maps and schematic representations of the products observed upon digestion of the endogenous hEPO gene (top) and the activated hEPO gene after homologous recombination with the targeting fragment from pREPO15 (bottom).
Figure 9B:
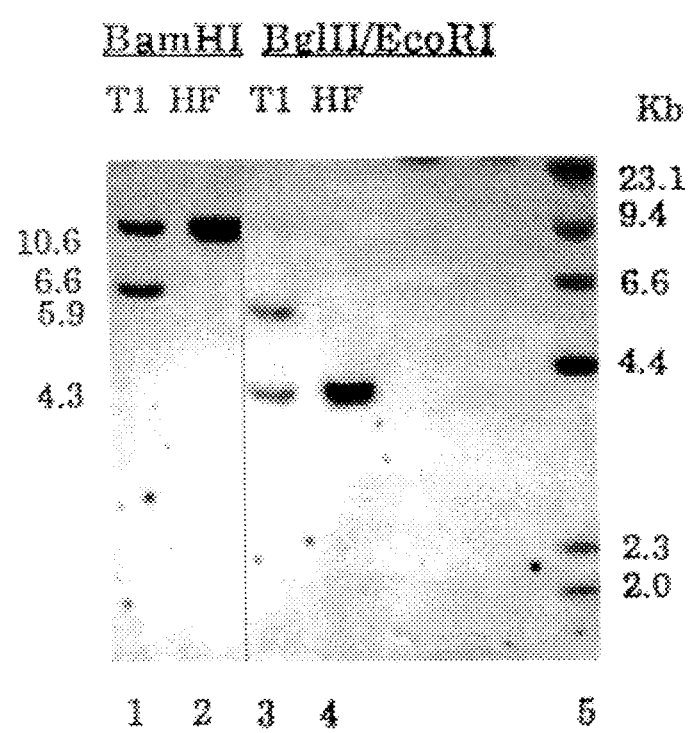
FIG. 9B presents the results of restriction enzyme digestion and Southern hybridization analysis of untreated (HF) and targeted (T1) human fibroblast clone HF342-15 (see Example 7).

Southern blot analysis of the human fibroblast and HT1080 clones that were targeted with pREPO15 was performed. FIG. 9A shows the restriction map of the parental and targeted hEPO locus, and FIG. 9B shows the results of restriction enzyme and Southern hybridization analysis of a targeted human fibroblast clone. BglII/EcoRI and BamHI digests revealed 5.9 and 6.6 kb fragments, respectively, as a result of a targeting event at the hEPO locus (lanes T1). Both of these fragments resulted from the insertion of 2.7 kb of DNA containing the neo gene and CMV promoter sequences. Since only one of the two hEPO alleles were targeted, fragments of 4.3 kb (BglII/EcoRI) or 10.6 kb (BamHI) reflecting the unaltered hEPO locus were seen in these strains and in parental DNA (lanes HF). These results confirm that a homologous recombination event had occurred at the hEPO locus resulting in the production of a novel transcription unit which directed the production of human erythropoietin.

| Oligonucleotide | Sequence |
| --- | --- |
| 20 | 5' TTTTCTCGAG TCGACGACAT TGATTATTGA CTAGT (SEQ ID NO: 18) |
| 35 | 5' TTTTAAGCTT GAGTACTCAC CTGTAGCCAT GGTGGATCCC GT (SEQ ID NO: 19) |

TABLE 5

Transfection of pREPO15 and Activation of hEPO Expression in Human Cells

| Cell Type Transfected | Cells Treated | [a]G418[r] Colonies | [b]Plates With EPO Expressors | hEPO Expressors per G418[r] Colony | hEPO Expressors per Treated Cell | [c]hEPO Expression (mU/10$^6$ cells/24 hr) |
|---|---|---|---|---|---|---|
| Human Fibroblasts | $3.3 \times 10^7$ | 264 | 1 | 1/264 | $1/3.3 \times 10^7$ | 7679 |
| HT1080 Cells | $3.1 \times 10^7$ | 2700 | 6 | 1/450 | $1/5.2 \times 10^6$ | 12,582 |

[a]estimated by counting colonies on 2 plates, averaging the results and extrapolating to the total number of plates
[b]medium from plates with G418[r] colonies was sampled for EPO ELISA analysis and those exhibiting hEPO levels greater than 5 mU/ml were counted as EPO activation events
[c]quantitative hEPO production was determined from human fibroblast strain, HF342-15 or HT1080 cell line, HTREPO15-1-6-6

Figure 10:
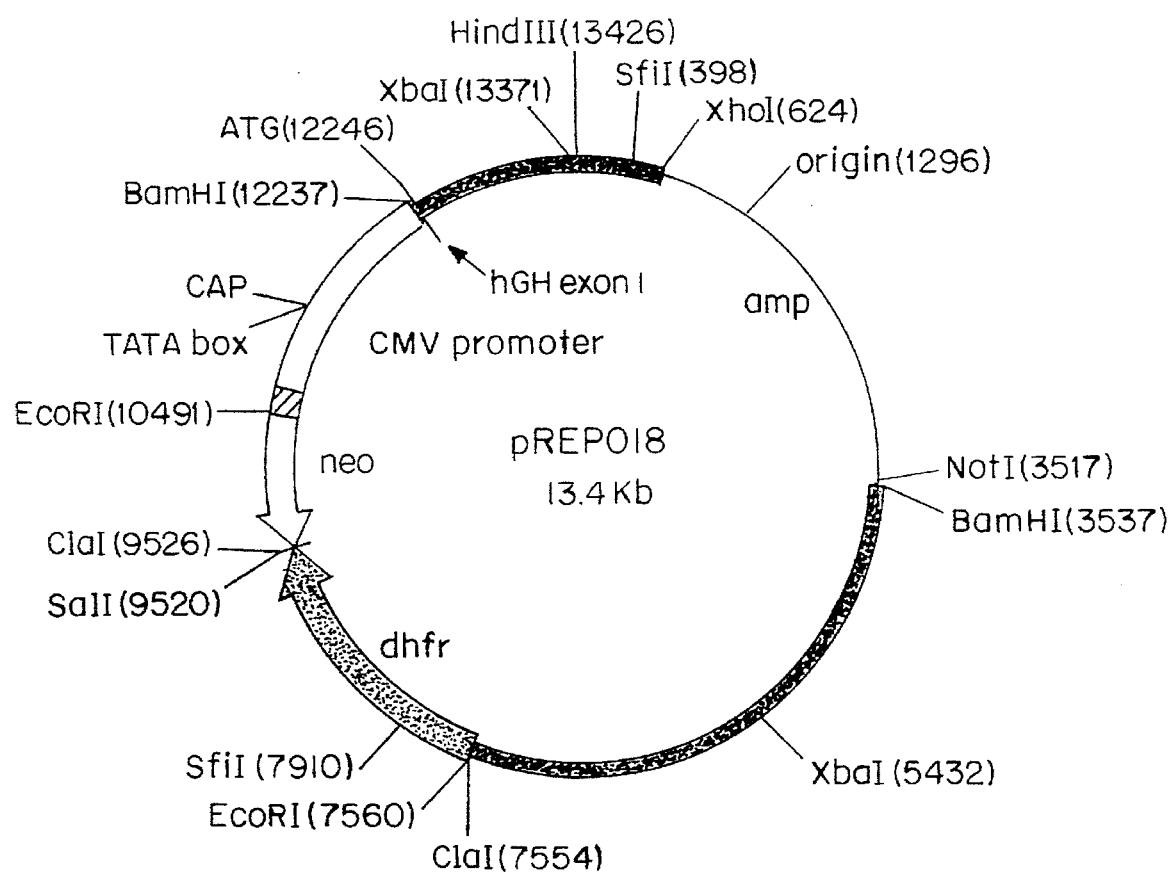
FIG. 10 is a schematic representation of plasmid pREPO18. Fragments derived from genomic hEPO sequences are indicated by filled boxes. The region between BamHI (3537) and ClaI (7554) corresponds to sequences at positions 1–4008 in Genbank entry HUMERPALU. The region between ATG (12246) and HindIII (13426) corresponds to DNA sequence at positions 4009–5169 in Genbank entry HUMERPLAU. The region between HindIII (13426) and XhoI (624) contains sequence corresponding to positions 7–624 of Genbank entry HUMERPA. CMV promoter sequences are shown as an open box and contains sequence from nucleotides 546–2015 of Genbank sequence HS5MIEP. The dihydrofolate reductase (dhfr) transcription unit is shown as a stippled box with an arrow. The neo gene is shown as an open box with an arrow. The tk promoter driving the neo gene is shown as a hatched box. pBSIISK+ sequences including the amp gene are indicated by a thin line.

Example 8: PRODUCTION AND AMPLIFICATION OF AN hEPO FUSION GENE BY INSERTION OF THE CMV PROMOTER 1.8 KB UPSTREAM OF THE GENOMIC hEPO CODING REGION Construction of targeting plasmid pREPO18:

pREPO18 (FIG. 10) was constructed by insertion of a dhfr expression unit at the ClaI site located at the 5' end of the neo gene of pREPO15. To obtain a dhfr expression unit, the plasmid construct pF8CIS9080 [Eaton et al., *Biochemistry* 25:8343–8347 (1986)] was digested with EcoRI and SalI. A 2 kb fragment containing the dhfr expression unit was purified from this digest and made blunt by treatment with the Klenow fragment of DNA polymerase I. A ClaI linker (New England Biolabs) was then ligated to the blunted dhfr fragment. The products of this ligation were then digested with ClaI ligated to ClaI digested pREPO15. An aliquot of this ligation was transformed into *E. coli* and plated on ampicillin selection plates. Bacterial colonies were analyzed by restriction enzyme digestion to determine the orientation of the inserted dhfr fragment. One plasmid with dhfr in a transcriptional orientation opposite that of the neo gene was designated pREPO18(−). A second plasmid with dhfr in the same transcriptional orientation as that of the neo gene was designated pREPO18(+)

Cell culture, transfection, and identification of EPO expressing targeted clones:

All cells were maintained at 37° C., 5% $CO_2$, and 98% humidity in DMEM containing 10% calf serum (DMEM/10, HyClone Laboratories). Transfection of HT1080 cells (ATCC, CCL 121) occurred by treating $12 \times 10^6$ cells in PBS (GIBCO) with 45 μg of DNA at 450 volts and 250 μF. The treated cells were seeded at $1 \times 10^6$ cells per 150 mm plate. The following day, the media was changed to DMEM/10 containing 0.8 mg/ml G418 (GIBCO). Selection proceeded for 14 days, at which time the media was sampled for hEPO production. Plates exhibiting significant hEPO production levels (>5 mU/ml) as determined by an hEPO ELISA (Genzyme Inc.) were trypsinized and the cells were re-plated for clone isolation. Isolation of hEPO producing clonal cell lines occurred by limiting dilution, by first plating clones in pools of 10–15 colonies per well of a 24 well plate, and next plating cells from hEPO producing pools at cell densities resulting in less than 1 colony per well of a 96 well plate. Individual clones were expanded in culture for freezing, nucleic acid isolation and quantification of hEPO production.

Isolation of cells containing amplified dhfr sequences by methotrexate selection:

Targeted G418® cell lines producing hEPO following transfection with pREPO18 were plated at various cell densities for selection in methotrexate (MTX). As new clones emerged following selection at one MTX concentration, they were assayed for hEPO production and re-plated at various cell densities in a higher concentration of MTX (usually double the previous concentration). This process was repeated until the desired hEPO production level was reached. At each step of MTX-resistance, DNA and RNA was isolated for respective southern and northern blot analysis.

Characterization of EPO expressing clones:

pREPO18, with two different orientations of dhfr, was transfected into HT1080 cells. Prior to transfection, pREPO18(+) and pREPO18(−) were digested with XbaI, releasing a 7.9 kb targeting fragment containing, in the following order, a 2.1 kb region of genomic DNA upstream of hEPO exon 1 (from −3891 to −1779 relative to the hEPO ATG start codon), a 2 kb region containing the dhfr gene, a 1.1 kb region containing the neo gene, a 1.5 kb region containing the CMV promoter fused to hGH exon 1, 10 bp of hEPO intron 1 (containing a splice-donor site), followed by a 1.1 kb region of genomic DNA upstream of hEPO exon 1 (from −1778 to −678 relative to the EPO ATG start codon). Transfection and targeting frequencies from two experiments are shown in Table 6. Five primary G418® clones were isolated from these experiments. These were expanded in culture for quantitative analysis of hEPO expression (Table 7). As pREPO18 contained the dhfr gene, it is possible to select for cells containing amplified copies of the targeting construct using MTX as described in Example 6. G418® clones confirmed to be targeted to the hEPO locus by restriction enzyme and Southern hybridization analysis were subjected to stepwise selection in MTX as described.

TABLE 6

Targeting of pREPO18 in HT1080 cells

| Construct | DNA Digest | Cells Treated | G418$^r$ Colonies | Plates With hEPO Expressors | hEPO Expressors-/G418$^r$ Colony | Primary Clones Analyzed |
|---|---|---|---|---|---|---|
| pREPO18 (−) | XbaI | 36 × 10$^6$ | 16,980 | 39 | 1/435 | 1 |
| pREPO18 (+) | XbaI | 36 × 10$^6$ | 19,290 | 41 | 1/470 | 4 |

TABLE 7 hEPO production in HT1080 Cell lines targeted with pREPO18

| Cell Line | Construct | hEPO mU/10$^6$ Cells/24 hr |
|---|---|---|
| 18B3-147 | pREPO18 (+) | 24759 |
| 18B3-181 | pREPO18 (+) | 20831 |
| 18B3-145 | pREPO18 (+) | 17586 |
| 18B3-168 | pREPO18 (+) | 5293 |
| 18A3-119 | pREPO18 (−) | 2881 |

Example 9: ACTIVATION AND AMPLIFICATION OF ENDOGENOUS α-INTERFERON, GM-CSF, G-CSF AND FSHβ GENES IN IMMORTALIZED HUMAN CELLS A wide variety of endogenous cellular genes can be activated and amplified using the methods and DNA constructs of the invention. The following describes a general strategy for activating and amplifying the human α-interferon (leukocyte interferon), GM-CSF (colony stimulating factor-granulocyte/macrophage), G-CSF (colony stimulating factor-granulocyte) and FSHβ (follicle stimulating hormone beta subunit) genes.

α-interferon

Figure 11:
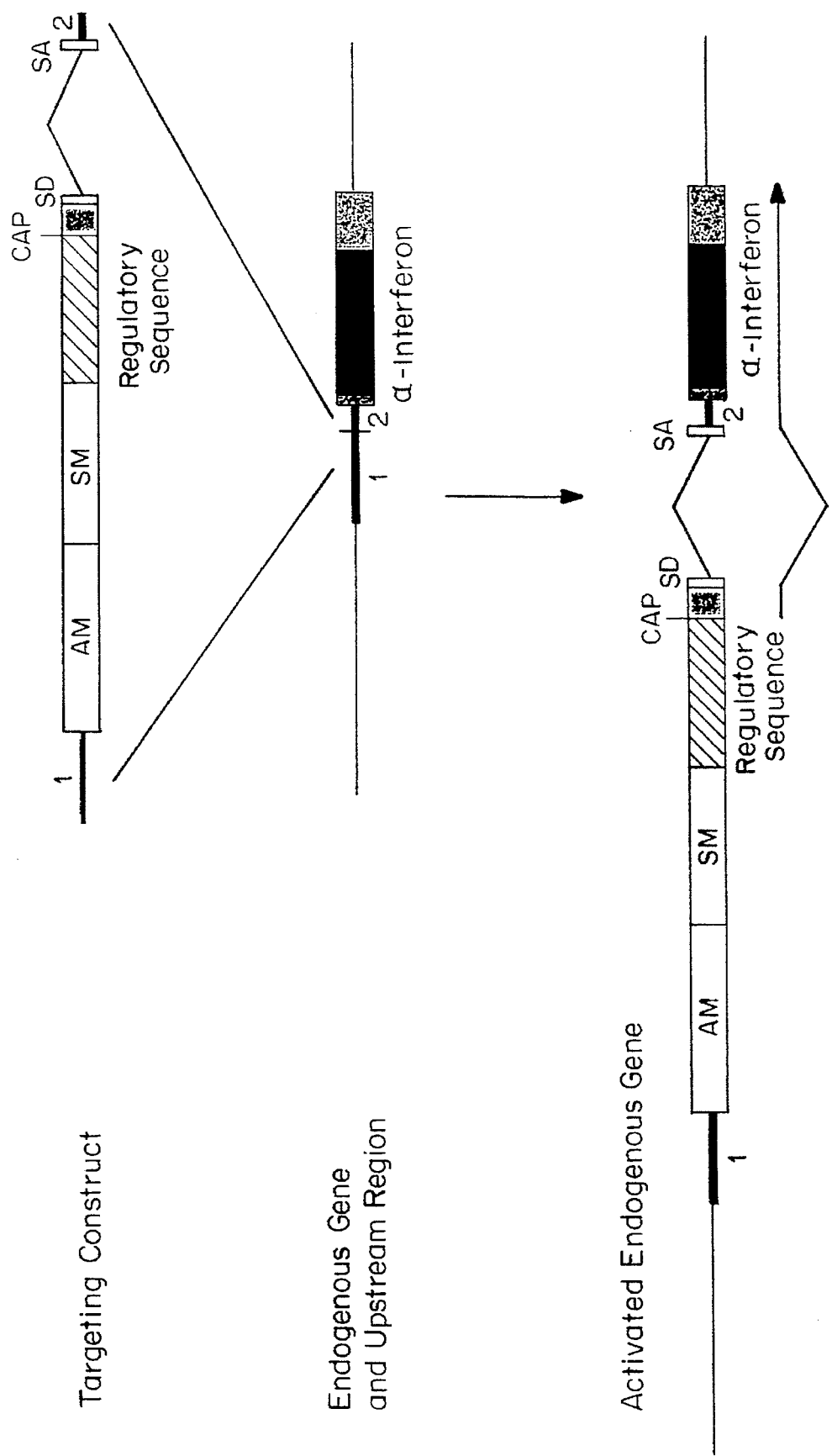
FIG. 11 is a schematic illustration of a construct of the invention for activating and amplifying an intronless gene, the α-interferon gene, where the construct comprises a first targeting sequence (1), an amplifiable marker gene (AM), a selectable marker gene (SM), a regulatory sequence, a CAP site, a splice-donor site (SD), an intron (thin lines), a splice-acceptor site (SA) and a second targeting sequence (2). The black box represents coding DNA and the stippled boxes represent untranslated sequences.

The human α-interferon gene (Genbank sequence HUMIFNAA) encodes a 188 amino acid precursor protein containing a 23 amino acid signal peptide. The gene contains no introns. FIG. 11 schematically illustrates one strategy for activating the α-interferon gene. The targeting construct is designed to include a first targeting sequence homologous to sequences upstream of the gene, an amplifiable marker gene, a selectable marker gene, a regulatory region, a CAP site, a splice-donor site, an intron, a splice acceptor site, and a second targeting sequence corresponding to sequences downstream of the first targeting sequence. The second targeting sequence should not extend further upstream than to position −107 relative to the normal start codon in order to avoid undesired ATG start codons.

In this strategy the first and second targeting sequences are immediately adjacent to each other in the normal target gene, but this is not required (see below). Amplifiable marker genes and selectable marker genes suitable for selection are described herein. The amplifiable marker gene and selectable marker gene may be the same gene, their positions may be reversed, and one or both may be situated in the intron of the targeting construct. A selectable marker gene is optional and the amplifiable marker gene is only required when amplification is desired. The incorporation of a specific CAP site is optional. Optionally, exon sequences from another gene can be included 3' to the splice-acceptor site and 5' to the second targeting sequence in the targeting construct. The regulatory region, CAP site, splice-donor site, intron, and splice acceptor site can be isolated as a complete unit from the human elongation factor-1α (EF-1α; Genbank sequence HUMEF1A) gene or the cytomegalovirus (CMV; Genbank sequence HEHCMVP1) immediate early region, or the components can be assembled from appropriate components isolated from different genes.

Genomic DNA corresponding to the upstream region of the α-interferon gene for use as targeting sequences and assembly of the targeting construct can be performed using recombinant DNA methods known by those skilled in the art. As described herein, a number of selectable and amplifiable markers can be used in the targeting constructs, and the activation and amplification can be effected in a large number of cell-types. Transfection of primary, secondary, or immortalized human cells and isolation of homologously recombinant cells expressing α-interferon can be accomplished using the methods described in Example 4, using an ELISA assay for human α-interferon (Biosource International, Camarillo, Calif.). Alternatively, homologously recombinant cells may be identified by PCR screening as described in Example 1g and 1j. The isolation of cells containing amplified copies of the amplifiable marker gene and the activated α-interferon locus is performed as described in Example 6.

In the homologously recombinant cells, an mRNA precursor is produced which includes the exogenous exon, splice-donor site, intron, splice-acceptor site, second targeting sequence, and human α-interferon coding region and 3' untranslated sequences (FIG. 11). Splicing of this message will generate a functional mRNA which can be translated to produce human α-interferon.

The size of the intron and thus the position of the regulatory region relative to the coding region of the gene may be varied to optimize the function of the regulatory region. Multiple exons may be present in the targeting construct. In addition, the second targeting sequence does not need to lie immediately adjacent to or near the first targeting sequence in the normal gene, such that portions of the gene's normal upstream region are deleted upon homologous recombination.

GM-CSF

Figure 12:
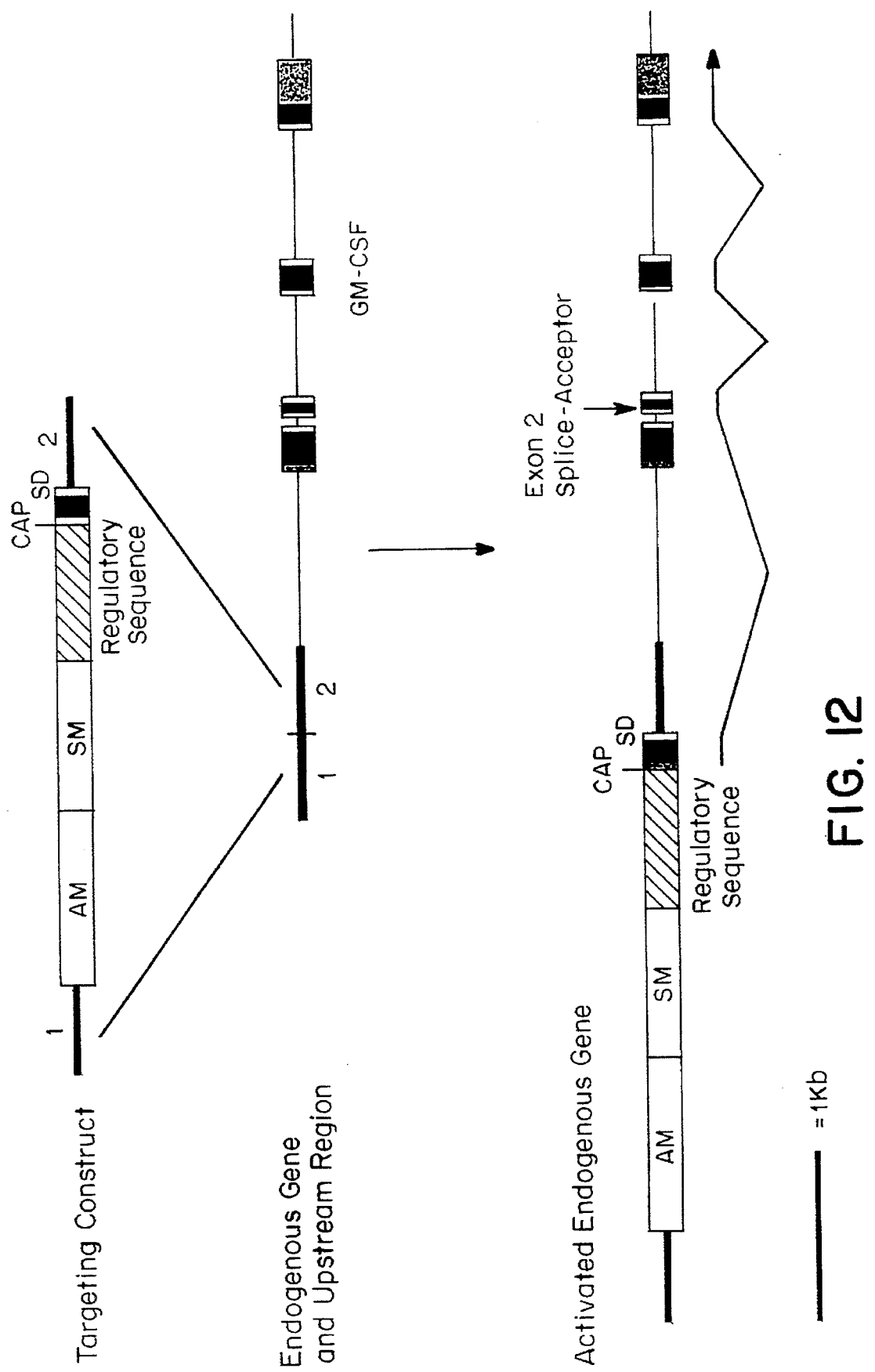
FIG. 12 is a schematic illustration of a construct of the invention for activating and amplifying an endogenous gene wherein the first exon contributes to the signal peptide, the human GM-CSF gene, where the construct comprises a first targeting sequence (1), an amplifiable marker gene (AM), a selectable marker gene (SM), a regulatory sequence, a CAP site, a splice-donor site (SD), and a second targeting sequence (2). The black boxes represent coding DNA and the stippled boxes represent untranslated sequences.

The human GM-CSF gene (Genbank sequence HUMGMCSFG) encodes a 144 amino acid precursor protein containing a 17 amino acid signal peptide. The gene contains four exons and three introns, and the N-terminal 50 amino acids of the precursor are encoded in the first exon. FIG. 12 schematically illustrates a strategy for activating the GM-CSF gene. In this strategy the targeting construct is designed to include a first targeting sequence homologous to sequences upstream of the gene, an amplifiable marker gene, a selectable marker gene, a regulatory region, a CAP site, an exon which encodes an amino acid sequence which is identical or functionally equivalent to that of the first 50 amino acids of GM-CSF, a splice-donor site, and a second targeting sequence corresponding to sequences downstream of the first targeting sequence. By this strategy, homologously recombinant cells produce an mRNA precursor which corresponds to the exogenous exon and splice-donor site, the second targeting sequence, any sequences between the second targeting sequence and the start codon of the GM-CSF gene, and the exons, introns, and 3' untranslated region of the GM-CSF gene (FIG. 11). Splicing of this message results in the fusion of the exogenous exon to exon 2 of the endogenous GM-CSF gene which, when translated, will produce GM-CSF.

In this strategy the first and second targeting sequences are immediately adjacent in the normal target gene, but this is not required (see below). Amplifiable marker genes and selectable marker genes suitable for selection are described herein. The amplifiable marker gene and selectable marker gene can be the same gene or their positions can be reversed. A selectable marker gene is optional and the amplifiable marker gene is only required when amplification is desired. The selectable marker and/or amplifiable marker can be positioned between the splice-donor site and the second targeting sequence in the targeting construct. The incorporation of a specific CAP site is optional. The regulatory region, CAP site, and splice-donor site can be isolated as a complete unit from the human elongation factor-1α (EF-1α; Genbank sequence HUMEF1A) gene or the cytomegalovirus (CMV; Genbank sequence HEHCMVP1) immediate early region, or the components can be assembled from an appropriate component isolated from different genes (such as the mMT-I promoter and CAP site, and exon 1 and a splice donor site from the hGH or hEPO genes.

Other approaches can be employed, for example, the first and second targeting sequences can correspond to sequences in the first intron of the GM-CSF gene. Alternatively, a targeting construct similar to that described for the α-interferon can be used, in which the targeting construct is designed to include a first targeting sequence homologous to sequences upstream of the GM-CSF gene, an amplifiable marker gene, a selectable marker gene, a regulatory region, a CAP site, a splice-donor site, an intron, a splice acceptor site, and a second targeting sequence corresponding to sequences downstream of the first targeting sequence.

In any case the second targeting sequence does not need to lie immediately adjacent to or near the first targeting sequence in the normal gene, such that portions of the gene's normal upstream region are deleted upon homologous recombination. In addition, multiple non-coding or coding exons can be present in the targeting construct. Genomic DNA corresponding to the upstream or intron regions of the human GM-CSF gene for use as targeting sequences and assembly of the targeting construct can be performed using recombinant DNA methods known by those skilled in the art. As described herein, a number of selectable and amplifiable markers can be used in the targeting constructs, and the activation can be effected in a large number of cell-types. Transfection of primary, secondary, or immortalized human cells and isolation of homologously recombinant cells expressing GM-CSF can be accomplished using the methods described in Example 4, using an ELISA assay for human GM-CSF (R&D Systems, Minneapolis, Minn.). Alternatively, homologously recombinant cells may be identified by PCR screening as described above. The isolation of cells containing amplified copies of the amplifiable marker gene and the activated GM-CSF locus is performed as described above.

G-CSF

Figure 13:
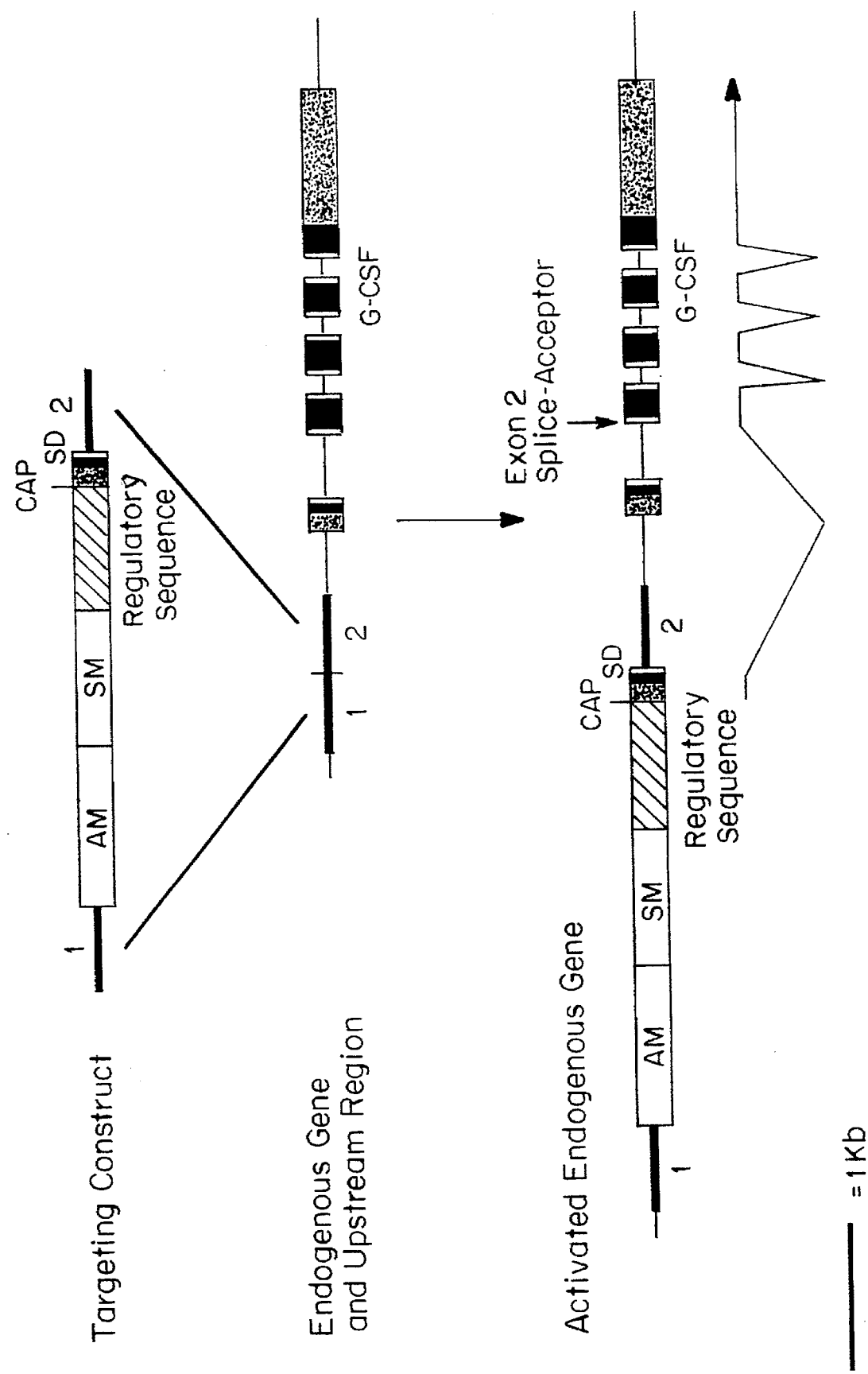
FIG. 13 is a schematic illustration of a construct of the invention for activating and amplifying an endogenous gene wherein the first exon contributes to the signal peptide, the human G-CSF gene, where the construct comprises a first targeting sequence (1), an amplifiable marker gene (AM), a selectable marker gene (SM), a regulatory sequence, a CAP site, a splice-donor site (SD), and a second targeting sequence (2). The black boxes represent coding DNA and the stippled boxes represent untranslated sequences.

The human G-CSF gene (Genbank sequence HUMGCSFG) encodes 204–207 amino acid precursor protein containing a 30 amino acid signal peptide. The gene contains five exons and four introns. The first exon encodes 13 amino acids of the signal peptide. FIG. 13 schematically illustrates a strategy for activating the G-CSF gene. The targeting construct is designed to include a first targeting sequence homologous to sequences upstream of the gene, an amplifiable marker gene, a selectable marker gene, a regulatory region, a CAP site, an exon which encodes an amino acid sequence which is identical or functionally equivalent to that of the first 13 amino acids of the G-CSF signal peptide, a splice- donor site, and a second targeting sequence corresponding to sequences downstream of the first targeting sequence. By this strategy, homologously recombinant cells produce an mRNA precursor which corresponds to the exogenous exon and splice-donor site, the second targeting sequence, any sequences between the second targeting sequence and the start codon of the G-CSF gene, and the exons, introns, and 3' untranslated region of the G-CSF gene (FIG. 13). Splicing of this message results in the fusion of the exogenous exon to exon 2 of the endogenous G-CSF gene which, when translated, will produce G-CSF. The ability to functionally substitute the first 13 amino acids of the normal G-CSF signal peptide with those present in the exogenous exon allows one to make modifications in the signal peptide, and hence the secretory properties of the protein produced.

In this strategy the first and second targeting sequences are immediately adjacent in the normal target gene, but this is not required. The second targeting sequence does not need to lie immediately adjacent to or near the first targeting sequence in the normal gene, such that portions of the gene's normal upstream region are deleted upon homologous recombination. The amplifiable marker gene and selectable marker gene can be the same gene or their positions can be reversed. A selectable marker gene is optional and the amplifiable marker gene is only required when amplification is desired. The selectable marker and/or amplifiable marker can be positioned between the splice-donor site and the second targeting sequence in the targeting construct. The incorporation of a specific CAP site is optional. The regulatory region, CAP site, and splice-donor site can be isolated as a complete unit from the human elongation factor-1α (EF-1α; Genbank sequence HUMEF1A) gene or the cytomegalovirus (CMV; Genbank sequence HEHCMVP1) immediate early region, or the components can be assembled from an appropriate component isolated from different genes (such as the mMT-I promoter and CAP site, and exon 1 and a splice donor site from the hGH or EPO genes. Multiple exogenous exons, coding or non-coding, can be used in the targeting construct so long as an ATG start codon which, upon splicing, will be in-frame with the mature protein, is included in one of the exons.

Other approaches may be employed, for example, the first and second targeting sequences can correspond to sequences in the first intron of the G-CSF gene. Alternatively, a targeting construct similar to that described for the α-interferon can be used, in which the targeting construct is designed to include a first targeting sequence homologous to sequences upstream of the G-CSF gene, an amplifiable marker gene, a selectable marker gene, a regulatory region, a CAP site, a splice-donor site, an intron, a splice acceptor site, and a second targeting sequence corresponding to sequences downstream of the first targeting sequence.

Genomic DNA corresponding to the upstream or intron regions of the human G-CSF gene for use as targeting sequences and assembly of the targeting construct can be performed using recombinant DNA methods known by those skilled in the art. As described herein, a number of selectable and amplifiable markers can be used in the targeting constructs, and the activation can be effected in a large number of cell-types. Transfection of primary, secondary, or immortalized human cells and isolation of homologously recombinant cells expressing G-CSF can be accomplished using the methods described in Example 4, using an ELISA assay for human G-CSF (R&D Systems, Minneapolis, Minn.). Alternatively, homologously recombinant cells may be identified by PCR screening as described above. The isolation of cells containing amplified copies of the amplifiable marker gene and the activated α-interferon locus is performed as described above.

FSHβ

Figure 14:
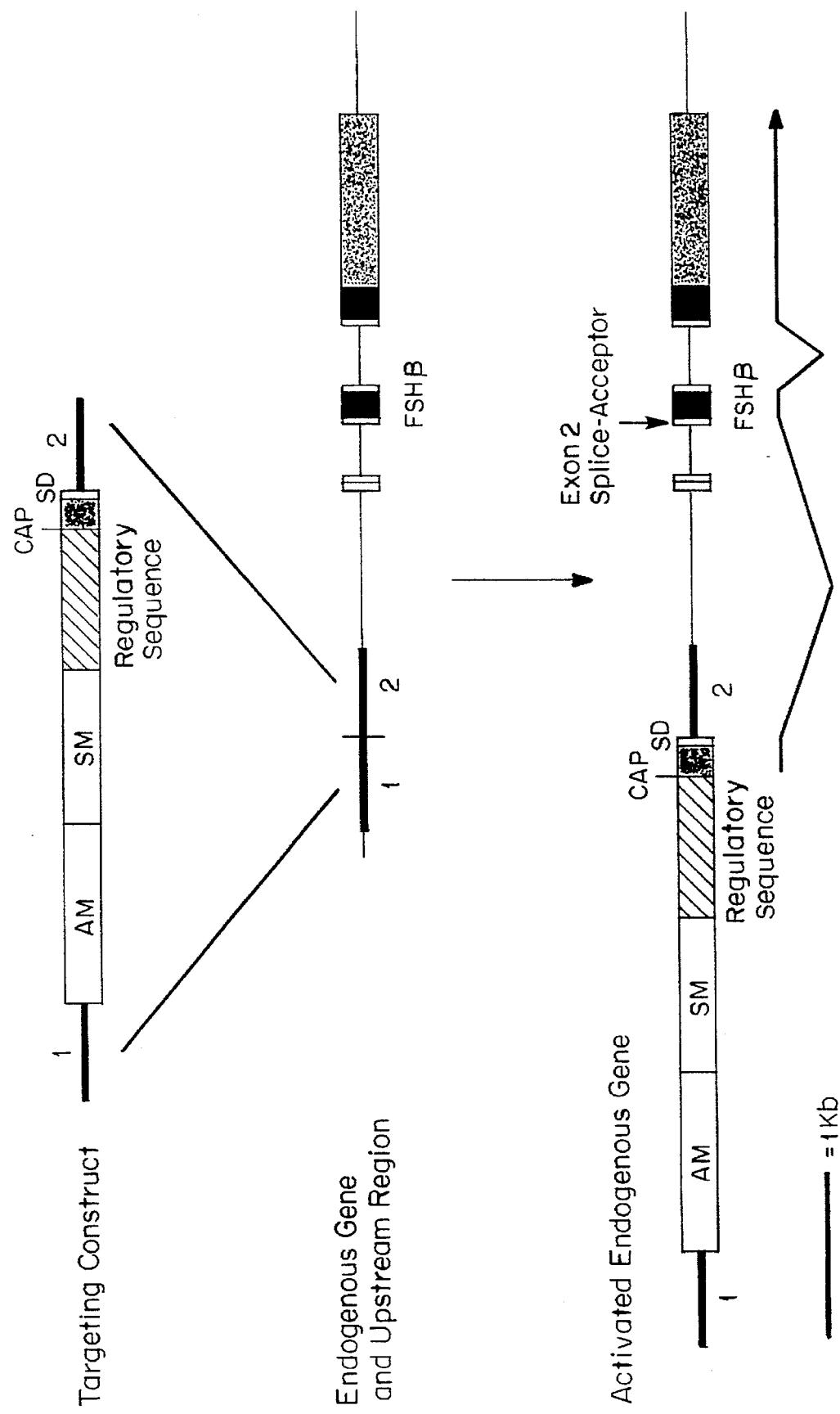
FIG. 14 is a schematic illustration of a construct of the invention for activating and amplifying an endogenous gene wherein the first exon is non-coding, the human FSHβ gene, where the construct comprises a first targeting sequence (1), an amplifiable marker gene (AM), a selectable marker gene (SM), a regulatory sequence, a CAP site, a splice-donor site (SD), and a second targeting sequence (2). The black boxes represent coding DNA and the stippled boxes represent untranslated sequences.

The human FSHβ gene (Genbank sequence HUMFSH1) encodes a 129 amino acid precursor protein containing a 16 amino acid signal peptide. The gene contains three exons and two introns, with the first exon being a non-coding exon. The activation of FSHβ can be accomplished by a number of strategies. One strategy is shown in FIG. 14. In this strategy, a targeting construct is designed to include a first targeting sequence homologous to sequences upstream of the gene, an amplifiable marker gene, a selectable marker gene, a regulatory region, a CAP site, an exon, a splice-donor site, and a second targeting sequence corresponding to sequences downstream of the first targeting sequence. By this strategy, homologously recombinant cells produce an mRNA precursor which corresponds to the exogenous exon and splice-donor site, the second targeting sequence, any sequences between the second targeting sequence and the start codon of the FSHβ gene, and the exons, introns, and 3' untranslated regions of the FSHβ gene (FIG. 14). Splicing of this message results in the fusion of the exogenous exon to exon 2 of the endogenous FSHβ gene which, when translated, can produce FSHβ. In this strategy the first and second targeting sequences are immediately adjacent in the normal target gene, but this is not required (see below).

Other approaches can be employed, for example, the first and second targeting sequences can correspond to sequences in the first intron of the FSHβ gene. Alternatively, a targeting construct similar to that described for the α-interferon can be used. In this strategy, the targeting construct is designed to include a first targeting sequence homologous to sequences upstream of the FSHβ gene, an amplifiable marker gene, a selectable marker gene, a regulatory region, a CAP site, a splice-donor site, an intron, a splice acceptor site, and a second targeting sequence corresponding to sequences downstream of the first targeting sequence. The second targeting sequence should not extend further upstream than to position −40 relative to the normal FSHβ transcriptional start site in order to avoid undesired ATG start codons. In the homologously recombinant cells, an mRNA precursor is produced which includes the exogenous exon, splice-donor site, intron, splice-acceptor site, second targeting sequence, and human FSHβ coding exons, intron and 3' untranslated sequences. Splicing of this message will generate a functional mRNA which can be translated to produce human FSHβ. The size of the intron and thus the position of the regulatory region relative to the coding region of the gene can be varied to optimize the function of the regulatory region.

In any activation strategy, the second targeting sequence does not need to lie immediately adjacent to or near the first targeting sequence in the normal gene, such that portions of the gene's normal upstream region are deleted upon homologous recombination. Furthermore, one targeting sequence can be upstream of the gene and one may be within an exon or intron of the FSHβ gene.

The amplifiable marker gene and selectable marker gene can be the same gene, their positions can be reversed, and one or both can be situated in the intron of the targeting construct. Amplifiable marker genes and selectable marker genes suitable for selection are described herein. A selectable marker gene is optional and the amplifiable marker gene is only required when amplification is desired. The incorporation of a specific CAP site is optional. Optionally, exon sequences from another gene can be included 3' to the splice-acceptor site and 5' to the second targeting sequence in the targeting construct. The regulatory region, CAP site, exon, splice-donor site, intron, and splice acceptor site can be isolated as a complete unit from the human elongation factor-1α (EF-1α; genbank sequence HUMEF1A) gene or the cytomegalovirus (CMV; genbank sequence HEHCMVP1) immediate early region, or the components can be assembled from appropriate components isolated from different genes. In any case, the exogenous exon can be the same or different from the first exon of the normal FSHβ gene, and multiple exons can be present in the targeting construct.

Genomic DNA corresponding to the upstream region of the FSHβ gene for use as targeting sequences and assembly of the targeting construct can be performed using recombinant DNA methods known by those skilled in the art. As described herein, a number of selectable and amplifiable markers can be used in the targeting constructs, and the activation can be effected in a large number of cell-types. If desirable, the product of the activated FSHβ gene can be produced in a cell type that expresses the human glycoprotein α-subunit, the product of which forms a heterodimer with the product of the FSHβ gene. This may be a naturally occurring cell strain or line. Alternatively, the human glycoprotein α-subunit gene (Genbank sequence HUMGLYCA1) can be co-expressed with the product of the FSHβ gene, with such co-expression accomplished by expression of the human glycoprotein α-subunit gene or cDNA under the control of a suitable promoter, or by activation of the human glycoprotein α-subunit gene through the methods described herein. Transfection of primary, secondary, or immortalized human cells and isolation of homologously recombinant cells expressing FSHβ can be accomplished using the methods described above using an ELISA assay for human FSHβ (Accurate Chemical and Scientific, Westbury, N.Y.). Alternatively, homologously recombinant cells may be identified by PCR screening as described above. The isolation of cells containing amplified copies of the amplifiable marker gene and the activated α-interferon locus is performed as described above.

Equivalents

Those skilled in the art will recognize, or be able to ascertain using not more than routine experimentation, many equivalents to the specific embodiments of the invention described herein. Such equivalents are intended to be encompassed by the following claims.

We claim:

1. A homologously recombinant cell having incorporated therein a new transcription unit, wherein the new transcription unit comprises an exogenous regulatory sequence, an exogenous exon and a splice-donor site, operatively linked to the second exon of an endogenous gene, wherein the homologously recombinant cell comprises said exogenous exon in addition to exons present in said endogenous gene.

2. The homologously recombinant cell of claim 1 wherein the exogenous exon comprises a CAP site.

3. The homologously recombinant cell of claim 1 wherein the exogenous exon further comprises the nucleotide sequence ATG.

4. The homologously recombinant cell of claim 3 wherein the exogenous exon further comprises encoding DNA in-frame with the targeted endogenous gene.

5. The homologously recombinant cell of claim 4 wherein the encoding DNA is different from the encoding DNA of the first exon of the endogenous gene.

6. The homologously recombinant cell of claim 4 wherein the exogenous regulatory sequence, exogenous exon and splice-donor site are upstream of the coding region of the endogenous gene.

7. The homologously recombinant cell of claim 6 wherein the exogenous regulatory sequence, exogenous exon and splice-donor site are upstream of the endogenous regulatory sequence of the endogenous gene.

8. The homologously recombinant cell of claim 1 wherein the endogenous regulatory sequence is deleted.

9. The homologously recombinant cell of claim 4 wherein the endogenous gene encodes a hormone, a cytokine, an antigen, an antibody, an enzyme, a clotting factor, a transport protein, a receptor, a regulatory protein, a structural protein or a transcription factor.

10. The homologously recombinant cell of claim 4 wherein the endogenous gene encodes a protein selected from the group consisting of erythropoietin, calcitonin, growth hormone, insulin, insulinotropin, insulin-like growth factors, parathyroid hormone, β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte, CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNAse, α-galactosidase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 antagonists, alpha-1 antitrypsin, immune response modifiers, and soluble CD4.

11. The homologously recombinant cell of claim 1 wherein the cell is a eukaryote.

12. The homologously recombinant cell of claim 11 wherein the cell is of fungal, plant or animal origin.

13. The homologously recombinant cell of claim 12 wherein the cell is of vertebrate origin.

14. The homologously recombinant cell of claim 13 wherein the cell is a primary or secondary mammalian cell.

15. The homologously recombinant cell of claim 13 wherein the cell is a primary or secondary human cell.

16. The homologously recombinant cell of claim 13 wherein the cell is an immortalized mammalian cell.

17. The homologously recombinant cell of claim 13 wherein the cell is an immortalized human cell.

18. The homologously recombinant cell of claim 13 wherein the cell is selected from the group consisting of: HT1080 cells, HeLa cells, derivatives of HeLa cells, MCF-7 breast cancer cells, K-562 leukemia cells, KB carcinoma cells, 2780AD ovarian carcinoma cells, Raji cells, Jurkat cells, Namalwa cells, HL-60 cells, Daudi cells, RPMI 8226 cells, U-937 cells, Bowes Melanoma cells, WI-38VA13 subline 2R4 cells, and MOLT-4 cells.

19. The homologously recombinant cell of claim 18 wherein the endogenous gene encodes erythropoietin.

20. The homologously recombinant cell of claim 19 which expresses erythropoietin.

21. The homologously recombinant cell of claim 4 wherein the encoding DNA is the same as the encoding DNA of the first exon of erythropoietin.

22. The homologously recombinant cell of claim 4 wherein the encoding DNA is different from the encoding DNA of the first exon of erythropoietin.

23. The homologously recombinant cell of claim 22 wherein the encoding DNA is the same as the encoding DNA of the first exon of human growth hormone.

24. The homologously recombinant cell of claim 1 which expresses a fusion protein comprising amino acids encoded by the exogenous exon and amino acids encoded by the endogenous gene.

25. The homologously recombinant cell of claim 5 wherein the regulatory sequence is a promoter, an enhancer, a scaffold-attachment region or a transcription factor binding site.

26. The homologously recombinant cell of claim 25 wherein the exogenous regulatory sequence is a promoter.

27. The homologously recombinant cell of claim 25 wherein the exogenous regulatory sequence is a regulatory sequence of the mouse metallothionein-I gene, a regulatory sequence of an SV-40 gene, a regulatory sequence of a cytomegalovirus gene, a regulatory sequence of a collagen gene, a regulatory sequence of an actin gene, a regulatory sequence of an immunoglobulin gene, a regulatory sequence of the HMG-CoA reductase gene or a regulatory sequence of the EF-1α gene.

28. The DNA plasmid pREPO18.

29. A homologously recombinant cell comprising the dhfr gene, the neo gene, the CMV promoter, hGH exon 1 and an unpaired splice-donor site targeted to a position upstream of the endogenous erythropoietin regulatory region.

30. The homologously recombinant cell of claim 29 produced by the integration of DNA from pREPO18.

* * * * *

UNITED STATES PATENT AND TRADEMARK OFFICE
CERTIFICATE OF CORRECTION

PATENT NO. : 5,641,670
DATED : June 24, 1997
INVENTOR(S) : Douglas A. Treco, Michael W. Heartlein and Richard F. Selden It is certified that error appears in the above-indentified patent and that said Letters Patent is hereby corrected as shown below:

Title page, item
 [75] Delete "Richard F. Selden" and insert --Richard F Selden--.
 Claim 3, line 59: delete "1" and insert --2--.

Claim 22, line 6: delete "4" and insert --19--.

Signed and Sealed this

Twenty-eighth Day of October, 1997

Attest:

BRUCE LEHMAN

Attesting Officer

Commissioner of Patents and Trademarks